US010869918B2

(12) United States Patent
Feldman et al.

(10) Patent No.: US 10,869,918 B2
(45) Date of Patent: Dec. 22, 2020

(54) ACINETOBACTER O-OLIGOSACCHARYLTRANSFERASES AND USES THEREOF

(71) Applicant: VaxNewMo LLC, St. Louis, MO (US)

(72) Inventors: Mario Feldman, St. Louis, MO (US); Mohamed Adel Nasr, Edmonton (CA)

(73) Assignee: VAXNEWMO LLC, St. Louis, MO (US)

( * ) Notice: Subject to any disclaimer, the term of this patent is extended or adjusted under 35 U.S.C. 154(b) by 0 days.

(21) Appl. No.: 16/390,833

(22) Filed: Apr. 22, 2019

(65) Prior Publication Data

US 2019/0343945 A1 Nov. 14, 2019

Related U.S. Application Data

(63) Continuation of application No. 15/553,733, filed as application No. PCT/CA2016/050208 on Feb. 26, 2016, now Pat. No. 10,265,391.

(60) Provisional application No. 62/121,439, filed on Feb. 26, 2015.

(51) Int. Cl.
| | |
|---|---|
| *A61K 39/09* | (2006.01) |
| *C07K 14/315* | (2006.01) |
| *C12N 9/10* | (2006.01) |
| *C12P 21/00* | (2006.01) |
| *A61K 39/00* | (2006.01) |

(52) U.S. Cl.
CPC ............ *A61K 39/09* (2013.01); *C07K 14/315* (2013.01); *C12N 9/1081* (2013.01); *C12P 21/005* (2013.01); *A61K 2039/6087* (2013.01); *Y02A 50/47* (2018.01)

(58) Field of Classification Search
None
See application file for complete search history.

(56) References Cited

U.S. PATENT DOCUMENTS

2011/0243980 A1 10/2011 Feldman et al.

FOREIGN PATENT DOCUMENTS

| JP | 2010515430 A | 5/2010 |
|---|---|---|
| WO | 2008093165 A2 | 8/2008 |
| WO | 2014057109 A1 | 4/2014 |
| WO | 2014072405 A1 | 5/2014 |

OTHER PUBLICATIONS

Bernatchez et al., "A Single Biofunctional UDP-GlgNAc/Glc 4-epimerase Supports the Synthesis of Three Cell Surface Glycoconjugates in Campylobacter Jejuni", Journal of Biological Chemistry, American Society for Biochemistry and Molecular Biology, Feb. 11, 2005, pp. 4792-4802, vol. 280, No. 6.
Harding et al., "Acinetobacter Strains Carry Two Functional Oligosaccharyltransferases, One Devoted Exclusively to Type IV Pilin, and the Other One Dedicated to O-glycosylation of Multiple Proteins", Molecular Microbiology, Jun. 2015, p. 1023-1041, vol. 96, No. 5.
Iwashkiw et al., "Identification of General O-Linked Protein Glycosylation System in Acinetobacter Baumannii and Its Role in Virulence and Biofilm Formation", PLOS Pathogens, Jun. 2012, vol. 8, No. 6.
Porstendorfer et al., "ComP, A Pilin-Like Protein Essential for Natural Competence in Acinetobacter sp. Strain BD413: Regulation, Modification, and Cellular Localization", Journal of Bacteriology, Jul. 2000, pp. 3673-3680, vol. 182, No. 13.
Schulz et al., "Identification of Bacterial Protein O-Oligosaccharyltransferases and Their Glycoprotein Substrates", PLoS One, May 3, 2013, pp. e62768, vol. 8, No. 5.
Search Report and Written Opinion for PCT/CA2016/050208 dated Sep. 1, 2016.
Terra et al., "Recent Developments in Bacterial Protein Glycan Coupling Technology and Glycoconjugate Vaccine Design", Journal of Medical Microbiology, Jul. 2012, pp. 919-926, vol. 61, No. 7.
Vaneechoutte et al., "Naturally Transformable Acinetobacter sp. Strain ADP1 Belongs to the Newly Described Species Acinetobacter baylyi", Applied and Environmental Microbiology, Jan. 2006, pp. 932-936, vol. 72, No. 1.

*Primary Examiner* — Oluwatosin A Ogunbiyi
(74) *Attorney, Agent, or Firm* — Thompson Coburn LLP; William A. Holtz

(57) ABSTRACT

The present application provides methods and uses of O-oligosaccharyltransferase (O-OTases) for generating vaccines. In particular, the present application provides a method of synthesizing a glycoprotein comprising glycosylation of pilin-like protein ComP using a $PglL_{ComP}$ O-OTase. Uses of glycoproteins synthesized by glycosylating ComP using $PglL_{ComP}$ O-OTase, particularly for the preparation of vaccines and the like, including a vaccine to *Streptococcus*, is also provided.

16 Claims, 29 Drawing Sheets

Specification includes a Sequence Listing.

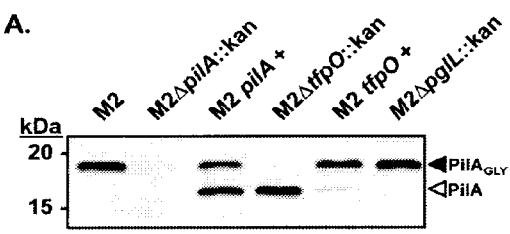
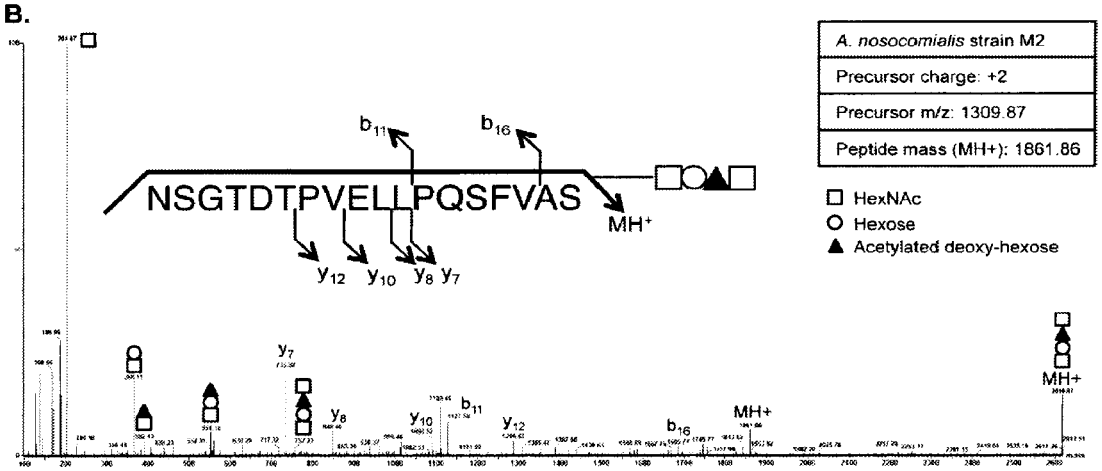
FIGURE 2

A.
| | Anti-His | Anti-Glycan |
|---|---|---|
| ComP | + + | + + |
| C. Jejuni LLO | + + | + + |
| PgIL$_{ComP}$ | − + | − + |
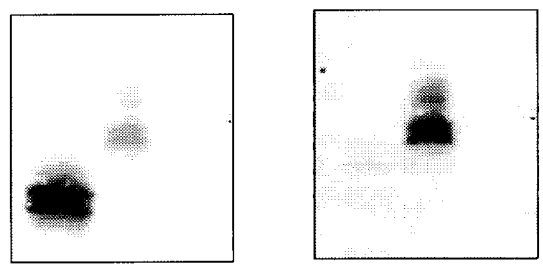
B.
| ComP | + + |
|---|---|
| E. coli O7 | + + |
| PgIL$_{ComP}$ | − + |
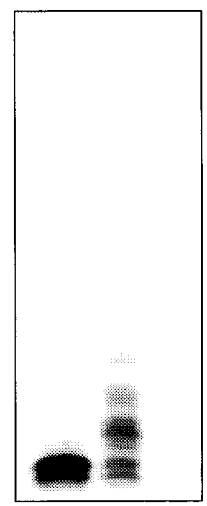
FIGURE 12

B.
C.
FIGURE 13 (continued)

A.
B.
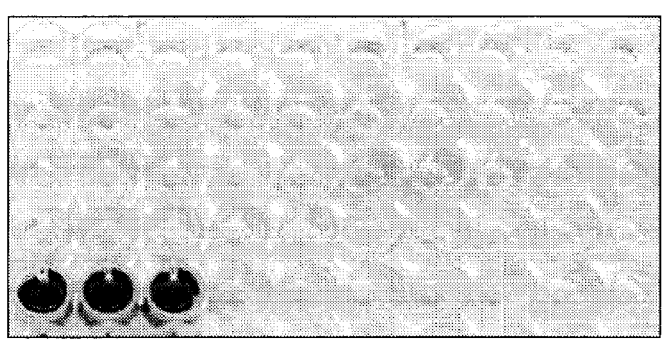
C.
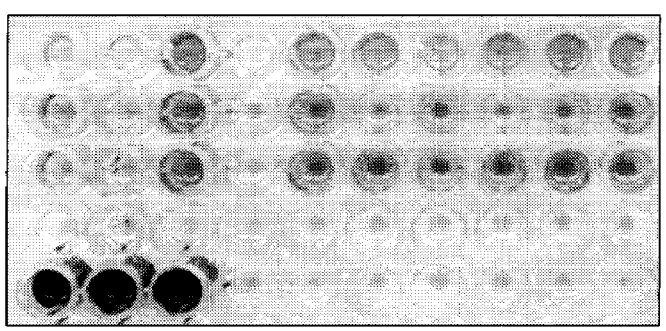
FIGURE 14

A.
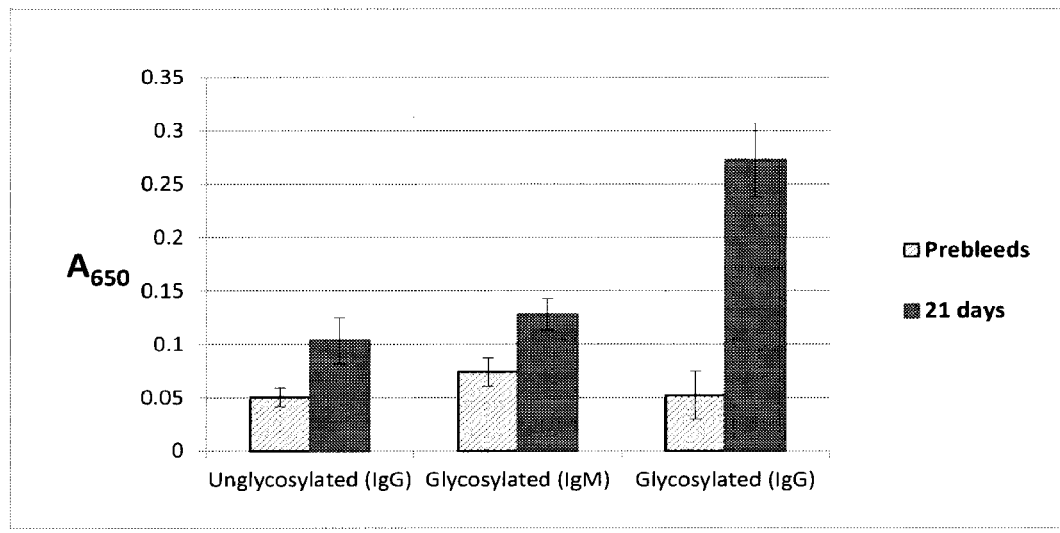
B.
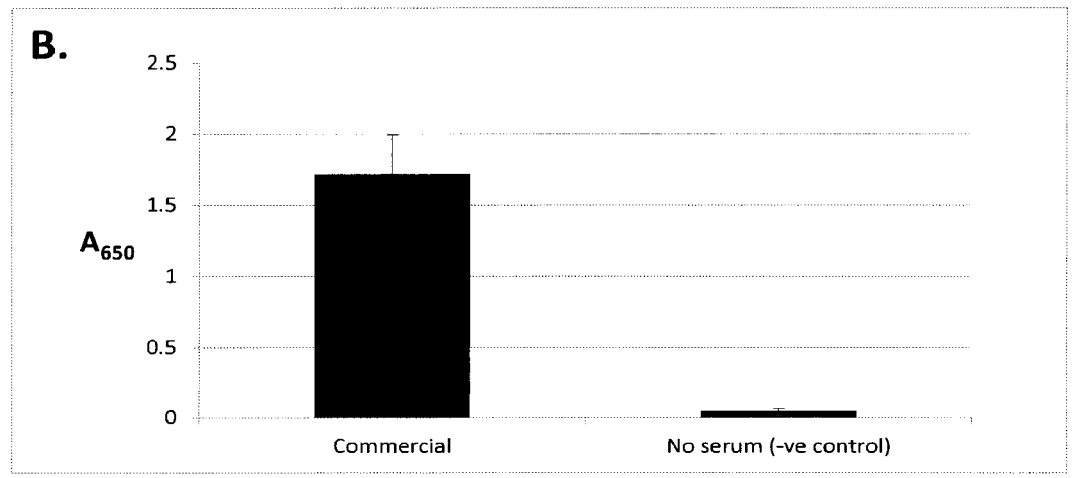
FIGURE 16

| Reducing end glycan | Source | NmPglL | CjPglB | PglL$_{ComP}$ |
|---|---|---|---|---|
| diNAcBac | C. jejuni LLO | Yes | Yes | Yes |
| Gal | S. enterica LT2 | Yes | No | Yes |
| FucNAc | P. aeruginosa O11 | Yes | Yes | Yes |
| Glc | S. pneumoniae CPS | No | No | Yes |
| GlcNAc | E. coli O7 | Yes | Yes | Yes |

| Protein | Area under the curve of heavy replicate 1 | Area under the curve of heavy replicate 2 | Precursor m/z [Da] Heavy | Precursor MH+ [Da] Heavy | Area under the curve of heavy replicate 1 | Area under the curve of heavy replicate 2 | Ratio M/H replicate 1 | Ratio M/H replicate 2 | Number of labels |
|---|---|---|---|---|---|---|---|---|---|
| Q6F744 | | | 970.965865 | 3850.8548 | 17105540.0000 | 21598696.0000 | 0.8990 | 0.8327 | Dimethyl (K); Dimethyl (K); Dimethyl (N-term) |
| Q6F835 | | | 986.51324 | 3943.0315 | 29505830.0000 | 39777781.0000 | 0.7520 | 0.6815 | Dimethyl (K); Dimethyl (K); Dimethyl (N-term) |
| Q6FC21 | | | 894.8317 | 3575.7020 | 11277073.0000 | 18267939.0000 | 1.7147 | 1.6566 | Dimethyl (K); Dimethyl (N-term) |
| Q6FD86 | | | 970.71827 | 3879.8493 | 13277726.0000 | 31189568.0000 | 1.8599 | 0.5874 | Dimethyl (K); Dimethyl (N-term) |
| Q6FC21 | | | 935.43505 | 3618.7164 | 16076139.0000 | 19933272.0000 | 1.4647 | 1.4947 | Dimethyl (K); Dimethyl (N-term) |
| Q6F286 | | | 981.22591 | 3921.8574 | 14800271.0000 | 18497772.0000 | 0.4867 | 0.4780 | Dimethyl (K); Dimethyl (N-term) |
| Q6FC21 | | | 935.93764 | 3660.7467 | 10178794.0000 | 6814193.0000 | 0.8411 | 1.1115 | Dimethyl (K); Dimethyl (N-term) |

FIGURE 21 (continued)

SEQUENCE LISTING

```
<160> NUMBER OF SEQ ID NOS: 111

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
agaatacttg catagtgaca ggttacag                                28

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
gttatggcgg cggtggaggt c                                      21
```

```
<210> SEQ ID NO 3
<211> LENGTH: 70
<212> TYPE: DNA
<213> ORGANISM: Artificial Sequence
<220> FEATURE:
<223> OTHER INFORMATION: primer

<400> SEQUENCE: 3
caaaaagctt atataaaaac atacatacaa tctttgggga aaaggctatg attccgggga      60
tccgtcgacc                                                            70

<210> SEQ ID NO 4
<211> LENGTH: 70
<212> TYPE: DNA
<213> ORGANISM: Artificial Sequence
<220> FEATURE:
<223> OTHER INFORMATION: primer

<400> SEQUENCE: 4
ggattgacct ctcttttta tttctaaaat tacgatgcta caaatgattg tgtaggctgg       60
agctgcttcg                                                            70

<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5
gcgggatccg caaattggtg atgtgatgtc tcg                                  33

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
gcgggtaccg ctgcgaggaa taaaagaat act                                   33

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
gcgggatccg caaattggtg atgtgatgtc tcg                                  33

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
gcgggtacct cgtattgtga actagaccat cct                                  33

<210> SEQ ID NO 9
<211> LENGTH: 33
<212> TYPE: DNA
```

<213> ORGANISM: Artificial Sequence
<220> FEATURE:
<223> OTHER INFORMATION: primer

<400> SEQUENCE: 9
gcgggatccg caaattggtg atgtgatgtc tcg                33

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
gcgggtaccg ctgcgaggaa taaaaagaat act                33

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
agaatacttg catagtgaca ggttacag                      28

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
cgcatttata tttggggatt actc                          24

<210> SEQ ID NO 13
<211> LENGTH: 70
<212> TYPE: DNA
<213> ORGANISM: Artificial Sequence
<220> FEATURE:
<223> OTHER INFORMATION: primer

<400> SEQUENCE: 13
cttccatgta taattcttct caagtttttg gtctgtaacc tgtcactatg attccgggga   60
tccgtcgacc                                                         70

<210> SEQ ID NO 14
<211> LENGTH: 70
<212> TYPE: DNA
<213> ORGANISM: Artificial Sequence
<220> FEATURE:
<223> OTHER INFORMATION: primer

<400> SEQUENCE: 14
aaaatcccct tgaaaacaag gggatttttt tatttatctt ttaataattg tgtaggctgg   60
agctgcttcg                                                         70

<210> SEQ ID NO 15
<211> LENGTH: 44
<212> TYPE: DNA
<213> ORGANISM: Artificial Sequence
<220> FEATURE:
<223> OTHER INFORMATION: primer

```
<400> SEQUENCE: 15
cttcctcaat catttgtagc agcgtaattt tagaaataaa aaag         44

<210> SEQ ID NO 16
<211> LENGTH: 44
<212> TYPE: DNA
<213> ORGANISM: Artificial Sequence
<220> FEATURE:
<223> OTHER INFORMATION: primer

<400> SEQUENCE: 16 ctttttatt tctaaaatta cgctgctaca aatgattgag gaag          44

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
atgaaaaaac ttgagcacct tgc                                23

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
tgtttgctct tatttctact g                                  21

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
ttgtcattta taaagttagt cac                                23

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
tgtacacctg attttaatat tcta                               24

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
gaaataagag caaacaattc cggggatccg tcgacc                  36

<210> SEQ ID NO 22
```

```
<211> LENGTH: 35
<212> TYPE: DNA
<213> ORGANISM: Artificial Sequence
<220> FEATURE:
<223> OTHER INFORMATION: primer

<400> SEQUENCE: 22
ctttataaat gacaatgtag gctggagctg cttcg                              35

<210> SEQ ID NO 23
<211> LENGTH: 37
<212> TYPE: DNA
<213> ORGANISM: Artificial Sequence
<220> FEATURE:
<223> OTHER INFORMATION: primer set 12F

<400> SEQUENCE: 23
ctcaagtttt ttcatcgcca tggcggccgg gagcatg                            37

<210> SEQ ID NO 24
<211> LENGTH: 40
<212> TYPE: DNA
<213> ORGANISM: Artificial Sequence
<220> FEATURE:
<223> OTHER INFORMATION: primer set 12R

<400> SEQUENCE: 24
aaaatcaggt gtacaactag tgaattcgcg gccgcctgca                         40

<210> SEQ ID NO 25
<211> LENGTH: 18
<212> TYPE: DNA
<213> ORGANISM: Artificial Sequence
<220> FEATURE:
<223> OTHER INFORMATION: primer set 13F

<400> SEQUENCE: 25
cgtccccaaa agcgtgaa                                                 18

<210> SEQ ID NO 26
<211> LENGTH: 23
<212> TYPE: DNA
<213> ORGANISM: Artificial Sequence
<220> FEATURE:
<223> OTHER INFORMATION: primer set 13R

<400> SEQUENCE: 26
ttaggcaaat ttcgaagcgt gat                                           23

<210> SEQ ID NO 27
<211> LENGTH: 28
<212> TYPE: DNA
<213> ORGANISM: Artificial Sequence
<220> FEATURE:
<223> OTHER INFORMATION: primer set 14F

<400> SEQUENCE: 27
gcgcccggga taagtgctca attgatgg                                      28

<210> SEQ ID NO 28
<211> LENGTH: 25
<212> TYPE: DNA
<213> ORGANISM: Artificial Sequence
<220> FEATURE:
<223> OTHER INFORMATION: primer set 14R

<400> SEQUENCE: 28
```

```
ggtaccgaga tcccaaacca gcaac                                         25

<210> SEQ ID NO 29
<211> LENGTH: 25
<212> TYPE: DNA
<213> ORGANISM: Artificial Sequence
<220> FEATURE:
<223> OTHER INFORMATION: primer set 15F

<400> SEQUENCE: 29
actagtgaat tcgcggccgc ctgca                                         25

<210> SEQ ID NO 30
<211> LENGTH: 22
<212> TYPE: DNA
<213> ORGANISM: Artificial Sequence
<220> FEATURE:
<223> OTHER INFORMATION: primer set 15R

<400> SEQUENCE: 30
cgccatggcg gccgggagca tg                                            22

<210> SEQ ID NO 31
<211> LENGTH: 20
<212> TYPE: DNA
<213> ORGANISM: Artificial Sequence
<220> FEATURE:
<223> OTHER INFORMATION: primer set 16F

<400> SEQUENCE: 31
attccgggga tccgtcgacc                                               20

<210> SEQ ID NO 32
<211> LENGTH: 20
<212> TYPE: DNA
<213> ORGANISM: Artificial Sequence
<220> FEATURE:
<223> OTHER INFORMATION: primer set 16R

<400> SEQUENCE: 32
tgtaggctgg agctgcttcg                                               20

<210> SEQ ID NO 33
<211> LENGTH: 38
<212> TYPE: DNA
<213> ORGANISM: Artificial Sequence
<220> FEATURE:
<223> OTHER INFORMATION: primer set 17F

<400> SEQUENCE: 33
ccggccgcca tggcgatgac gattggttta attttttc                           38

<210> SEQ ID NO 34
<211> LENGTH: 40
<212> TYPE: DNA
<213> ORGANISM: Artificial Sequence
<220> FEATURE:
<223> OTHER INFORMATION: primer set 17R

<400> SEQUENCE: 34
acggatcccc ggaatcatac ttgtaaaaaa aaaagtattt                         40

<210> SEQ ID NO 35
<211> LENGTH: 40
<212> TYPE: DNA
```

<213> ORGANISM: Artificial Sequence
<220> FEATURE:
<223> OTHER INFORMATION: primer set 18F

<400> SEQUENCE: 35
cagctccagc ctacaatgga agaaaattct ttattaattt        40

<210> SEQ ID NO 36
<211> LENGTH: 37
<212> TYPE: DNA
<213> ORGANISM: Artificial Sequence
<220> FEATURE:
<223> OTHER INFORMATION: primer set 18R

<400> SEQUENCE: 36
cgcgaattca ctagtttaaa catattttc ccatttc        37

<210> SEQ ID NO 37
<211> LENGTH: 32
<212> TYPE: DNA
<213> ORGANISM: Artificial Sequence
<220> FEATURE:
<223> OTHER INFORMATION: primer set 19F

<400> SEQUENCE: 37
ccggccgcca tggcgatgac tcctgccgga gg        32

<210> SEQ ID NO 38
<211> LENGTH: 41
<212> TYPE: DNA
<213> ORGANISM: Artificial Sequence
<220> FEATURE:
<223> OTHER INFORMATION: primer set 19R

<400> SEQUENCE: 38
acggatcccc ggaatttaat aaagaatttt cttccattta c        41

<210> SEQ ID NO 39
<211> LENGTH: 41
<212> TYPE: DNA
<213> ORGANISM: Artificial Sequence
<220> FEATURE:
<223> OTHER INFORMATION: primer set 20F

<400> SEQUENCE: 39
cagctccagc ctacaatagt aggactaaaa aaatgatttc g        41

<210> SEQ ID NO 40
<211> LENGTH: 40
<212> TYPE: DNA
<213> ORGANISM: Artificial Sequence
<220> FEATURE:
<223> OTHER INFORMATION: primer set 20R

<400> SEQUENCE: 40
cgcgaattca ctagtttatt tatataaccc tttttctttc        40

<210> SEQ ID NO 41
<211> LENGTH: 40
<212> TYPE: DNA
<213> ORGANISM: Artificial Sequence
<220> FEATURE:
<223> OTHER INFORMATION: primer set 21F

<400> SEQUENCE: 41
cggccgccat ggcgatgttt aaaaatgtat taattactgg        40

<210> SEQ ID NO 42
<211> LENGTH: 40
<212> TYPE: DNA
<213> ORGANISM: Artificial Sequence
<220> FEATURE:
<223> OTHER INFORMATION: primer set 21R

<400> SEQUENCE: 42
acggatcccc ggaatcattt atttatataa ccctttttct                                40

<210> SEQ ID NO 43
<211> LENGTH: 40
<212> TYPE: DNA
<213> ORGANISM: Artificial Sequence
<220> FEATURE:
<223> OTHER INFORMATION: primer set 22F

<400> SEQUENCE: 43
cagctccagc ctacaataaa tttaaaatat tcataaatct                                40

<210> SEQ ID NO 44
<211> LENGTH: 40
<212> TYPE: DNA
<213> ORGANISM: Artificial Sequence
<220> FEATURE:
<223> OTHER INFORMATION: primer set 22R

<400> SEQUENCE: 44
cgcgaattca ctagtttata atttaagttc ttgaatcaac                                40

<210> SEQ ID NO 45
<211> LENGTH: 24
<212> TYPE: DNA
<213> ORGANISM: Artificial Sequence
<220> FEATURE:
<223> OTHER INFORMATION: primer set 23F

<400> SEQUENCE: 45
ctacattgtt tattttacc agaa                                                  24

<210> SEQ ID NO 46
<211> LENGTH: 22
<212> TYPE: DNA
<213> ORGANISM: Artificial Sequence
<220> FEATURE:
<223> OTHER INFORMATION: primer set 23R

<400> SEQUENCE: 46
gaagcttgaa gttatccacg aa                                                   22

<210> SEQ ID NO 47
<211> LENGTH: 26
<212> TYPE: DNA
<213> ORGANISM: Artificial Sequence
<220> FEATURE:
<223> OTHER INFORMATION: primer set 24F

<400> SEQUENCE: 47
catcaaaaat accagcctaa attatc                                               26

<210> SEQ ID NO 48
<211> LENGTH: 23
<212> TYPE: DNA
<213> ORGANISM: Artificial Sequence
<220> FEATURE:

<223> OTHER INFORMATION: primer set 24R

<400> SEQUENCE: 48
ccattgtttg aaattattta ggg                                    23

<210> SEQ ID NO 49
<211> LENGTH: 26
<212> TYPE: DNA
<213> ORGANISM: Artificial Sequence
<220> FEATURE:
<223> OTHER INFORMATION: primer set 25F

<400> SEQUENCE: 49
catcaaaaat accagcctaa attatc                                 26

<210> SEQ ID NO 50
<211> LENGTH: 25
<212> TYPE: DNA
<213> ORGANISM: Artificial Sequence
<220> FEATURE:
<223> OTHER INFORMATION: primer set 25R

<400> SEQUENCE: 50
gaagaaaatt ctttattaat ttctg                                  25

<210> SEQ ID NO 51
<211> LENGTH: 26
<212> TYPE: DNA
<213> ORGANISM: Artificial Sequence
<220> FEATURE:
<223> OTHER INFORMATION: primer set 26F

<400> SEQUENCE: 51
catcaaaaat accagcctaa attatc                                 26

<210> SEQ ID NO 52
<211> LENGTH: 24
<212> TYPE: DNA
<213> ORGANISM: Artificial Sequence
<220> FEATURE:
<223> OTHER INFORMATION: primer set 26R

<400> SEQUENCE: 52 gaaaagggt tatataaata aatg                                    24

<210> SEQ ID NO 53
<211> LENGTH: 33
<212> TYPE: DNA
<213> ORGANISM: Artificial Sequence
<220> FEATURE:
<223> OTHER INFORMATION: primer set 27F

<400> SEQUENCE: 53
gcgcccgggc tacattgttt atttttacca gaa                         33

<210> SEQ ID NO 54
<211> LENGTH: 33
<212> TYPE: DNA
<213> ORGANISM: Artificial Sequence
<220> FEATURE:
<223> OTHER INFORMATION: primer set 27R

<400> SEQUENCE: 54
gcgggtacca ccatcattga ctactaagac ctc                         33

<210> SEQ ID NO 55
<211> LENGTH: 33
<212> TYPE: DNA
<213> ORGANISM: Artificial Sequence
<220> FEATURE:
<223> OTHER INFORMATION: primer set 28F

<400> SEQUENCE: 55
gcgcccgggc tacattgttt atttttacca gaa                            33

<210> SEQ ID NO 56
<211> LENGTH: 31
<212> TYPE: DNA
<213> ORGANISM: Artificial Sequence
<220> FEATURE:
<223> OTHER INFORMATION: primer set 28R

<400> SEQUENCE: 56
gcgggtacct tctacatcca ataccagtcg t                              31

<210> SEQ ID NO 57
<211> LENGTH: 33
<212> TYPE: DNA
<213> ORGANISM: Artificial Sequence
<220> FEATURE:
<223> OTHER INFORMATION: primer set 29F

<400> SEQUENCE: 57
gcgcccgggc tacattgttt atttttacca gaa                            33

<210> SEQ ID NO 58
<211> LENGTH: 31
<212> TYPE: DNA
<213> ORGANISM: Artificial Sequence
<220> FEATURE:
<223> OTHER INFORMATION: primer set 29R

<400> SEQUENCE: 58
gcgggtaccg aagcttgaag ttatccacga a                              31

<210> SEQ ID NO 59
<211> LENGTH: 31
<212> TYPE: DNA
<213> ORGANISM: Artificial Sequence
<220> FEATURE:
<223> OTHER INFORMATION: primer set 30F

<400> SEQUENCE: 59
gcgcccgggc cgaagcaggg tgggtgttag t                              31

<210> SEQ ID NO 60
<211> LENGTH: 50
<212> TYPE: DNA
<213> ORGANISM: Artificial Sequence
<220> FEATURE:
<223> OTHER INFORMATION: primer set 30R

<400> SEQUENCE: 60
gcgggtacct tagtggtggt ggtggtgttg agctactgaa aactcaatac           50

<210> SEQ ID NO 61
<211> LENGTH: 36
<212> TYPE: DNA
<213> ORGANISM: Artificial Sequence
<220> FEATURE:
<223> OTHER INFORMATION: primer set 31F

<400> SEQUENCE: 61
gccatatggc ttatcaaaac tatattgcta aatctc    36

<210> SEQ ID NO 62
<211> LENGTH: 37
<212> TYPE: DNA
<213> ORGANISM: Artificial Sequence
<220> FEATURE:
<223> OTHER INFORMATION: primer set 31R

<400> SEQUENCE: 62
gcggatccct cttttttatt tctaaaatta cgatgct    37

<210> SEQ ID NO 63
<211> LENGTH: 33
<212> TYPE: DNA
<213> ORGANISM: Artificial Sequence
<220> FEATURE:
<223> OTHER INFORMATION: primer set 32F

<400> SEQUENCE: 63
ataggatcca tgaatgcaca aaagggtttt acc    33

<210> SEQ ID NO 64
<211> LENGTH: 48
<212> TYPE: DNA
<213> ORGANISM: Artificial Sequence
<220> FEATURE:
<223> OTHER INFORMATION: primer set 32R

<400> SEQUENCE: 64
tatgtcgact cagtggtggt ggtggtggtg accacgacat tctgatgg    48

<210> SEQ ID NO 65
<211> LENGTH: 34
<212> TYPE: DNA
<213> ORGANISM: Artificial Sequence
<220> FEATURE:
<223> OTHER INFORMATION: primer set 33F

<400> SEQUENCE: 65
atatggatcc gtggttgata gtagtactat atgg    34

<210> SEQ ID NO 66
<211> LENGTH: 61
<212> TYPE: DNA
<213> ORGANISM: Artificial Sequence
<220> FEATURE:
<223> OTHER INFORMATION: primer set 33R

<400> SEQUENCE: 66
atatgtcgac tcagtggtgg tggtggtggt gatattctat tgaacaaaat tttaacttag    60
g    61

<210> SEQ ID NO 67
<211> LENGTH: 40
<212> TYPE: DNA
<213> ORGANISM: Artificial Sequence
<220> FEATURE:
<223> OTHER INFORMATION: primer set 34F

<400> SEQUENCE: 67
atatggatcc gtggctggtt ccccgcgtgt gtataatagc    40

```
<210> SEQ ID NO 68
<211> LENGTH: 55
<212> TYPE: DNA
<213> ORGANISM: Artificial Sequence
<220> FEATURE:
<223> OTHER INFORMATION: primer set 34R

<400> SEQUENCE: 68
atatgtcgac ttagtggtgg tggtggtggt gcttggatga ctctacagca gaagc          55

<210> SEQ ID NO 69
<211> LENGTH: 35
<212> TYPE: DNA
<213> ORGANISM: Artificial Sequence
<220> FEATURE:
<223> OTHER INFORMATION: primer set 35F

<400> SEQUENCE: 69
actgggatcc atgttaaaaa aaattattct atttc                                35

<210> SEQ ID NO 70
<211> LENGTH: 64
<212> TYPE: DNA
<213> ORGANISM: Artificial Sequence
<220> FEATURE:
<223> OTHER INFORMATION: primer set 35R

<400> SEQUENCE: 70
actggtcgac taagtggtgg tggtggtggt ggtggtggtg gtgaggaatt tttgaggttg    60
gtac                                                                  64

<210> SEQ ID NO 71
<211> LENGTH: 31
<212> TYPE: DNA
<213> ORGANISM: Artificial Sequence
<220> FEATURE:
<223> OTHER INFORMATION: primer set 36F

<400> SEQUENCE: 71
actgggatcc atgcaagtat tctttctgtt c                                   31

<210> SEQ ID NO 72
<211> LENGTH: 65
<212> TYPE: DNA
<213> ORGANISM: Artificial Sequence
<220> FEATURE:
<223> OTHER INFORMATION: primer set 36R

<400> SEQUENCE: 72
actggtcgac taagtggtgg tggtggtggt ggtggtggtg gtgtttattt tttaacaact    60
ctgcc                                                                65

<210> SEQ ID NO 73
<211> LENGTH: 16
<212> TYPE: DNA
<213> ORGANISM: Artificial Sequence
<220> FEATURE:
<223> OTHER INFORMATION: primer set 37F

<400> SEQUENCE: 73
ggtggacgtg gaggag                                                    16

<210> SEQ ID NO 74
<211> LENGTH: 23
<212> TYPE: DNA
```

```
<213> ORGANISM: Artificial Sequence
<220> FEATURE:
<223> OTHER INFORMATION: primer set 37R

<400> SEQUENCE: 74
cttgcttggg ttacatcagt gct                                             23

<210> SEQ ID NO 75
<211> LENGTH: 20
<212> TYPE: DNA
<213> ORGANISM: Artificial Sequence
<220> FEATURE:
<223> OTHER INFORMATION: primer set 38F

<400> SEQUENCE: 75
aattattgta cagccttttg                                                 20

<210> SEQ ID NO 76
<211> LENGTH: 45
<212> TYPE: DNA
<213> ORGANISM: Artificial Sequence
<220> FEATURE:
<223> OTHER INFORMATION: primer set 38R

<400> SEQUENCE: 76
catcatcatc atcatcacta atattaaaaa tgtataaaaa acacc                     45

<210> SEQ ID NO 77
<211> LENGTH: 40
<212> TYPE: DNA
<213> ORGANISM: Artificial Sequence
<220> FEATURE:
<223> OTHER INFORMATION: primer set 39F

<400> SEQUENCE: 77
ccagttgaat tacttcctca agcatttgta gcatcgtaat                           40

<210> SEQ ID NO 78
<211> LENGTH: 40
<212> TYPE: DNA
<213> ORGANISM: Artificial Sequence
<220> FEATURE:
<223> OTHER INFORMATION: primer set 39R

<400> SEQUENCE: 78
attacgatgc tacaaatgct tgaggaagta attcaactgg                           40

<210> SEQ ID NO 79
<211> LENGTH: 27
<212> TYPE: PRT
<213> ORGANISM: Acinetobacter baylyi

<400> SEQUENCE: 79

Ser Ser Glu Leu Glu Asp Leu Phe Asn Ser Asp Gly Gly Ala Ala Ser
1               5                   10                  15

Glu Pro Ala Ala Ser Asp Lys Thr Ala Ala Lys
            20                  25

<210> SEQ ID NO 80
<211> LENGTH: 26
<212> TYPE: PRT
<213> ORGANISM: Acinetobacter baylyi

<400> SEQUENCE: 80

Lys Leu Ala Glu Pro Ala Ala Ser Ala Val Ala Asp Gln Asn Ser Pro
```

```
                1               5                   10                  15
Leu Ser Ala Gln Gln Gln Leu Glu Gln Lys
            20                  25

<210> SEQ ID NO 81
<211> LENGTH: 24
<212> TYPE: PRT
<213> ORGANISM: Acinetobacter baylyi

<400> SEQUENCE: 81

Ile Asp Ala Ala Ala Asp His Ala Ala Ala Ser Thr Glu His Ala Ala
1               5                   10                  15

Asp Lys Ala Glu Val Ala Thr Arg
            20

<210> SEQ ID NO 82
<211> LENGTH: 26
<212> TYPE: PRT
<213> ORGANISM: Acinetobacter baylyi

<400> SEQUENCE: 82

Ser Ala Ser Lys Pro Asn Val Glu Ala Ser Val Ser Ser Gln Asn Ala
1               5                   10                  15

Thr Leu Ser Ala Ser Gln Pro Gln His Gln
            20                  25

<210> SEQ ID NO 83
<211> LENGTH: 11
<212> TYPE: PRT
<213> ORGANISM: Acinetobacter baylyi

<400> SEQUENCE: 83

Ala Ala His Ala Ala Ser Ala Ala Ala Ser Lys
1               5                   10

<210> SEQ ID NO 84
<211> LENGTH: 12
<212> TYPE: PRT
<213> ORGANISM: Acinetobacter baylyi

<400> SEQUENCE: 84

Asp Ala Ala His Asp Ala Ala Ala Ser Val Glu Lys
1               5                   10

<210> SEQ ID NO 85
<211> LENGTH: 18
<212> TYPE: PRT
<213> ORGANISM: Acinetobacter baylyi

<400> SEQUENCE: 85

Ile Asp Ala Ala Ala Asp His Ala Ala Ala Ser Thr Glu His Ala Ala
1               5                   10                  15

Asp Lys

<210> SEQ ID NO 86
<211> LENGTH: 34
<212> TYPE: PRT
<213> ORGANISM: Acinetobacter baylyi

<400> SEQUENCE: 86

Ile Tyr Gln Asn Thr Asp Thr Ser Ser Ala Ala Ser Gln Thr Ser Ala
1               5                   10                  15
```

-continued

Ser Pro Thr Thr Gln Gly Leu Gly Asp Phe Leu His Ala Gln Glu Gln
            20                  25                  30

Leu Arg

<210> SEQ ID NO 87
<211> LENGTH: 13
<212> TYPE: PRT
<213> ORGANISM: Acinetobacter baylyi

<400> SEQUENCE: 87

Asn Thr Ala Ala Ser Ser Val Ala Ala Thr His Lys Lys
1               5                   10

<210> SEQ ID NO 88
<211> LENGTH: 26
<212> TYPE: PRT
<213> ORGANISM: Acinetobacter baylyi

<400> SEQUENCE: 88

Val Glu Gln Ile Val Ala Gln Pro Ala Pro Ala Ser Ser Val Gln Phe
1               5                   10                  15

Lys Pro Ser Asn Pro Glu Ile Asp Tyr Lys
            20                  25

<210> SEQ ID NO 89
<211> LENGTH: 33
<212> TYPE: DNA
<213> ORGANISM: Artificial Sequence
<220> FEATURE:
<223> OTHER INFORMATION: primer igrF

<400> SEQUENCE: 89
actggtcgac tagtagtact atatggcttt aaa                              33

<210> SEQ ID NO 90
<211> LENGTH: 38
<212> TYPE: DNA
<213> ORGANISM: Artificial Sequence
<220> FEATURE:
<223> OTHER INFORMATION: primer igrR

<400> SEQUENCE: 90
actgctgcag ttaatattct attgaacaaa attttaac                         38

<210> SEQ ID NO 91
<211> LENGTH: 18
<212> TYPE: PRT
<213> ORGANISM: Artificial Sequence
<220> FEATURE:
<223> OTHER INFORMATION: Mass Spec fragment

<400> SEQUENCE: 91

Asn Ser Gly Thr Asp Thr Pro Val Glu Leu Leu Pro Gln Ser Phe Val
1               5                   10                  15

Ala Ser

<210> SEQ ID NO 92
<211> LENGTH: 60
<212> TYPE: PRT
<213> ORGANISM: Artificial Sequence
<220> FEATURE:
<223> OTHER INFORMATION: Carboxy terminal fragment

<400> SEQUENCE: 92

Ile Ala Cys Thr Leu Gln Gly Ser Ala Thr Ile Gly Gly Val Leu
1               5                   10                  15

Thr Leu Thr Arg Ser Ala Asp Val Ala Ala Ser Gly Val Asn Ala
            20                  25                  30

Asn Val Gly Gly Trp Thr Cys Ser Ile Thr Lys Gly Thr Thr Asp Ile
        35                  40                  45

Ser Ser Val Ile Ala Pro Lys Gly Cys Thr Ile Ile
    50                  55                  60

<210> SEQ ID NO 93
<211> LENGTH: 48
<212> TYPE: PRT
<213> ORGANISM: Artificial Sequence
<220> FEATURE:
<223> OTHER INFORMATION: Carboxy terminal fragment

<400> SEQUENCE: 93

Ala Gly Gln Ile Ile Val Thr Met Asp Thr Thr Lys Ala Lys Gly Ala
1               5                   10                  15

Asn Ile Thr Leu Thr Pro Thr Tyr Ala Ser Gly Ala Val Thr Trp Lys
            20                  25                  30

Cys Thr Thr Thr Ser Asp Lys Lys Tyr Val Pro Ser Glu Cys Arg Gly
        35                  40                  45

<210> SEQ ID NO 94
<211> LENGTH: 49
<212> TYPE: PRT
<213> ORGANISM: Artificial Sequence
<220> FEATURE:
<223> OTHER INFORMATION: Carboxy terminal fragment

<400> SEQUENCE: 94

Ile Thr Tyr Thr Phe Lys Ser Ser Gly Val Ser Asn Lys Leu Thr Ser
1               5                   10                  15

Thr Lys Ile Val Met Asn Val Ser Glu Thr Gly Ile Leu Thr Lys Asn
            20                  25                  30

Ser Gly Thr Asp Thr Pro Val Glu Leu Leu Pro Gln Ser Phe Val Ala
        35                  40                  45

Ser

<210> SEQ ID NO 95
<211> LENGTH: 54
<212> TYPE: PRT
<213> ORGANISM: Artificial Sequence
<220> FEATURE:
<223> OTHER INFORMATION: Carboxy terminal fragment

<400> SEQUENCE: 95

Thr Val Glu Leu Val Ala Thr Leu Gly Lys Ser Ser Gly Ser Ala Ile
1               5                   10                  15

Lys Gly Ala Val Ile Thr Val Ser Arg Lys Asn Asp Gly Val Trp Asn
            20                  25                  30

Cys Lys Ile Thr Lys Thr Pro Thr Ala Trp Lys Pro Asn Tyr Ala Pro
        35                  40                  45

Ala Asn Cys Pro Lys Ser
    50

<210> SEQ ID NO 96
<211> LENGTH: 50
<212> TYPE: PRT
<213> ORGANISM: Artificial Sequence

```
<220> FEATURE:
<223> OTHER INFORMATION: Carboxy terminal fragment

<400> SEQUENCE: 96

Ile Thr Cys Thr Leu Lys Gly Thr Ser Gln Ile Asn Ser Lys Lys Ile
1               5                   10                  15

Glu Trp Arg Asp Ala Asp Asn Ala Thr Asn Gly Thr Thr Gly Ala Trp
            20                  25                  30

Arg Cys Lys Thr Asp Val Ala Glu Asn Leu Arg Pro Lys Ser Cys Gly
        35                  40                  45

Ala Ser
    50

<210> SEQ ID NO 97
<211> LENGTH: 49
<212> TYPE: PRT
<213> ORGANISM: Artificial Sequence
<220> FEATURE:
<223> OTHER INFORMATION: Carboxy terminal fragment

<400> SEQUENCE: 97

Ile Thr Tyr Thr Phe Lys Ser Ser Gly Val Ser Thr Lys Leu Thr Ser
1               5                   10                  15

Lys Gln Ile Val Met Asn Val Ser Glu Thr Gly Ile Leu Thr Lys Asn
            20                  25                  30

Ser Ser Thr Asn Ala Pro Ala Glu Leu Leu Pro Gln Ser Phe Thr Ala
        35                  40                  45

Ser

<210> SEQ ID NO 98
<211> LENGTH: 50
<212> TYPE: PRT
<213> ORGANISM: Artificial Sequence
<220> FEATURE:
<223> OTHER INFORMATION: Carboxy terminal fragment

<400> SEQUENCE: 98

Ile Thr Cys Thr Leu Lys Gly Thr Ser Gln Ile Asn Gly Lys Lys Ile
1               5                   10                  15

Glu Trp Arg Asp Ala Asp Asn Ala Thr Asn Gly Thr Thr Gly Ala Trp
            20                  25                  30

Arg Cys Lys Thr Asp Val Ala Glu Ser Leu Arg Pro Lys Ser Cys Gly
        35                  40                  45

Ala Ser
    50

<210> SEQ ID NO 99
<211> LENGTH: 50
<212> TYPE: PRT
<213> ORGANISM: Artificial Sequence
<220> FEATURE:
<223> OTHER INFORMATION: Carboxy terminal fragment

<400> SEQUENCE: 99

Ile Thr Cys Thr Leu Lys Gly Thr Ser Gln Ile Asn Gly Lys Lys Ile
1               5                   10                  15

Glu Trp Arg Asp Ala Asp Asn Ala Thr Asn Gly Thr Thr Gly Ala Trp
            20                  25                  30
```

Arg Cys Lys Thr Asp Val Ala Glu Asn Leu Arg Pro Lys Ser Cys Gly
            35                  40                  45

Ala Ser
    50

<210> SEQ ID NO 100
<211> LENGTH: 50
<212> TYPE: PRT
<213> ORGANISM: Artificial Sequence
<220> FEATURE:
<223> OTHER INFORMATION: Carboxy terminal fragment

<400> SEQUENCE: 100

Ile Thr Cys Thr Leu Lys Gly Thr Ser Gln Ile Asn Gly Lys Lys Ile
1               5                   10                  15

Glu Trp Arg Asp Ala Asp Asn Ala Thr Asn Gly Thr Thr Gly Ala Trp
            20                  25                  30

Arg Cys Lys Thr Asp Val Ala Glu Asn Leu Arg Pro Lys Ser Cys Gly
            35                  40                  45

Ala Ser
    50

<210> SEQ ID NO 101
<211> LENGTH: 50
<212> TYPE: PRT
<213> ORGANISM: Artificial Sequence
<220> FEATURE:
<223> OTHER INFORMATION: Carboxy terminal fragment

<400> SEQUENCE: 101

Ile Thr Cys Thr Leu Lys Gly Thr Ser Gln Ile Asn Ser Lys Lys Ile
1               5                   10                  15

Glu Trp Arg Asp Ala Asp Asn Ala Thr Asn Gly Thr Thr Gly Ala Trp
            20                  25                  30

Arg Cys Lys Thr Asp Val Ala Glu Asn Leu Arg Pro Lys Ser Cys Gly
            35                  40                  45

Ala Ser
    50

<210> SEQ ID NO 102
<211> LENGTH: 50
<212> TYPE: PRT
<213> ORGANISM: Artificial Sequence
<220> FEATURE:
<223> OTHER INFORMATION: Carboxy terminal fragment

<400> SEQUENCE: 102

Ile Thr Cys Thr Leu Lys Gly Thr Ser Gln Ile Asn Gly Lys Lys Ile
1               5                   10                  15

Glu Trp Arg Asp Ala Asp Asn Ala Thr Asn Gly Thr Thr Gly Ala Trp
            20                  25                  30

Arg Cys Lys Thr Asp Val Ala Asp Asn Leu Arg Pro Lys Ser Cys Gly
            35                  40                  45

Ala Ser
    50

<210> SEQ ID NO 103
<211> LENGTH: 51
<212> TYPE: PRT
<213> ORGANISM: Artificial Sequence
<220> FEATURE:
<223> OTHER INFORMATION: Carboxy terminal fragment

<400> SEQUENCE: 103

Ile Thr Cys Thr Leu Lys Gly Thr Ser Gln Ile Asn Gly Lys Lys Ile
1               5                   10                  15

Gln Trp Val Arg Ala Ala Asp Asn Ala Thr Asn Gly Thr Thr Gly Thr
            20                  25                  30

Trp Ser Cys Ile Thr Asp Val Ala Asp Asn Leu Arg Pro Lys Ser Cys
        35                  40                  45

Gly Ala Ser
    50

<210> SEQ ID NO 104
<211> LENGTH: 49
<212> TYPE: PRT
<213> ORGANISM: Artificial Sequence
<220> FEATURE:
<223> OTHER INFORMATION: Carboxy terminal fragment

<400> SEQUENCE: 104

Ile Thr Tyr Thr Phe Lys Ser Ser Gly Val Ser Asn Lys Leu Thr Ser
1               5                   10                  15

Lys Lys Ile Gly Met Asn Val Ser Glu Thr Gly Ile Leu Thr Lys Asn
            20                  25                  30

Ser Asp Thr Asp Thr Pro Ala Glu Leu Leu Pro Gln Ser Phe Thr Ala
        35                  40                  45

Ser

<210> SEQ ID NO 105
<211> LENGTH: 21
<212> TYPE: PRT
<213> ORGANISM: Artificial Sequence
<220> FEATURE:
<223> OTHER INFORMATION: Mass spectometry fragment

<400> SEQUENCE: 105

Ala Ala Ser Gly Val Glu Ala Ala Ala Pro Ala Thr Leu Thr Leu
1               5                   10                  15

Ser Thr Asp Asp Lys
            20

<210> SEQ ID NO 106
<211> LENGTH: 12
<212> TYPE: PRT
<213> ORGANISM: Artificial Sequence
<220> FEATURE:
<223> OTHER INFORMATION: Mass spectometry fragments

<400> SEQUENCE: 106

Asp Ala Ala His Asp Ala Ala Ala Ser Val Glu Lys
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Mass spectometry fragment

<400> SEQUENCE: 107

Asn Thr Ala Ala Ser Ser Val Ala Ala Thr His Lys Lys
1               5                   10

```
<210> SEQ ID NO 108
<211> LENGTH: 26
<212> TYPE: PRT
<213> ORGANISM: Artificial Sequence
<220> FEATURE:
<223> OTHER INFORMATION: Mass spectometry fragment

<400> SEQUENCE: 108

Lys Leu Ala Glu Pro Ala Ala Ser Ala Val Ala Asp Gln Asn Ser Pro
1               5                   10                  15

Leu Ser Ala Gln Gln Gln Leu Glu Gln Lys
            20                  25

<210> SEQ ID NO 109
<211> LENGTH: 16
<212> TYPE: PRT
<213> ORGANISM: Artificial Sequence
<220> FEATURE:
<223> OTHER INFORMATION: Mass spectometry fragment

<400> SEQUENCE: 109

Ala Gln Ser Val Ala Asn Tyr Leu Ser Gly Gln Val Ser Ser Ser Arg
1               5                   10                  15

<210> SEQ ID NO 110
<211> LENGTH: 5
<212> TYPE: PRT
<213> ORGANISM: Artificial Sequence
<220> FEATURE:
<223> OTHER INFORMATION: Consensus sequon
<220> FEATURE:
<221> NAME/KEY: MISC_FEATURE
<222> LOCATION: (1)..(1)
<223> OTHER INFORMATION: X is D or E
<220> FEATURE:
<221> NAME/KEY: MISC_FEATURE
<222> LOCATION: (2)..(2)
<223> OTHER INFORMATION: X is any amino acid except P
<220> FEATURE:
<221> NAME/KEY: MISC_FEATURE
<222> LOCATION: (4)..(4)
<223> OTHER INFORMATION: X is any amino acid except P
<220> FEATURE:
<221> NAME/KEY: MISC_FEATURE
<222> LOCATION: (5)..(5)
<223> OTHER INFORMATION: X is S or T

<400> SEQUENCE: 110

Xaa Xaa Asn Xaa Xaa
1               5

<210> SEQ ID NO 111
<211> LENGTH: 5
<212> TYPE: PRT
<213> ORGANISM: Artificial Sequence
<220> FEATURE:
<223> OTHER INFORMATION: Sequon

<400> SEQUENCE: 111

Asp Gln Asn Ala Thr
1               5
```

ACINETOBACTER O-OLIGOSACCHARYLTRANSFERASES AND USES THEREOF

CROSS-REFERENCE TO RELATED APPLICATIONS

This is a Continuation of U.S. National Phase application Ser. No. 15/553,733, filed Aug. 25, 2017, which claims the benefit of International Application No. PCT/CA2016/050208, Filed Feb. 26, 2016, which claims the benefit of U.S. Provisional Application Ser. No. 62/121,439, filed Feb. 26, 2015, all of which are incorporated herein by reference in their entireties.

INCORPORATION OF SEQUENCE LISTING

A Sequence Listing is contained in the file named "64100_186787_SEQLIST_ST25.txt" which is 27,776 bytes (measured in MS-Windows) and comprising 111 nucleic acid sequences, created Sep. 7, 2018, is electronically filed herewith and is incorporated herein by reference in its entirety.

FIELD

The present application pertains to the field of molecular microbiology. More particularly, the present application relates to O-oligosaccharyltransferases, particularly the use of $PglL_{ComP}$ O-oligosaccharyltransferase in vaccine applications.

BACKGROUND

*Acinetobacter baumannii* and *A. nosocomialis* are clinically relevant members of the *Acinetobacter calcoaceticus-A. baumannii* (Acb) complex and important opportunistic nosocomial pathogens (Wisplinghoff et al., 2012). These species have emerged as troublesome pathogens due in part to their remarkable resistance to disinfection, desiccation, as well as their ability to acquire multiply drug resistant phenotypes, all of which promote their survivability in the hospital setting. Furthermore, pan-resistant strains within the Acb are continuously being isolated from hospitals worldwide (Arroyo et al., 2009; Gottig et al., 2014). While the mechanisms of antibiotic resistance of Acb members has been intensively studied (Gordon et al., 2010), our understanding of their virulence mechanisms is unclear. Identified virulence factors include an outer membrane protein A (OmpA), the ability to form biofilms, exopolysaccharide, lipopolysaccharide (LPS), protein glycosylation systems and capsule (Choi et al., 2008; Choi et al., 2009; Gordon et al., 2010; Iwashkiw et al., 2012; Lees-Miller et al., 2013). A type VI secretion system (T6SS) has been also identified, although a role in pathogenesis has not been demonstrated (Carruthers et al., 2013; Weber et al., 2013).

*A. baylyi* is a non-pathogenic member of the genus *Acinetobacter*, characterized by its genetic tractability and natural competence. For these properties, *A. baylyi* is widely used as a model organism for molecular and genetic studies of the genus *Acinetobacter* (Vaneechoutte et al., 2006; de Berardinis et al., 2008; Brzoska et al., 2013) and is also utilized in bioremediation (Abd-El-Haleem et al., 2002; Mara et al., 2012). All members of the *Acinetobacter* genus, independent of their pathogenicity, carry a protein glycosylation system (Iwashkiw et al., 2012).

Protein glycosylation, the covalent attachment of carbohydrate moieties to protein substrates, is the most abundant post-translational modification of proteins (Varki, 1993) and occurs in all domains of life (Neuberger, 1938; Sleytr, 1975; Mescher & Strominger, 1976). The major types of protein glycosylation are N- and O-glycosylation. Both processes can be classified as oligosaccharyltransferase (OTase)-dependent and OTase independent (Nothaft & Szymanski, 2010; Iwashkiw et al., 2013). OTases are enzymes that catalyze the transfer of a glycan, previously assembled by cytoplasmic glycosyltransferases (GT) onto an undecaprenyl pyrophosphate lipid carrier, to target proteins. The development of sensitive analytical techniques has led to the identification of OTase-dependent protein glycosylation in numerous bacterial species. These include members of the genera *Campylobacter, Neisseria, Pseudomonas, Francisella, Vibrio, Burkholderia* and *Bacteroides* (Szymanski et al., 1999; Faridmoayer et al., 2007; Egge-Jacobsen et al., 2011; Balonova et al., 2012; Gebhart et al., 2012; Coyne et al., 2013; Lithgow et al., 2014). Glycosylation frequently affects protein stability, bacterial adhesion, flagellar filament assembly, biofilm formation, and virulence in general (Logan, 2006; Iwashkiw et al., 2013). An OTase-dependent, ubiquitous O-linked protein glycosylation system has been recently discovered within the genus *Acinetobacter*. This system was required for biofilm formation and pathogenicity of *A. baumannii* (Iwashkiw et al., 2012). The glycan structures for several strains of *A. baumannii* have also been characterized and extensive carbohydrate diversity has been established (Scott et al., 2014).

OTases involved in O-glycosylation (O-OTases) do not share extensive primary amino acid sequence homologies; yet, all O-Otases contain domains from the Wzy_C superfamily (Power and Jennings, 2003). Orthologs of PglL general 90 O-Otases and WaaL O-antigen ligases are two of the most well characterized enzymes from the Wzy_C superfamily. It has proven challenging to identify O-OTases based solely on bioinformatic methodologies as O-OTases and WaaL ligases catalyze similar reactions, i.e. the transfer of lipid-linked glycans to acceptor proteins or lipid A respectively (Hug & Feldman, 2011). The two enzymes appear to be evolutionarily and mechanistically related as mutagenesis of topologically similar conserved histidine residues of the *E. coli* O-antigen ligase (H337) and *N. meningitidis* O-OTase (H349) results in the loss of glycan transfer activities (Perez et al., 2008; Ruan et al., 2012; Musumeci et al., 2014). Recently, the PglL_A and PglL_B hidden Markov models (HMM) were defined to better resolve orthologs of PglL O-OTases from other enzymes of the Wzy_C superfamily (Power et al., 2006; Schulz et al., 2013).

O-OTases are often encoded downstream of their cognate target protein. This genetic arrangement is often found in Gram-negative organisms encoding type IV pili (Tfp) systems, where the major pilin subunit gene is immediately 5' of the cognate OTase gene (Schulz et al., 2013). For example, in *P. aeruginosa* strain 1244 the major pilin, PilA, is glycosylated by PilO (later renamed TfpO), an O-OTase encoded immediately downstream of pilA (Castric, 1995; Kus et al., 2004). This modification is believed to play a role in virulence as glycosylation-deficient mutants showed decreased twitching motility and were out-competed by the wild type in a mouse respiratory infection model (Kus et al., 2004; Smedley et al., 2005). The same genetic arrangement and glycosylation phenotype has also been found in *P. syringae* (Nguyen et al., 2012).

Pilin post-translational modification has also been identified in *Acinetobacter* species. In *A. baylyi* ADP1, two Wzy_C superfamily domain-containing proteins are encoded in the genome. One gene is found immediately downstream of the gene encoding the pilin-like protein ComP, whereas the other gene is found within a distant glycan biosynthesis gene cluster. Mutation of the predicted OTase encoded downstream of the comP gene affected the electrophoretic mobility of ComP, indicating this gene may encode for a ComP-specific OTase (Porstendorfer et al., 2000; Schulz et al., 2013). Additionally, during the course of a previous study demonstrating the functional production of Tfp by the medically relevant *A. nosocomialis* strain M2, we also identified two molecular forms of PilA differing by apparent molecular weight leading to the hypothesis that the pilins of Acb members may also be post-translationally modified (Harding et al., 2013; Carruthers et al., 2013).

OTases are powerful tool for glycoengineering conjugate vaccines. The enzymatic attachment of glycans to proteins present several advantages compared to the chemical attachment of sugars. Although they exhibit relaxed specificity, OTases known so far present some limitations. For example, glycans containing glucose at the reducing end have not been successfully transferred by any of the known enzymes, such as PglB and PglL. PglB has been shown to required an acetylated sugar at the reducing end (Wacker et al., 2006). PglL was able to transfer sugars with galactose at the reducing end (Faridmoayer et al., 2008), but it has not been shown that sugars containing a glucose at the reducing can be transferred to proteins. This is extremely important for the synthesis of vaccines against *Streptococcus*. Most capsular polysaccharides from *Streptococcus* contain a glucose residue at the reducing end (Bentley et al., 2006). The licensed vaccines against *S. pneumoniae*, such as Prevnar 13, contain up to 13 capsular serotypes. Better vaccines, containing more serotypes are needed. The current OTases have not been useful in generating conjugates containing capsule from these bacteria containing glucose at the reducing end, and therefore they have little applications for production of vaccines against *Streptococcus*.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide the use of an O-OTase for the generation of glycoproteins for vaccine applications.

In accordance with one aspect of the present invention, there is provided a method of synthesizing a glycoprotein comprising glycosylation of ComP using a $PglL_{ComP}$ O-oligosaccharyltransferase. The method can be performed in Gram negative bacteria, such as *Acinetobacter* (including, for example, *A. baylyi, A. baumannii, A. nosocomialis*, or *A. calcoaceticus*) or *E. coli*, and the like. The glycosylation can use sugars derived from O-glycosylation, N-glycans, O antigens, capsular polysaccharides, etc. In one particular embodiment, the N-glycan is derived from *Campylobacter*, such as *Campylobacter jejuni* N-hepatasaccharide, for example. Unlike previously known OTases, $PglL_{ComP}$ can be employed to efficiently attach capsular polysaccharides containing glucose at the reducing end to a protein carrier. Such capsules are common within the genus *Streptococcus*.

The present application provides the generation of an immune response in mice employing a glycoprotein obtained through the activity of $PglL_{ComP}$, containing a capsule from *S. pneumoniae* attached to a suitable carrier. In another embodiment, the ComP can be optionally fused to a second protein, an adjuvant or a carrier. In another aspect of the present invention there is provided a use of $PglL_{ComP}$ for the glycosylation of a protein, such as a protein with a *Streptococcus* capsule, in particular wherein the *Streptococcus* is *Streptococcus pneumoniae*.

In accordance with another aspect of the present invention there is provided an O-oligosaccharyltransferase (O-OTase) for glycosylation of ComP. The glycosylation can be recombinantly produced in Gram negative bacteria, such as *Acinetobacter* (including, for example, *A. baylyi, A. baumannii, A. nosocomialis*, or *A. calcoaceticus*) or *E. coli*, and the like. The glycosylation can use sugars derived from O-glycosylation, N-glycans, O-antigens, capsular polysaccharides, etc. In one particular embodiment, the N-glycan is derived from *Campylobacter*, such as *Campylobacter jejuni* N-hepatasaccharide or a capsular polysaccharide from *Streptococcus*, for example. In one particular embodiment, the O-OTase is $PglL_{ComP}$. In another embodiment, the capsular polysaccharide is a *Streptococcus* capsule, such as *Streptococcus pneumoniae*. Thus, the present application provides a vaccine against *Streptococcus*, more particularly *Streptococcus pneumoniae*.

In accordance with a further aspect of the present invention, there is provided a vaccine comprising a glycoprotein synthesized in accordance with the method as described herein.

In accordance with yet a further aspect of the present invention, there is provided a glycoprotein which is a fusion protein comprising ComP or a fragment of ComP carrying a glycosylation site.

BRIEF DESCRIPTION OF THE FIGURES

For a better understanding of the present invention, as well as other aspects and further features thereof, reference is made to the following description which is to be used in conjunction with the accompanying drawings, where:

FIG. 2 illustrates PilAM2 glycosylation in a TfpO-dependent manner with a tetrasaccharide containing (HexNAc)2, Hexose and N-acetyl-deoxyHexose. (A) Surface proteins from the indicated strains were prepared by shearing, as described in the materials and methods, followed by separation by SDS-PAGE and western blot analysis of whole cell lysates. PilAM2 from strain M2 was identified employing rabbit anti-PilAM2. PilAM2 from the M2ΔtfpO::kan mutant existed only as a lower molecular form indicating TfpO was required for PilAM2 post-translational modification. Strains M2 pilA+ and M2 tfpO+ were complemented pilA and tfpO mutants, respectively. "Gly" denotes the glycosylated form of the protein. (B) PilAM2 was sheared from the surface of strain M2 and a hyper-piliated mutant, precipitated, separated by SDS-PAGE, and visualized by Coomassie straining.

Bands associated with PilAM2 were excised and tryptically digested for MS/MS analysis. NSGTDTPVELLPQSFVAS (SEQ ID NO: 91).

Figure 3:
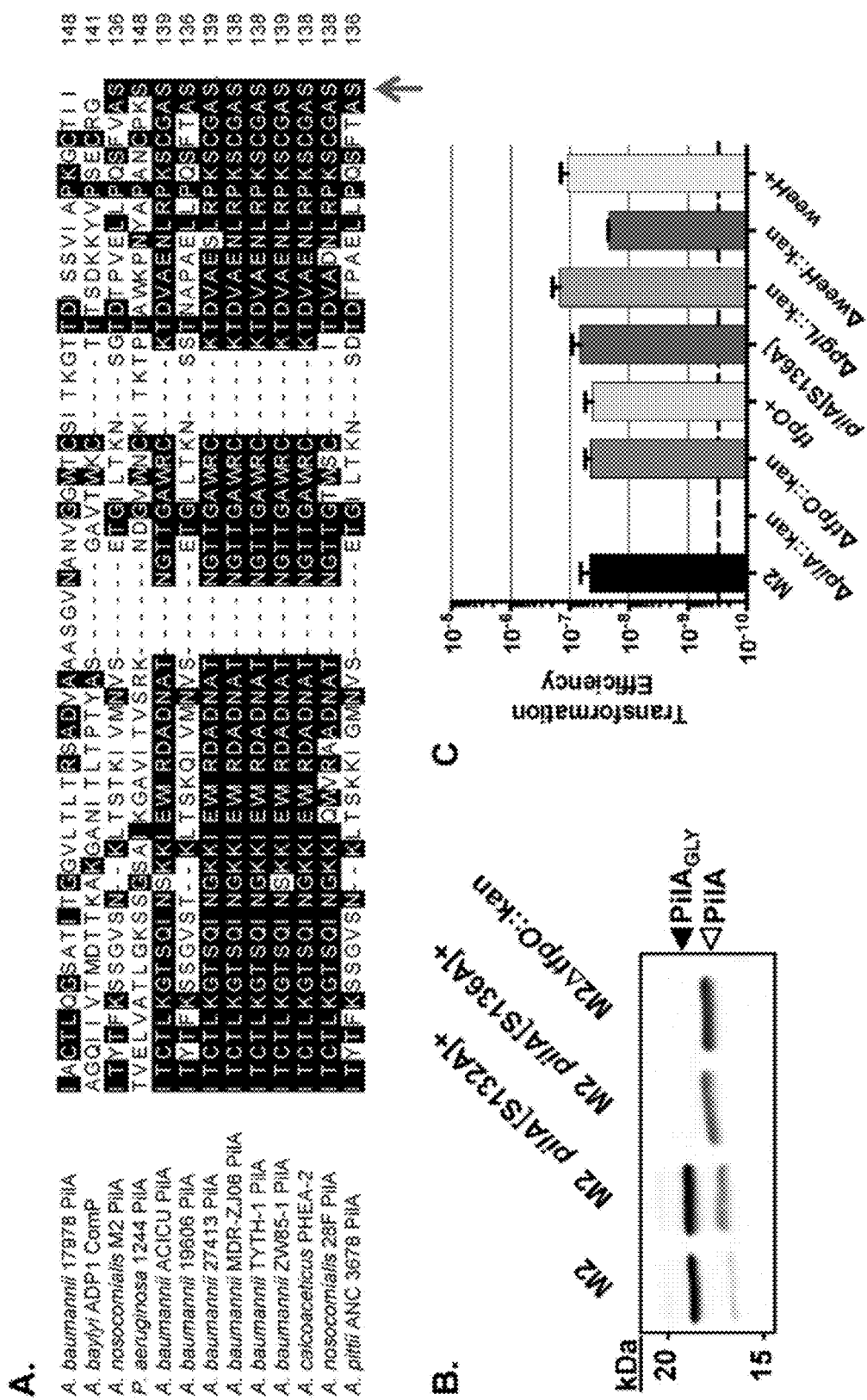

FIG. 3 illustrates PilAM2-like glycosylation dependency on a conserved carboxy-terminal serine. (A) Alignment of the carboxy terminal region of PilA proteins from *P. aeruginosa* strain 1244 and selected *Acinetobacter* strains (consecutively, SEQ ID Nos. 92-104). All *Acinetobacter* strains encoding tfpO homologs contain a carboxy-terminal serine on their respective PilA proteins. (B) Western blot analysis of whole cell extracts probing for PilAM2 expression and electrophoretic mobility. Strain M2 derivatives expressing PilA[S132A] and PilA[S136A] were constructed and extracts characterized. Serine 132 was not required for glycosylation while serine 136, the C-terminal serine was required for glycosylation. (C) Pilin glycosylation in strain M2 is not required for natural transformation. Mutants that were unable to glycosylate PilAM2 were still naturally transformable.

Figure 4:
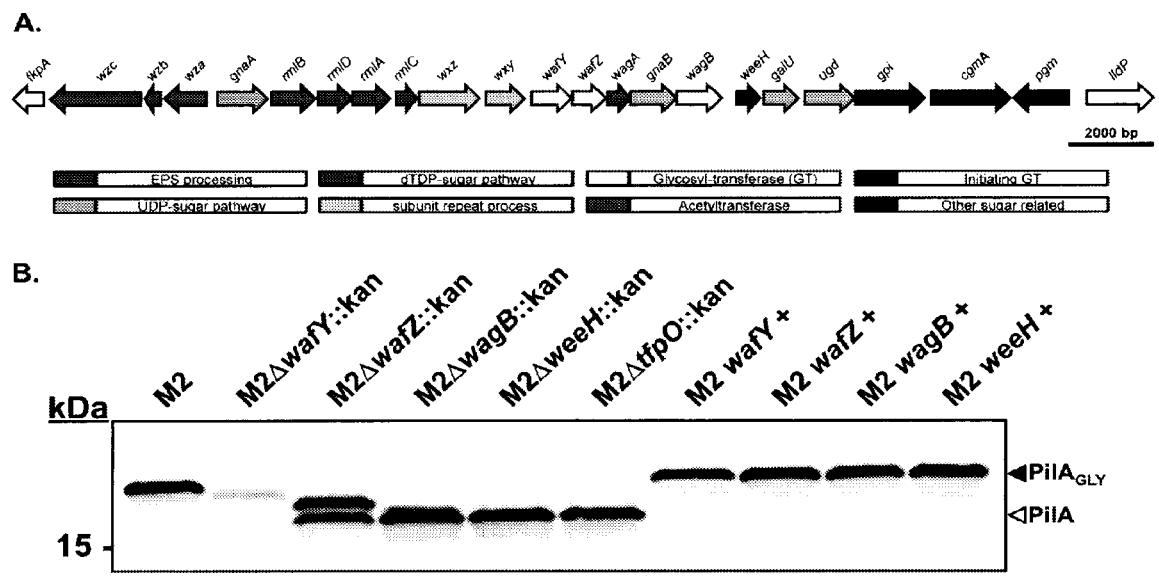

FIG. 4 illustrates that the major polysaccharide antigen locus (MPA) was required for pilin glycosylation. (A) Genetic organization of the strain M2 MPA locus which is located between the conserved fkpA and lldP genes. Adapted from Hu et al., 2013. (B) Western blot analysis of whole cell extracts probing for PilAM2 expression and electrophoretic mobility from MPA locus mutants. PilAM2 from the ΔweeH::kan mutant ran at the same electrophoretic mobility as PilAM2 from the tfpO::kan mutant indicating it was not glycosylated. Deletion of the other three glycosyltransferases yielded PilAM2 proteins with intermediate electrophoretic mobilities. PilA from the wafY::kan mutant migrated closest to the WT PilA mobility, then PilA from the wafZ::kan mutant, followed by PilA from the wagB::kan mutant. Mutants that were complemented all glycosylated PilAM2.

FIG. 5 illustrates that PglLM2 is a general O-OTase and utilizes the same lipid-linked glycan donor as TfpOM2. (A) Western blot analysis of whole cell extracts probing for OmpA-His expression and electrophoretic mobility. OmpA-His served as bait protein for glycosylation by strain M2 as well as the isogenic tfpOM2::kan and pglLM2::kan mutants. All strains expressed OmpA-His; however, OmpA-His from the pglLM2::kan mutant ran at an increased electrophoretic mobility indicating the lack of glycosylation. (B) Glycosylated OmpA-His was purified from solubilized membranes using nickel affinity chromatography, separated by SDS-PAGE, and visualized by Coomassie staining OmpA-His was excised from the gel and characterized by MS/MS analysis. AASGVEAAAAPATLTLSTDDK (SEQ ID NO: 105).

Figure 6:
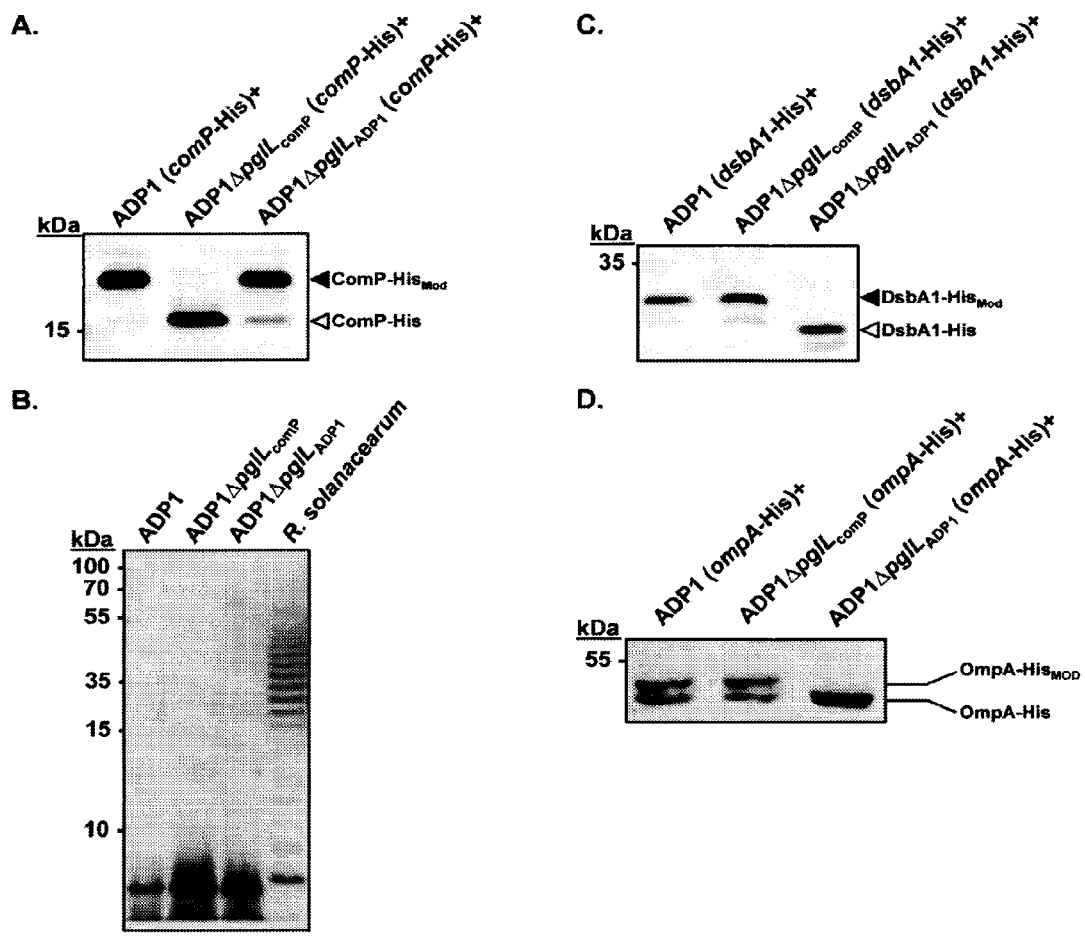

FIG. 6 illustrates activity of O-OTases in *A. baylyi* ADP1. (A) Western blot probing for ComP-His expression in whole cell lysates of *A. baylyi* ADP1 as well as the isogenic $\Delta pglL_{ComP}$ and $\Delta pglL_{ADP1}$ mutants. The increase in ComP-His electrophoretic mobility seen in the $\Delta pglL_{ComP}$ mutant indicates the absence of pilin glycosylation in this strain. (B) Silver stain of LPS obtained from *A. baylyi* ADP1, the isogenic $\Delta pglL_{ComP}$, and $\Delta pglL_{ADP1}$ mutants as well as *Ralstonia solanacearum*. *A. baylyi* lacks O-antigen, as seen by the lack of laddering observed with *R. solanacearum* LPS. (C, D) Western blot analysis of whole cell lysates from *A. baylyi* ADP1, the isogenic $\Delta pglL_{ComP}$ and $\Delta pglL_{ADP1}$ mutants recombinantly expressing his-tagged proteins Dsba1 (C) or OmpA-His (D). The increases in the relative mobility of the His-tagged proteins produced in the $\Delta pglL_{ADP1}$ background indicate that expression of $PglL_{ADP1}$ was required for glycosylation of these proteins.

Figure 7:
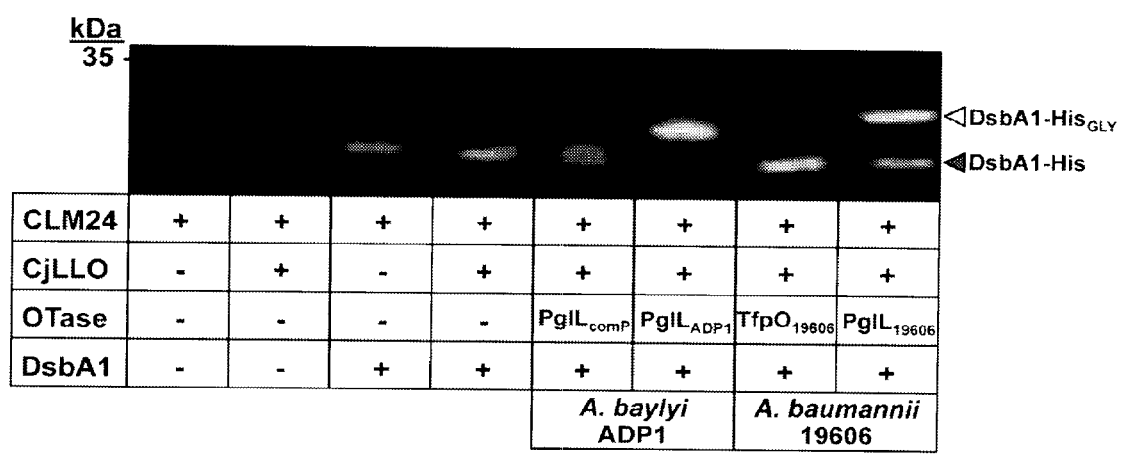

FIG. 7 illustrates the heterologous expression of TfpO and PglL OTases in *E. coli*. Western blot analysis of whole cell lysates of *E. coli* CLM24 expressing, as indicated, the *C. jejuni* lipid linked oligosaccharide (CjLLO) and His-tagged DsbA1 together with an *A. baylyi* or *A. baumannii* ATCC 19606 OTase. His-tagged DsbA1 was detected using the polyclonal anti-his antibody (green) and CjLLO was detected using the hR6 antibody (red). Co-localization of both signals, seen in yellow, indicates glycosylation of DsbA1 by the *Campylobacter* oligosaccharide. This is seen only when $PglL_{ADP1}$ or $PglL_{19606}$ were expressed in *E. coli* CLM24 along with CjLLO and His-tagged DsbA1.

Figure 8:
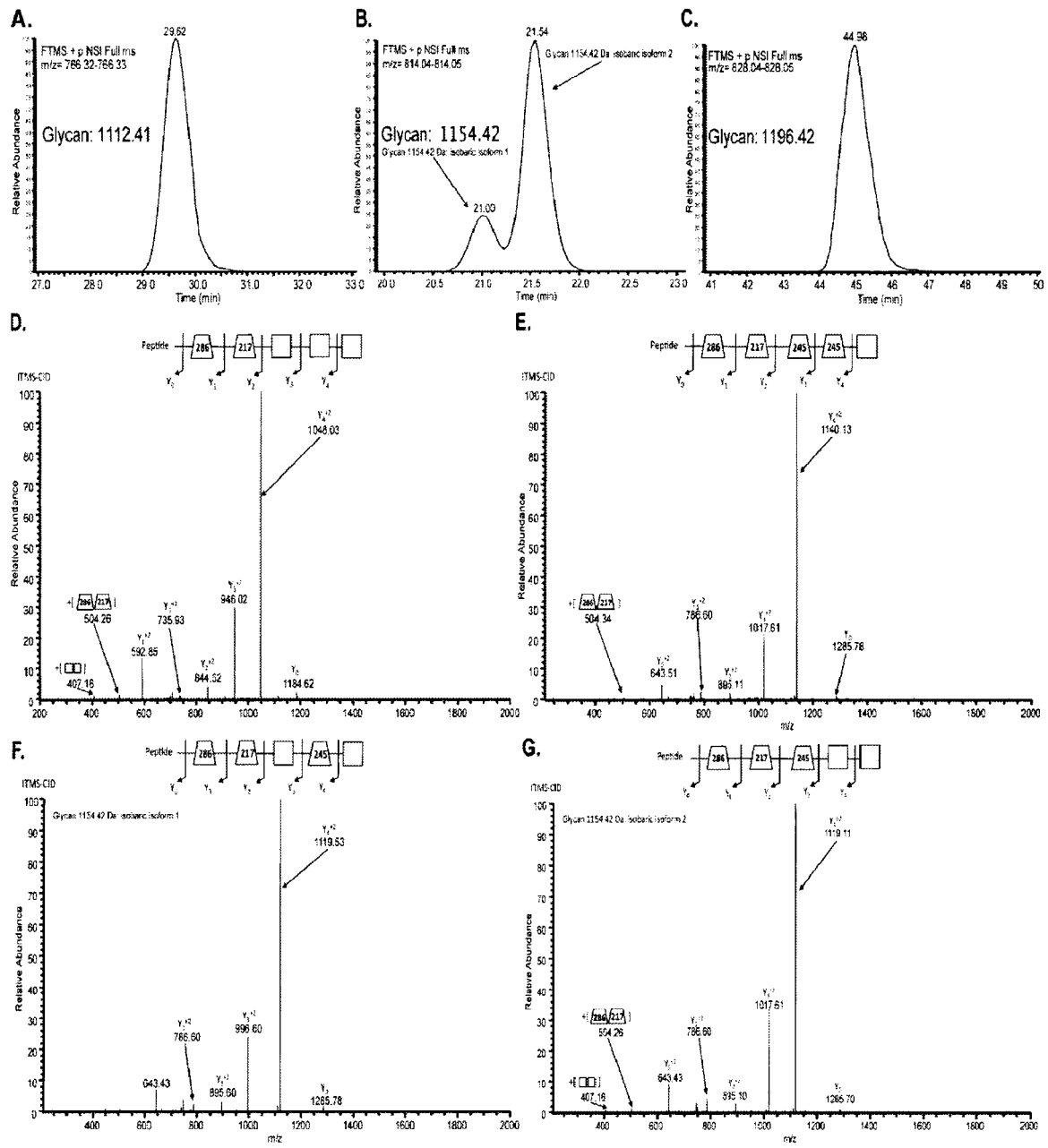

FIG. 8 provides an O-glycan structure identified using ZIC-HILIC enrichment of *A. baylyi* ADP1 glycoproteins. ITMS-CID fragmentation results in near exclusive glycan fragmentation of *A. baylyi* ADP1 glycopeptides enabling the identification of four unique glycans on multiple protein substrates corresponding to; A and D) a pentasaccharide composed of 286-217-HexNAc3 (1112.41 Da, 92DAAHDAAASVEK 103 (SEQ ID NO: 106) of Q6FCV1_ACIAD); B, F and G) two isobaric glycoforms composed of 286-217-245-HexNAc2 and 286-217-HexNAc-245-HexNAc (1154.41 Da, 344NTAASSVAATHKK356 (SEQ ID NO: 107) of Q6F814_ACIAD) and C and E) a pentasaccharide composed of 286-217-2452-HexNAc (1196.41 Da, 344NTAASSVAATHKK356 (SED ID NO: 107) of Q6F814_ACIAD).

Figure 9:
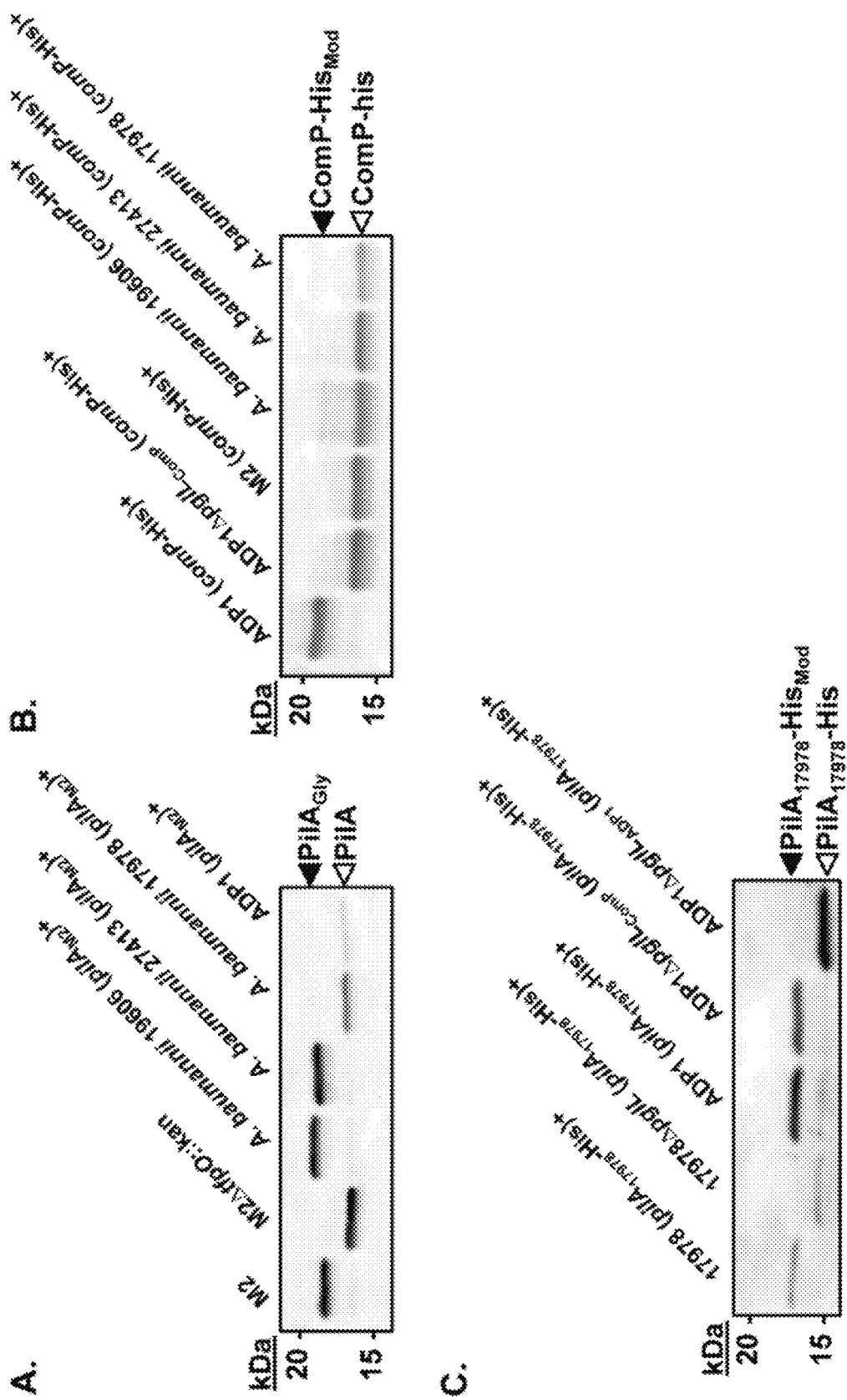

FIG. 9 illustrates that $PglL_{ComP}$, but not TfpOM2, is specific for its cognate pilin protein. (A) Western blot analysis of whole cell extracts probing for heterologous PilAM2 expression and electrophoretic mobility. PilAM2 was glycosylated in *A. baumannii* ATCC 19606 and *A. baumannii* 27413, both of which encode tfpO homologs. Strains lacking tfpO homologs (*A. baumannii* ATCC 17978 and *A. baylyi* ADP1) were unable to glycosylate PilAM2. (B) Western blot analysis probing for heterologous ComP-His expression and electrophoretic mobility. ComP-His was only modified in *A. baylyi* ADP1 indicating that $PglL_{ComP}$ is specific for ComP. (C) Western blot analysis probing for heterologous PilA17978 expression and electrophoretic mobility. PilA17978 was glycosylated in its native strain by PglL17978 and in *A. baylyi* ADP1 by $PglL_{ADP1}$, but not by $PglL_{ComP}$.

Figure 10:
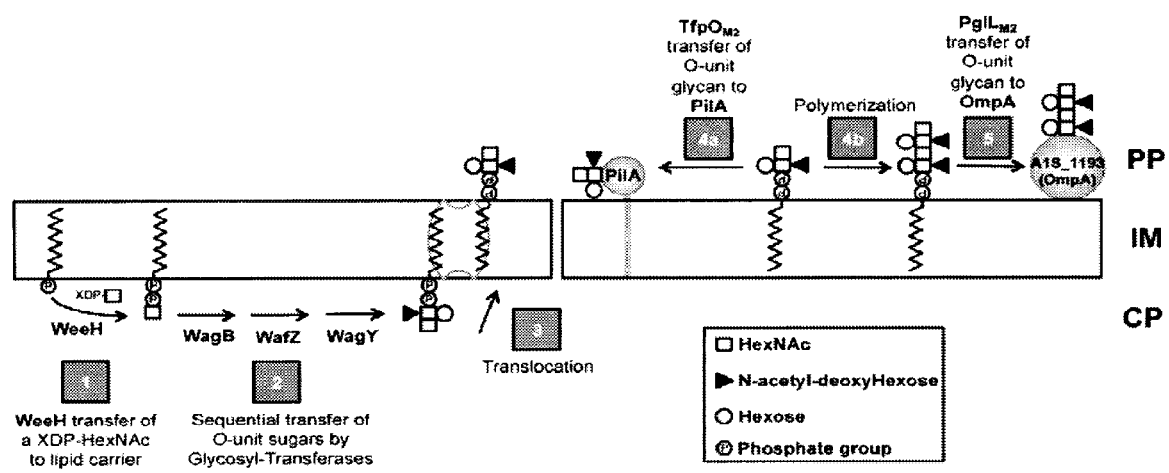

FIG. 10 illustrates a model of lipid-linked oligosaccharide synthesis, TfpOM2-dependent pilin glycosylation, and PglLM2 general O-glycosylation in *A. nosocomialis* strain M2. The proteins encoded by the genes from the major polysaccharide antigen locus synthesize the tetrasaccharide (HexNAc)-(Hex)-(deoxy-Hex)-(HexNAc) on an undecaprenyl lipid carrier, which is then transferred to the periplasm. The lipid-linked oligosaccharide can then be transferred to the major pilin protein, PilA, by the pilin-specific OTase TfpO or further processed and transferred to other proteins, such as, OmpA by the general OTase PglLM2.

Figure 11:
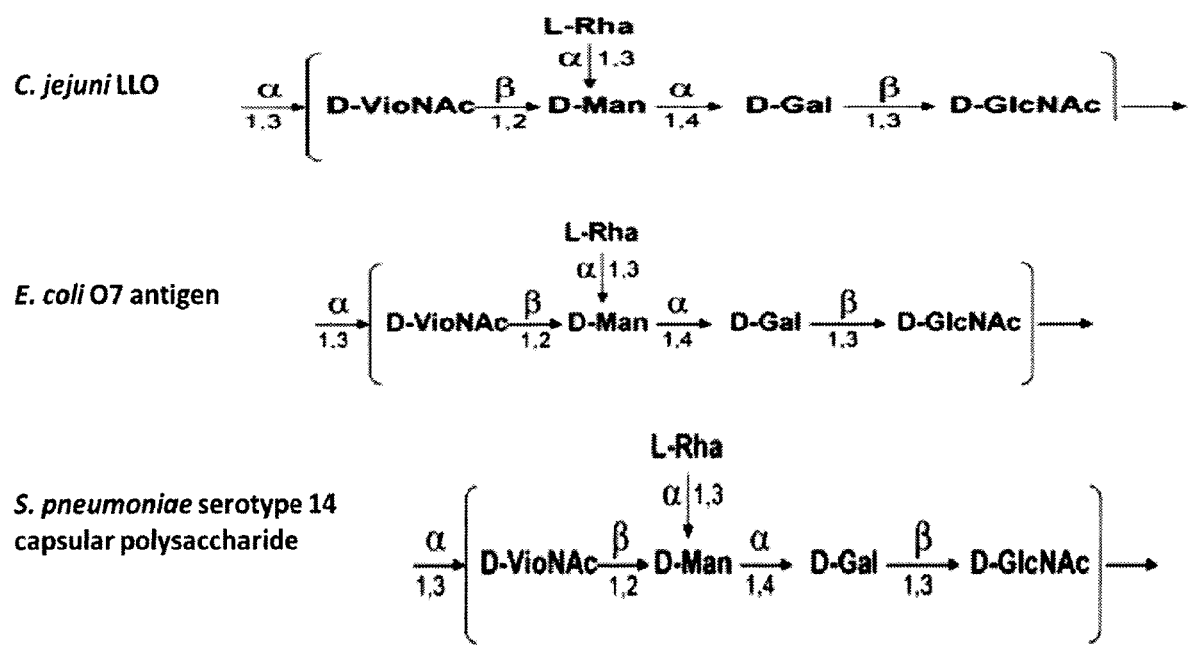

FIG. 11 illustrates the structures of the glycans employed in the present application. Structures are modified from Faridmoayer et al., 2008 and van Selm et al., 2003.

FIG. 12 illustrates $PglL_{ComP}$ transfers *C. jejuni* LLO and *E. coli* O7 antigen to ComP. Western blot analyses on *E. coli* CLM24 whole cell lysates expressing ComP with or without $PglL_{ComP}$ coexpressed with (A) *C. jejuni* LLO and (B) *E. coli* O7 antigen. Lane 1 corresponds to unglycosylated ComP, with no OTase coexpressed. In lane 2, ComP and $PglL_{ComP}$ are coexpressed. (A) Lower electrophoretic mobility bands that react to the anti-his and anti-glycan antibodies indicate glycosylation of ComP by the *C. jejuni*

LLO. (B) Lower electrophoretic mobility bands that react to the anti-his indicate glycosylation by E. coli O7 antigen subunits. Glycoprotein signals disappear upon Proteinase K digests (lane 3). Expression was probed for with a monoclonal anti-his antibody.

Figure 13:
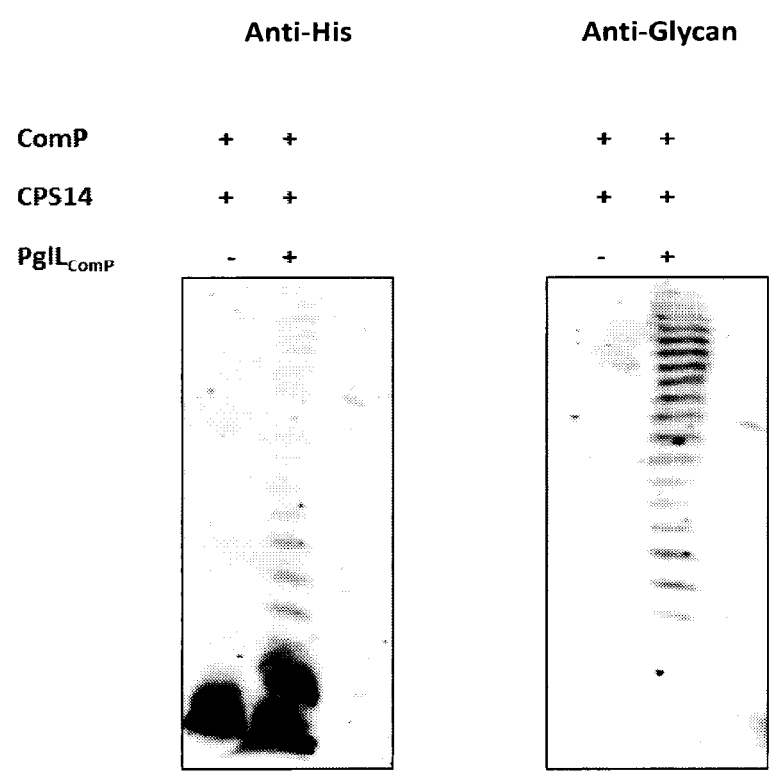

FIG. 13 is an illustration that $PglL_{ComP}$, but not NmPglL or CjPglB, can transfer CPS subunits from S. pneumoniae serotype 14 to ComP. Western blot analyses of (Lane 1) whole cell lysates of E. coli CLM24 expressing his-tagged (A) ComP, (B) DsbA and (C) AcrA. Lane 2 corresponds to Ni-NTA purified proteins from E. coli CLM24 coexpressing the S. pneumoniae serotype 14 CPS synthesis locus and $PglL_{ComP}$. Lower electrophoretic mobility bands in panel A that react to both Anti-His and Anti-Glycan antibodies in lane 2 relative to lane 1 indicate glycosylation of ComP by CPS subunits in a $PglL_{ComP}$-dependent manner Lane 2 in panels B and C shows no lower electrophoretic mobility bands compared to lane 1, indicating the inability of NmPglL and CjPglB to transfer CPS subunits to DsbA1 and AcrA respectively. Expression was probed for with a monoclonal anti-his antibody and a polyclonal anti-glycan antibody.

FIG. 14 is an illustration of visual results of whole cell ELISAs performed on post immune mouse sera obtained after 21 days. ELISAs were done using sera from (A) mice immunized with the unglycosylated protein and probed for with a secondary HRP-conjugated anti-IgM antibody, (B) mice immunized with the glycosylated protein and probed for with a secondary HRP-conjugated anti-IgM antibody, or (C) mice immunized with the unglycosylated protein and probed for with a secondary HRP-conjugated anti-IgG antibody.

Figure 15:
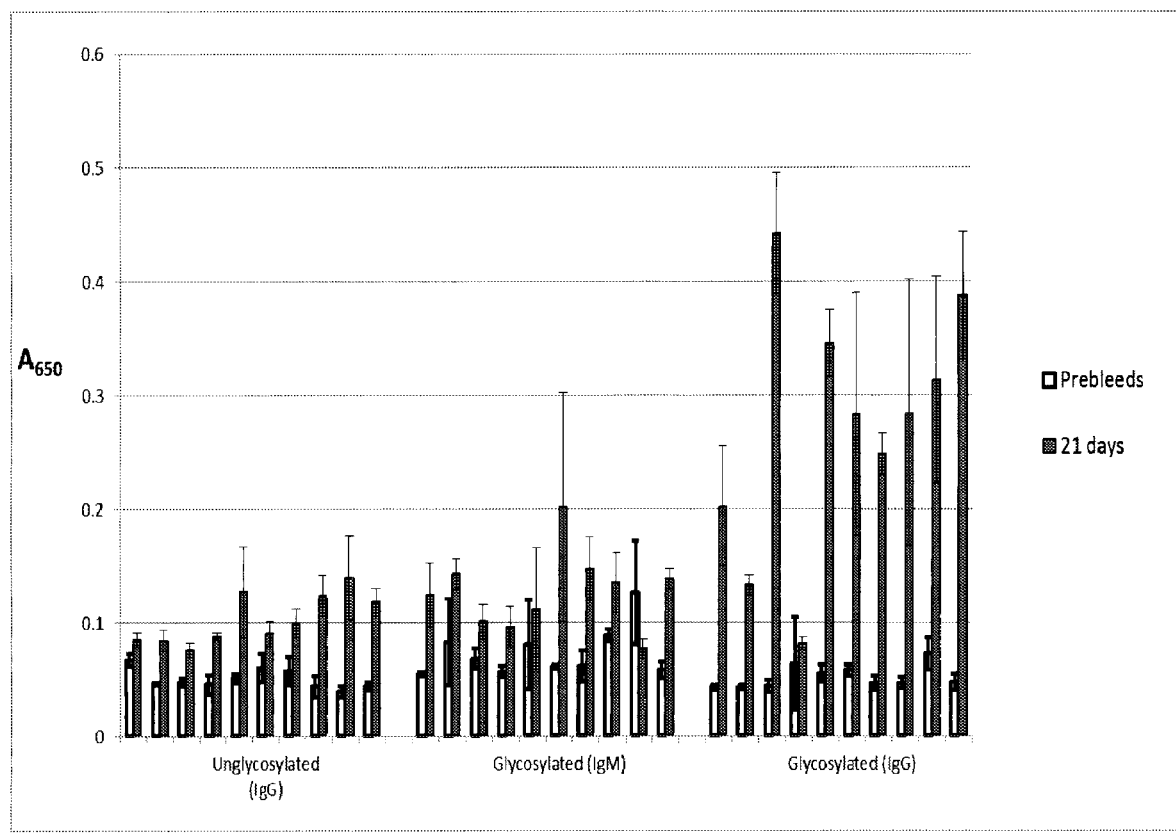

FIG. 15 is a graphical illustration of sera from mice, when injected with CPS-conjugated ComP, react against S. pneumoniae whole cells. Mouse sera from 10 animals (pre immune bleeds and post immune day 21) were incubated in wells of 96 well plates containing immobilized heat-killed whole cell S. pneumoniae serotype 14. As a negative control, sera from 10 mice injected with unglycosylated protein were tested. Secondary HRP-conjugated antibodies used were against mouse IgG antibodies for mice injected with the unglycosylated protein, or against mouse IgM and mouse IgG antibodies for mice injected with the CPS-conjugated ComP. This was followed by treatment with the chromogenic substrate TMB. Sera from mice probed for with the HRP-conjugated mouse IgG antibody showed an increase in absorbance values at 650 nm compared to mice injected with the unglycosylated protein.

FIG. 16 provides a graphical representation of immune responses. Panel (A) illustrates the combined data from whole cell ELISAs against mouse sera. Panel (B) illustrates absorbance values at 650 nm of TMB-treated negative control (no primary antibody) or positive control wells (commercially available rabbit antibody against the S. pneumoniae serotype 14 capsular polysaccharide).

Figure 17:
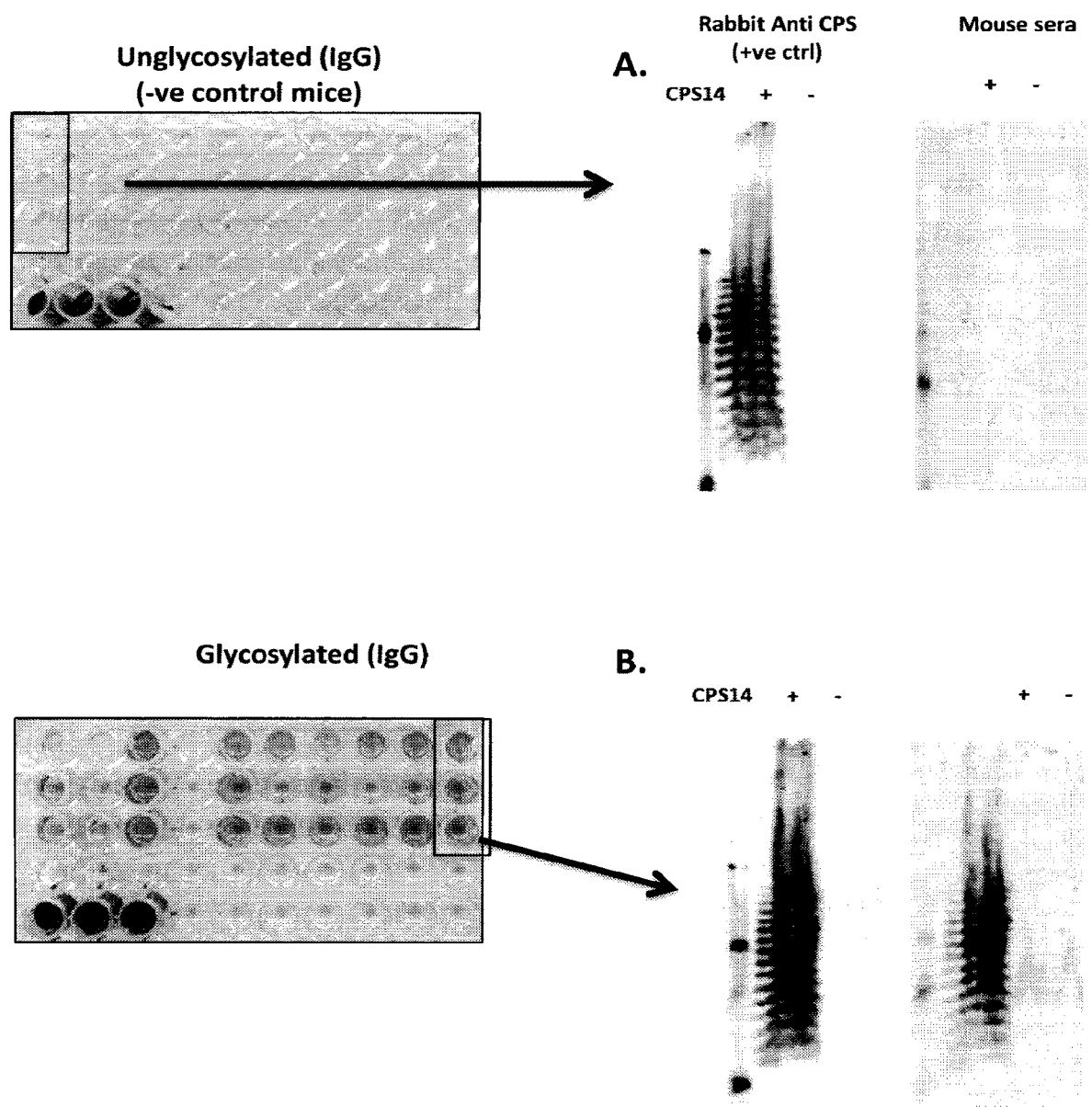

FIG. 17 demonstrates that the IgG immune response observed is directed against CPS from S. pneumoniae serotype 14. Western blot analyses of LPS obtained from E. coli CLM37 probing for expression of S. pneumoniae serotype 14 CPS with the mouse sera followed by a secondary fluorescent mouse anti IgG antibody. (A) Sera from the negative control mice injected with the unglycosylated protein did not react to CPS. (B) Sera obtained from a mouse immunized with the CPS-conjugated ComP that reacted in the ELISA plates reacted to CPS in the Western blots. A commercial anti-CPS rabbit antibody was used as a positive control.

FIG. 18 provides a summary of the current knowledge of the glycans transferred by CjPglB and NmPglL to their acceptor proteins in comparison with $PglL_{ComP}$.

FIG. 19 illustrates quantitative analysis of glycosylation in A. baylyi ADP1 WT, A. baylyi ADP1$\Delta pglL_{ADP1}$, and A. baylyi ADP1$\Delta pglL_{ComP}$ using dimethyl labeling. Using dimethyl labeling and ZIC-HILIC, the O-OTase responsible for glycosylation of individual glycopeptides was confirmed. Glycopeptides derived from A. baylyi ADP1 WT, labeled with light label and A. baylyi ADP1$\Delta pglL_{ComP}$ labeled with heavy label, were observed at near 1:1 levels; whereas, A. baylyi ADP1$\Delta pglL_{ADP1}$, labeled with medium label, was undetectable within samples. Conversely non-glycosylated peptides were observed at a near 1:1:1 level between all three strains. A and D) The MS spectra of the light, medium and heavy isotopologues of the glycopeptide 113KLAEPAASAVADQNSPLSAQQQLEQK138 (SED ID NO: 108) (Q6F825_ACIAD) and non-glycosylated peptide 166AQSVANYLSGQGVSSSR182 (SED ID NO: 109) (Q6FDR2_ACIAD) enabled the comparison of glycosylation across all three strains. No glycopeptides were observed within ADP1$\Delta pglL_{ADP1}$ while non-glycosylated peptides were observed a near 1:1:1 ratio. B and E) Comparison of the extracted ion chromatograms of the light, medium and heavy isotopologues confirm the absent of ADP1$\Delta pglL_{ADP1}$ derived glycopeptides and the 1:1:1 ratio of non-glycosylated peptides. C) HCD fragmentation confirming the identification of the heavy isotopologues of the glycopeptide 113KLAEPAASAVADQNSPL-SAQQQLEQK138 (SED ID NO: 108), confirming its origins from ADP1$\Delta pglL_{ComP}$. F) HCD fragmentation confirming the identification of the medium isotopologues of the non-glycosylated peptide 166AQSVA-NYLSGQGVSSSR182 (SEQ ID NO: 109), confirming its origins from ADP1$\Delta pglL_{ADP1}$.

Figure 20:
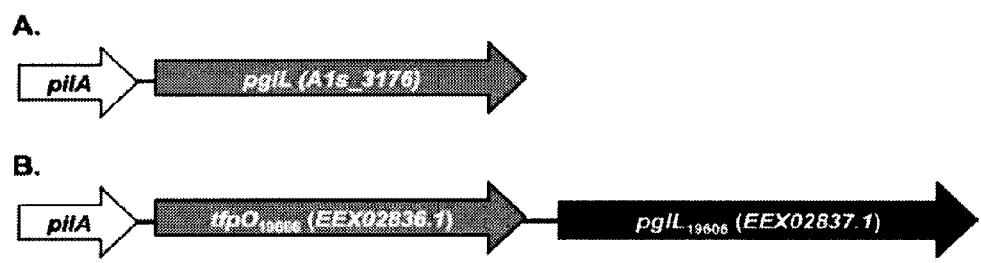

FIG. 20 illustrates genomic organization of OTase(s) in (A) A. baumannii ATCC 17978 and (B) A. baumannii ATCC 19606.

Figure 21:
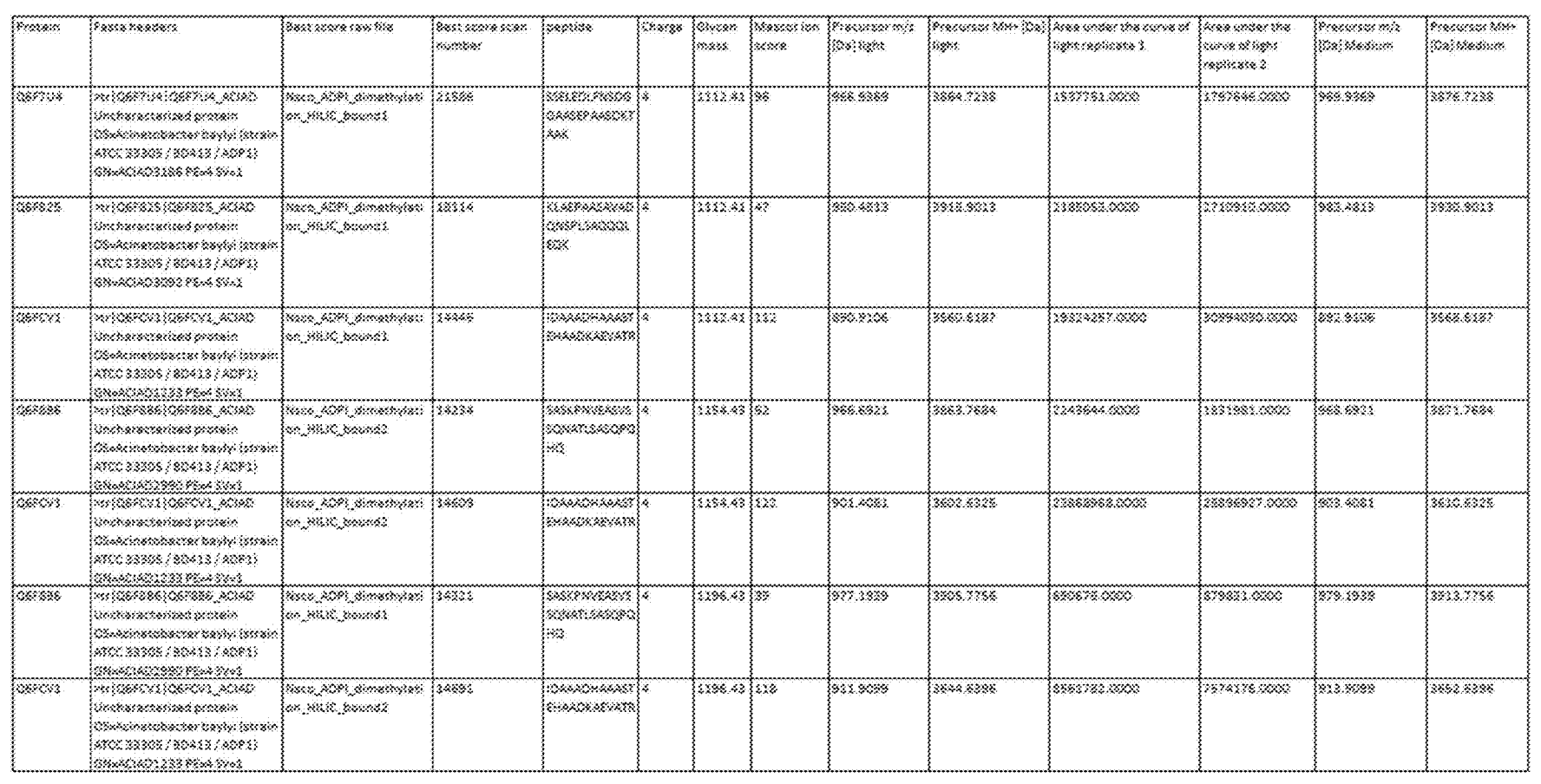

FIG. 21 illustrates quantitative glycopeptides identified in A. baylyi ADP1. (SEQ ID NOs: 79- 82).

DETAILED DESCRIPTION

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

A genomic analysis of sequenced genomes of Acinetobacter spp. revealed that, in addition to A. baylyi ADP1, multiple strains within the genus Acinetobacter encode two OTases. In accordance with the present application there are provided genetic and proteomic techniques to demonstrate that both OTases are functional and that one of these enzymes acted as a pilin-specific OTase, whereas the other OTase was able to glycosylate a wide range of proteins. In addition, using mass spectrometry, the glycan structure of A. nosocomialis strain M2 was characterized and the glycoproteome of A. baylyi defined.

In recent years, a panoply of glycosylation pathways have been identified in bacteria. Irrespective of the pathway utilized, both N- and O-glycans often decorate cell surface adhesins in both Gram-negative and Gram-positive bacteria. Examples of glycosylated surface-associated proteins include the O-glycosylation of AIDA-I and TibA in *E. coli* (Charbonneau et al., 2007; Cote et al., 2013), the type IV pilins of *Pseudomonas, Neisseria, Dichelobacter nodosus*, and *Fransicella tularensis* (Castric et al., 1995, Aas et al., 2006; Faridmoayer et al., 2007, Voisin et al. 2007, Cagatay et al., 2008, Egge-Jacobsen et al., 2011), the flagellins in multiple bacterial species (Nothaft & Szymanski, 2010; Iwashkiw et al., 2013), the serine rich adhesins in *Streptococcus* spp. (Zhou & Wu, 2009), and the N-glycosylation of HMWG in *Haemophilus* (Gross et al., 2008) and *Aggregatibacter actinomycetemcomitans* (Tang & Mintz, 2010). Medically relevant Acb members are not the exception and the present application, as well as previous work, show that pilin and multiple outer membrane proteins are O-glycosylated, which could provide an adherence advantage either to host cells, in bacterial communities, or to abiotic surfaces. However, as of yet, the biological role for glycosylation of *Acinetobacter* pilin subunits has not been elucidated. Specifically, the *A. nosocomialis* strain M2ΔtfpO::kan mutant was equally as transformable as the parental strain (FIG. 3C), exhibited the same twitching motility phenotype as the parent strain, and also contained similar levels of surface 428 exposed PilA (data not shown). Furthermore, no condition was found in which *A. baylyi* ADP1 would attach to abiotic surfaces or form biofilms.

As mentioned previously, pilin glycosylation in *P. aeruginosa* and *P. syringae*, mediated by PilO and TfpO, respectively, was essential for motility, biofilm formation and virulence (Smedley et al., 2005; Nguyen et al., 2012). Pilin glycosylation had no effect on natural competence in *A. baylyi* (Porstendorfer et al., 2000) or *A. nosocomialis* (FIG. 3C). Nevertheless, the ubiquitous nature of O-linked protein glycosylation within the genus *Acinetobacter* suggests a key, still unknown role for this post-translational modification.

As described herein, some *Acinetobacter* strains encode two OTase homologs, one of which is required for general O-glycosylation and the other that specifically modifies pilin. The majority of the medically relevant *Acinetobacter* strains, including *A. nosocomialis* strain M2, encode two contiguous OTases, which are located immediately downstream of a type IVa major pilin subunit gene. At the time of the present application, 76% of *A. baumannii* isolates with completed genomes encoded a PilA protein containing a carboxy-terminal serine. All isolates containing a gene encoding a PilA protein with a carboxy-terminal serine also encode for a tfpO homolog found immediately downstream of pilA. This finding is congruous with findings reported for the group I pilins (PilAI) found in *P. aeruginosa* (Kus et al., 2004). Thus there appear to be multiple lineages of pilin genes, specifically, a lineage that contains an allele that encodes for a PilA with a carboxy-terminal serine and the downstream accessory gene tfpO and lineages that are not glycosylated by a TfpO-like activity. All isolates lacking a carboxy-terminal serine on the major pilin protein, including ATCC 17978, do not encode for a tfpO homolog consistent with the separate evolution of *Acinetobacter* pilin lineages.

In contrast to the contiguous organization of OTases in the medically relevant *Acinetobacter* spp., the two OTases of the environmental isolate *A. baylyi* ADP1 are distantly separated on the chromosome. Schulz et al. (2013) showed that the OTase homolog pglL$_{ComP}$, which is encoded adjacent to comP, is responsible for ComP modification. Mutational analysis coupled with an in vivo glycosylation assay as well as the characterization of the glycoproteome demonstrated that pglL$_{ComP}$ is a ComP-specific OTase. On the other hand, the second OTase, PglLADP1, is not an O-antigen ligase as previously suggested but rather a general O-OTase glycosylating multiple protein targets.

The present application provides that PglLM2, encoded by M215_10475, is able to recognize the same motif that the general O-OTase PglL found in all other *A. baumannii* strains recognizes, as evidenced by the ability of *A. nosocomialis* M2 to glycosylate OmpA-His. In *A. nosocomialis* strain M2, both PglLM2 and TfpOM2 utilize the same lipid linked tetrasaccharide to modify their target proteins. The present application provides that PglLM2 was able to transfer two subunits of the glycan, whereas TfpOM2 only transferred a single glycan chain. Previous studies have shown two subunits of the glycans being transferred by general OTases (Scott et al., 2014); and that TfpO is unable to transfer long sugar chains to *P. aeruginosa* pilin (Faridmoayer et al., 2007). Furthermore, the MPA locus was identified as the source of the genes encoding the proteins responsible for the synthesis of the shared lipid-linked tetrasaccharide. FIG. 10 provides an exemplary model depicting O-glycan synthesis by the MPA cluster and the shared usage of this lipid-linked glycan by TfpOM2 and PglLM2.

Although many protein glycosylation systems have been identified, how O-OTases, such as the ones from *A. baumannii, Neisseria* spp. and *Burkholderia* spp., recognize the acceptor sequences in their protein targets is still not clear. It has been established that OTases recognize low complexity regions (LCR), rich in serine, alanine and proline (Vik et al., 2009). The pilin specific TfpO enzymes described here recognize a peptide of about 15 amino acids containing many serine and proline residues. Similarly to *P. aeruginosa* TfpO, it may be suggested, in accordance with the present application, that the carboxy-terminal serine of PilAM2 may serve as the site of TfpOM2-dependent glycosylation. Bacterial species carrying two functional O-OTases, a PglL-general OTase and a pilin-specific OTase have not previously been identified. TfpO is the only OTase present in *Pseudomonas* (Smedley et al., 2005; Nguyen et al., 2012), while PglL is the only OTase identified in *Neisseria* (Faridmoayer et al., 2007), *A. baumannii* ATCC 17978 (Iwashkiw et al., 2012), *B. cenocepacia* K56-2 (Lithgow et al., 2014) and *R. solanacearum* (Elhenawy et al., submitted). Three possible O-OTases have been identified in *V. cholerae*, but the activity of only one of these has been shown in *E. coli* (Gebhart et al., 2012), and no glycoproteins have been identified in *V. cholerae*. In *N. meningitidis* and *N. gonorrhoeae*, the OTase PglL is able to glycosylate pilin and several other proteins (Aas et al., 2006; Faridmoayer et al., 2007). Although PglL can recognize three glycosylation sites in pilin when the system is reconstituted in *E. coli*, none of them contain the typical LCR domain found in the remaining *Neisseria* glycoproteins, indicating that PglL can recognize more than one motif (Musumeci et al., 2014).

In *Francisella* spp. the OTase is closely related to PilO/TfpO and it appears to be responsible for both pilin and general glycosylation (Balonova et al., 2012). Why *Acinetobacter* strains require two different OTases to glycosylate pilin and other proteins remains unclear as some pathogenic strains of *A. baumannii* carry only PglL, which is required for optimal biofilm formation and virulence (Iwashkiw et al., 2012). It is important to note that non-pathogenic *A. baylyi* ADP1 also contains two O-OTases. However there are several differences between the ComP-specific OTase PglL$_{ComP}$ of *A. baylyi* and the pilin-specific OTases TfpO of the medically relevant *Acinetobacter* spp. Although both OTases are encoded immediately downstream of their cognate protein acceptors (FIG. 1 panels A and C), TfpO OTases are hypothesized to be specific for the carboxy-terminal serine present on PilA, as a carboxy-terminal serine to alanine point mutant was unable to produce glycosylated pilin. Interestingly, all *Acinetobacter* strains encoding a tfpO gene homolog also contained the carboxy-terminal serine on their respective PilA sequences. Furthermore, the present application demonstrates that *Acinetobacter* TfpO homologs are functionally exchangeable as PilAM2 was modified by each tfpO encoding strain tested (FIG. 9A). The variable electrophoretic mobility of PilAM2 is likely due to glycan variability between these strains (Scott, et al., 2014).

Although the site of ComP glycosylation has not been identified, it is predicted to be at an internal residue as ComP does not contain a carboxy terminal serine or any carboxy terminal residue associated with post-translational modification. BLAST analysis of the ComP-specific OTase also demonstrated that PglL$_{ComP}$ is more closely related to the general OTase PglLM2 than to TfpO. Although the pilin-specific TfpO OTase could cross glycosylate different pilins containing carboxy-terminal serines, PglL$_{ComP}$ was unable to glycosylate the pilins recognized by TfpO.

In accordance with the present application, three different classes of OTases are found to be present in *Acinetobacter*: the pilin-specific TfpO enzymes that glycosylate pilins containing carboxy-terminal serine residues; the general PglL OTases that recognize LCR in multiple proteins; and PglL$_{ComP}$, which appears to be exclusively devoted to the glycosylation of ComP. These enzymes have different biochemical characteristics, which provide helpful information for the synthesis of novel glycoconjugates with biotechnological applications. The differentiation between these enzymes is not trivial, and may not be accurately predicted just by the presence of pfam domains. For example, despite having the highest degree of sequence similarity and being functionally homologous, PilO/TfpO from *P. aeruginosa* strain 1244 contains the pfam04932 domain, whereas tfpO from *A. nosocomialis* strain M2 contains the pfam13425 domain. Moreover, the general PglL OTases of the medically relevant *Acinetobacter* spp., including strain M2 and *A. baumannii* ATCC 17978, contain domains from the pfam04932 family and the *A. baylyi* general PglL$_{ADP1}$ OTases contain a pfam13425 domain. Adding to the complexity is the fact that the general PglL OTases from medically relevant *Acinetobacter* spp. and the *A. baylyi* ComP-specific PglL$_{ComP}$ contain the same pfam04932 domains yet recognize different sequons. In addition, this pfam domain is present in the WaaL O-antigen ligases. While bioinformatic analyses can be powerful tools to initially locate and identify ORFs encoding proteins predicted to be involved in glycan transfer events, the present application reinforces the concept that the activity of bioinformatically identified O-OTases must be experimentally determined and reveals a complex and fascinating evolutionary pathway for bacterial O-OTases.

In accordance with the present application, and unlike previously known OTases, PglL$_{ComP}$ can be employed to efficiently attach capsular polysaccharides containing a glucose residue at the reducing end, to a carrier protein, such as ComP. Such capsules are common within the genus *Streptococcus*. Expression of PglL$_{ComP}$ in *E. coli* in presence of plasmids expressing ComP and a capsular polysaccharide from *S. pneumoniae* resulted in the glycosylation of ComP with said polysaccharide. Injection of this glycoprotein in mice mounted a specific IgG immune response against the capsular polysaccharide, demonstrating the applicability of PglL$_{ComP}$ to generate recombinant conjugate vaccines against *Streptococcus*.

To gain a better understanding of the invention described herein, the following examples are set forth. It should be understood that these examples are for illustrative purposes only. Therefore, they should not limit the scope of this invention in any way.

Example 1

Materials and Methods
Strains, Plasmids, and Growth Conditions.
A list of bacterial strains and plasmids used herein are as follows:

TABLE 1

Plasmids and bacterial strains used herein

| Plasmid or strain | Relevant characteristic(s) | Reference/Source |
|---|---|---|
| PLASMIDS | | |
| pFLP2 | Encodes FLP recombinase | Kumar et al., (2010) |
| pKD13 | Contains kanamycin resistance gene from Tn5 flanked by FRT sites | Datsenko & Wanner, (2000) |
| pRSM3542 | pKD13 containing kan-sacB | Carruthers et al., (2013) |
| pGEM-T-Ez | General cloning plasmid | Promega |
| pCC1 | Single copy, general cloning plasmid | Epicentre |
| pSMART-LCKAN | Low copy blunt cloning vector | Lucigen |
| pGEM-pilA | pGEM containing pilA with 1 kb flanking DNA | Harding et al. (2013) |
| pGEM-pilA::kan-sacB | pGEM-pilA containing pilA::kan | This study |
| pCC1-pilA-tfpO-pglL | pCC1 containing the pilA-tfpO-pglL locus with approximately 1 kb of flanking DNA | This study |
| pRSM3510 | pKNOCK derivative with a mini-Tn7 element containing a multiple cloning site | Harding et al. (2013) |
| pRSM3510-pilA | pRSM3510 containing pilA with expression driven from the predicted pilA promoter | Harding et al. (2013) |

TABLE 1-continued

Plasmids and bacterial strains used herein

| Plasmid or strain | Relevant characteristic(s) | Reference/Source |
|---|---|---|
| pRSM3510-pilA[S136A] | pRSM3510-pilA with a carboxy terminal serine to alanine point mutation | This study |
| pRSM3510-pilA[S132A] | pRSM3510-pilA with a serine 132 to alanine point mutation | This study |
| pRSM3510-pilA$^P$-tfpO | pRSM3510 containing the predicted pilA promoter, the ATG of pilA, a FLP scar, the last 21 bp of pilA, and the tfpO gene including the 48 bp intergenic region between pilA and tfpO | This study |
| pCC1-pglL::kan | pCC1-pilA-tfpO-pglL containing pglL::kan | This study |
| pGEM-weeH::kan | pGEM-T-Ez containing weeH::kan | This study |
| pRSM4063 | pSMART-LCKan containing an the empty mini-Tn7 element from pRSM3510 along with 2 kb of flanking DNA up and downstream of the attTn7 from strain M2 | This study |
| pRSM4063-weeH | pRSM4063 containing the weeH gene with its predicted promoter | This study |
| pWH1266 | E. coli - Acinetobacter shuttle vector | Hunger et al., (1990) |
| pGEM-wafY::kan | pGEM-T-Ez containing wafY::kan | This study |
| pGEM-wafZ::kan | pGEM-T-Ez containing wafZ::kan | This study |
| pGEM-wagB::kan | pGEM-T-Ez containing wagB::kan | This study |
| pCC1-GT | pCC1 containing the predicted promoter of the wxy gene (329 bp upstream), wxy, wafY, wafZ, wagA, gnaB, and wagB | This study |
| pCC1-wxy$^P$-wafY | pCC1-GT lacking the wxy open reading frame | This study |
| pCC1-wxy$^P$-wafZ | pCC1-GT lacking the wxy and wafY open reading frames | This study |
| pCC1-wxy$^P$-wagB | pCC1-GT lacking the wxy, wafY, wagA, and gnaB open reading frames | This study |
| pRSM4063-wxy$^P$-wafY | pRSM4063 containing wafY driven off the predicted wxy promoter | This study |
| pRSM4063-wxy$^P$-wafZ | pRSM4063 containing wafZ driven off the predicted wxy promoter | This study |
| pRSM4063-wxy$^P$-wagB | pRSM4063 containing wagB driven off the predicted wxy promoter | This study |
| pWH-pilA$_{M2}$ | pWH1266 expressing pilA$_{M2}$ driven by the predicted pilA promoter | This study |
| pRSM3510-A1S_1193-his | pRSM3510 containing A1S_1193 driven off its predicted native promoter | This study |
| pET-15b | General plasmid for expression and cloning of recombinant proteins based on the T7-promoter driven system | Novagen |
| pET-15b-rsPilA$_{M2}$ | pET-15b expressing a truncated pilA from the T7 promoter | This Study |
| pEXT20 | Amp$^r$ cloning and expression vector, IPTG inducible. | Dykxhoorn et al., (1996) |
| pBAVMCS | Km$^r$ pBAV1K-T5-gfp derivative with gfp ORE removed. Constitutive E. coli/Acinetobacter shuttle vector | Nakar & Gutnick, (2001) |
| pBAV-comP-his | Km$^r$ pBAVmcs constitutively expressing C-6X His-tagged comP from A. baylyi, inserted at BamHI and SalI. | This Study |
| pWH-pilA$_{17978}$-His | pWH1266 expressing pilA$_{17978}$ driven by the predicted pilA promoter | This study |
| pEXT-pglL$_{comP}$ | Amp$^r$ pEXT20 expressing C-6X His-tagged pglL$_{ComP}$ from A. baylyi inserted at BamHI and SalI, IPTG inducible. | This Study |
| pEXT-pglL$_{ADP1}$ | Amp$^r$ pEXT20 expressing C-6X His-tagged pglL$_{ADP1}$ from A. baylyi inserted at BamHI and SalI, IPTG inducible. | This Study |
| pEXT-tfpO$_{19606}$ | Amp$^r$ pEXT20 expressing C-10X His-tagged tfpO$_{19606}$ from A. baumannii ATCC 19606 inserted at BamHI and SalI, IPTG inducible. | This Study |
| pEXT-pglL$_{19606}$ | Amp$^r$ pEXT20 expressing C-10X His-tagged pglL$_{19606}$ from A. baumannii ATCC 19606 inserted at BamHI and SalI, IPTG inducible. | This Study |
| pAMF22 | Tp$^r$ C-10X His-tagged dsbA1 from N. meningitidis MC58 cloned into pMLBAD, Arabinose inducible. | Faridmoayer A. and Feldman M F. (unpublished) |
| pBAV-dsbA1-His | C-6X His-tagged dsbA1 subcloned into pBAVMCS, Km$^r$, at BamHI and HindIII. Constitutively expressing. | This Study |
| pACYCpglB | Cm$^r$ pACYC184-based plasmid encoding the C. jejuni protein glycosylation locus cluster with mutations W458A and D459A in PglB, IPTG inducible. | Wacker et al., (2002) |
| pBAVMCS-A1S_1193His10X | Km$^r$ pBAVMCS constitutively expressing C-10X hist-tagged A1S_1193 inserted at BamHI and SalI. | Scott et al., (2014) |
| STRAINS | | |
| Acinetobacter nosocomialis strain M2 | Metro Health Systems Clinical Isolate | Niu et al., (2008) |
| M2ΔpilA::kan | Strain M2 containing a deletion of pilA and replacement with a kanamycin resistance cassette | Harding et al. (2013) |
| M2ΔpilA::kan-sacB | Strain M2 containing a deletion of pilA and replacement with a kan-sacB cassette | This study |

TABLE 1-continued

Plasmids and bacterial strains used herein

| Plasmid or strain | Relevant characteristic(s) | Reference/Source |
|---|---|---|
| M2ΔpilA | Strain M2 containing an unmarked, in-frame deletion of pilA | This study |
| M2ΔpilT | Strain M2 containing an unmarked, in-frame deletion of pilA | Harding et al. (2013) |
| M2ΔtfpO::kan | Strain M2 containing a deletion of tfpO and replacement with a kanamycin resistance cassette | This study |
| M2ΔtfpO::kanΔpilT::strep | M2ΔtfpO::kan containing a deletion of pilT and replacement with a streptomycin resistance cassette | This study |
| M2ΔpglL::kan | Strain M2 containing a deletion of pglL and replacement with a kanamycin cassette | This study |
| M2ΔpilA (pilA[S136A]+) | M2ΔpilA::kan with a mini-Tn7 element containing an allele of pilA with a carboxy-terminal serine to alanine point mutation | This study |
| M2ΔwafY::kan | Strain M2 containing a deletion of wafY and replacement with a kanamycin resistance cassette | This study |
| M2ΔwafZ::kan | Strain M2 containing a deletion of wafZ and replacement with a kanamycin resistance cassette | This study |
| M2ΔwagB::kan | Strain M2 containing a deletion of wagB and replacement with a kanamycin resistance cassette | This study |
| M2ΔweeH::kan | Strain M2 containing a deletion of weeH and replacement with a kanamycin resistance cassette | This study |
| M2ΔpilA::kan (pilA+) | M2ΔpilA::kan with a mini-Tn7 element containing the pilA gene transcribed from its predicted promoter | Harding et al. (2013) |
| M2ΔtfpO::kan (tfpO+) | M2ΔtfpO::kan with a mini-Tn7 element containing the tfpO gene transcribed from the pilA predicted promoter | This study |
| M2ΔwafY::kan (wafY+) | M2ΔwafY::kan with a mini-Tn7 element containing the wafY gene under control of the predicted wxy promoter | This study |
| M2ΔwafZ::kan (wafZ+) | M2ΔwafZ::kan with a mini-Tn7 element containing the wafY gene under control of the predicted wxy promoter | This study |
| M2ΔwagB::kan (wagB+) | M2ΔwagB::kan with a mini-Tn7 element containing the wafY gene under control of the predicted wxy promoter | This study |
| M2ΔweeH::kan (weeH+) | M2ΔpilA::kan with a mini-Tn7 element containing the pilA gene fused to a FLAG tag transcribed from its predicted promoter | This study |
| M2 (A1S_1193-his+) | Strain M2 with a mini-Tn7 element containing A1S_1193-his transcribed from its predicted promoter | This study |
| M2ΔtfpO::kan (A1S_1193-his+) | M2ΔtfpO::kan with a mini-Tn7 element containing A1S_1193-his transcribed from its predicted promoter | This study |
| M2ΔpglL::kan (A1S_1193-his+) | M2ΔpglL::kan with a mini-Tn7 element containing A1S_1193-his transcribed from its predicted promoter | This study |
| A. baumannii ATCC 17978 | Reference A. baumannii strain | ATCC |
| A. baumannii ATCC 19606 | Reference A. baumannii strain | ATCC |
| A. baumannii 27413 | A. baumannii clinical isolate isolated at Nationwide Children's Hospital (NCH) from body fluid | NCH |
| A. baylyi ADP1 | Environmental isolate | de Berardinis et al., (2008) |
| A. baylyi ΔpglL$_{ComP}$::kan | Strain ADP1 with pglL$_{ComP}$ deleted and replaced with a kanamycin resistance cassette | de Berardinis et al. (2008) |
| A. baylyi ΔpglL$_{ADP1}$::kan | Strain ADP1 with pglL$_{ADP1}$ deleted and replaced with a kanamycin resistance casette | de Berardinis et al. (2008) |
| E. coli DH5a | General cloning strain | Invitrogen |
| E. coli EC100D pir+ | General cloning strain, pir+ | Epicentre |
| E. coli DY380 | Recombineering strain | Lee et al., (2001) |
| E. coli DH5a(pFLP2) | Carries FLP recombinase gene under temperature control | Kumar et al. (2010) |
| E. coli HB101(pRK2013) | Conjugation helper strain | Figurski & Helinski, (1979) |
| E. coli EC100D(pTNS2) | Carries transposase genes for mini-Tn7 transposition | Choi et al., (2005) |
| E. coli Origami 2(DE3) | K-12 derivative containing mutations in trxB and gor genes and a host lysogen of λDE3 | Novagen |
| E. coli Stellar chemically competent cells | HST08 strain derivative for high transformation efficiencies | Clontech |
| E. coli CLM24 | Constructed from E. coli W3110 (IN(rrnD-rrnE)1 rph-1). waaL mutant | Feldman et al., (2005) |

All bacteria were grown on L-agar or in LB-broth at 37° C. unless otherwise noted. When appropriate, antibiotics were added to the A. nosocomialis or A. baumannii cultures at the following concentrations except when noted otherwise: 100 μg ampicillin/mL, 20 μg kanamycin/mL, or 12.5 μg chloramphenicol/mL. When appropriate, E. coli cultures were supplemented with antibiotics at the following concentrations: 50 μg ampicillin/mL for E. coli strains containing plasmids other than pGEM derivatives, 100 μg ampicillin/mL for E. coli strains containing pGEM derivatives, or 20 μg kanamycin/mL. R. solanacearum was grown at 30° C. in BG media (Boucher et al., 1985).

Bioinformatic Analysis of *Acinetobacter* OTases.

Protein sequences for *Acinetobacter* specific OTases were analyzed using NCBI's Basic Local Alignment Search Tool (BLAST) and protein domains identified using the Conserved Domain Database for the annotation of proteins (Marchler-Bauer et al., 2004, Marchler-Bauer et al., 2009, Marchler-Bauer et al., 2011).

Generation of a Strain with an in-Frame Deletion of pilA.

The ΔpilA mutant was constructed, generating an in-frame deletion of pilA, according to the methodology published previously by our group (Harding et al., 2013). Primer sets 1 and 2 were used and can be found in the primer table in the supplemental materials.

Construction of the tfpO::Kan Mutant.

The tfpO::kan mutant was constructed previously (Harding et al., 2013); however, at that time the gene was designated as the pgyA gene, not the tfpO gene.

Complementation of the ΔtfpO::Kan Mutant.

To complement the ΔtfpO::kan mutant, the tfpO gene was cloned with the predicted pilA promoter into a mini-Tn7 element as previously described. Briefly, gDNA from the ΔpilA mutant was used as template with primer set 3 to generate an amplicon containing the predicted pilA promoter, the ATG start codon of the pilA open reading frame, a FLP scar, the last 21 bp of pilA, the 53 bp intergenic region, and the entire tfpO open reading frame. A four-parental mating strategy was used to introduce the mini-Tn7 element containing tfpO driven off the predicted pilA promoter into the ΔtfpO::kan mutant as previously described (Harding et al., 2013). A correct clone was verified by sequencing and designated as the tfpO+ complement.

Plasmid Construction and Transfer into *E. coli*.

The pilA gene from strain M2 was PCR amplified from gDNA using primer set 4 and cloned into the EcoRV site of pWH1266. A correct clone containing the pWH-pilAM2 plasmid was verified by restriction digestion and sequencing. pWH-pilAM2 was purified from *E. coli* harboring the plasmid, then electroporated into *Acinetobacter* isolates. *Acinetobacter* isolates were made electrocompetent according to the methods previously described (Aranda et al., 2010). The pBAV-comP-His plasmid was built by using primer set 32. The sticky-ended amplicon was digested with the respective restriction enzymes and ligated into the vector pBAVmcs in the same sites. The ligation was then electroporated into DH5α-E with transformants being selected for on L-agar plates supplemented with kanamycin. The pEXT-pglL$_{ComP}$, pEXT-pglL$_{ADP1}$, pEXT-tfpO19606 and pEXT-pglL19606 plasmids were built using primer sets 33, 34, 35 and 36 respectively. The resulting amplicons were digested with BamHI and SalI and inserted in the same sites of pEXT20. Ligations were electroplated into DH5α-E and transformants were selected for on L-agar plates supplemented with ampicillin.

pWH-pilA17978-His construction and western blot analysis.

The pilA allele from *A. baumanii* ATCC 17978 was PCR Amplified Using Primer Set 37. The PCR Product was purified and End-it repaired to phosphorylate the 5' ends. The vector pWH1266 was linearized with EcoRI, End-it repaired, and then treated with alkaline phosphatase. The linearized pWH1266 and the PCR purified pilA allele were ligated, transformed into DH5α, and transformants were selected on L-agar supplemented with ampicillin. The pWH-pilA17978 plasmid was sequenced verified and used as template for an inverse PCR to add a C-terminal hexa-histidine tag using primer set 38. The PCR product was purified, DpnI treated, End-it repaired, and ligated. The ligation was electroporated into DH5α and transformants were selected on L-agar supplemented with ampicillin. The pWH-pilA17978-His electroporated into *A. baumannii* strains as previously described and naturally transformed into *A. baylyi* strains according to our previously described methods for transforming *A. nosocomialis* strain M2. *Acinetobacter* transformants were selected on L-agar supplemented with ampicillin. Western blot analysis on whole cell lysates was conducted as described above with the following exceptions. Strains were grown in LB broth without NaCl and were normalized to an OD600=2.0.

Construction of a Strain M2 ΔpglL::Kan Mutant.

The entire pilA-tfpO-pglL locus along with 1 kb of flanking DNA from *A. nosocomialis* strain M2 was amplified using primer set 6. The PCR product was ligated to pCC1 (Epicentre) and transformed into *E. coli* EPI300. A correct clone containing the pCC1-pilA-tfpO-pglL vector was verified by restriction digestion and sequencing. To replace the pglL gene with a kanamycin cassette, a modified recombineering protocol was used as previously described (Harding et al., 2013). To introduce the mutation into *A. nosocomialis* strain M2, the plasmid pCC1-Δpgl::kan was linearized and transformed via natural transformation. Transformants were selected on L-agar supplemented with kanamycin. The M2ΔpglL:kan region in the mutant was verified by sequencing.

Generation of strains containing point mutations in pilA in strain M2. To generate a strain with a carboxy-terminal serine to alanine point mutation in the pilA gene of strain M2, the M2ΔpilA mutant was complemented with a mini-Tn7 element containing a variant of the pilA allele, where the carboxy-terminal serine was mutated to an alanine (pRSM3510-pilA[S136A]). The pRSM3510-pilA[S136A] plasmid was constructed using the Quikchange Site Directed Mutagenesis Kit (Stratagene) according to the manufacturer's protocol using primer set 8. A correct clone carrying the pRSM3510-pilA[S136A] plasmid was verified by restriction digest and sequencing. The mini-Tn7 construct containing the pilA[S136A] allele was transposed into the attTn7 of strain M2 via a four-parental mating strategy previously described above. The same protocol was used to generate the pilA[S132A] except primer set 39 was used.

Construction of Glycosyl-Transferase Mutants in the Strain M2 Background.

In order to replace each glycosyl-transferase gene with a kanamycin resistance cassette, an In-Fusion HD EcoDry cloning kit was used according to the manufacturers protocol (ClonTech). The following protocol describing the construction of the M2ΔweeH::kan mutation was used for each glycosyl-transferase mutant, except the 15 bp overhangs were added to the primers which amplified the 5' and 3' flanking regions of each respective gene. Briefly, the upstream and downstream flanking DNA regions around weeH were PCR amplified with primer sets 9 and 10 respectively. The Tn5 kanamycin cassette and pGEM vector were PCR amplified with 15 bp overhangs homologous to the DNA in which they were to be recombined using primer sets 11 and 12 respectively. The PCR amplicons were gel extracted and ethanol precipitated. One hundred nanograms of each product was added to the In-fusion EcoDry cloning tube according to the manufacturer's protocol and incubated at 37° C. for 15 mins then at 50° C. for 15 mins. The newly generated vector was transformed into chemically competent Stellar cells (Clontech) according to the manufacturer's protocol. Transformants were selected for on L-agar plates supplemented with kanamycin. A correct clone containing the pGEM-weeH::kan plasmid was sequence verified. The weeH::kan cassette was PCR amplified using the forward primer of primer set 9 with reverse primer of primer set 10. The amplicon was DpnI treated, ethanol precipitated, then transformed into strain M2 according to previously published methodologies. A correct clone designated M2ΔweeH::kan was sequence verified.

The upstream and downstream regions of wafY were amplified using primer sets 17 and 18, linearized pGEM was amplified using primer set 15, and the kanamycin cassette was amplified with primer set 16. The above protocol was used to In-Fuse all four PCR products. pGEM-wafY::kan was linearized with EcoRI and introduced into *A. nosocomialis* strain M2 via natural transformation as previously described. A correct clone designated M2 wafY::kan was sequence verified.

The upstream and downstream regions of wag were amplified using primer sets 19 and 20 and the upstream and downstream regions of wagB were amplified using primer sets 21 and 22. Mutants were then constructed as described for the wafY mutant. Clones designated M2Δ wafZ::kan and M2 wagB::kan were identified and sequence verified.

Construction of pRSM4063.

To generate the pRSM4063 vector, an empty mini-Tn7 element was first introduced into strain M2 via a four-parental mating strategy previously described. Transposition of the empty mini-Tn7 element into the attTn7 was sequence verified generating the strain M2attTn7::MCS_Empty. Genomic DNA was purified from this strain and used as a template in a PCR using primer set 13. The forward primer of primer set 13 is approximately 2 kb upstream of the mini-Tn7 element and the reverse primer of primer set 13 is approximately 2 kb downstream of the mini-Tn7 element. The ensuing PCR product was ligated into the pSMART-LCKan vector, sequence verified, and designated pRSM4063.

Construction of the weeH Complemented Mutant.

To complement the weeH::kan mutant, weeH plus 375 bp of upstream DNA was PCR amplified using primer set 14. The amplicon was digested with XmaI and KpnI, cloned into pRSM4063 and electroporated into DH5α. To complement the ΔweeH::kan mutant, pRSM4063-weeH was linearized with NdeI and introduced into M2 ΔweeH::kan via natural transformation according to a previously published procedure (Harding et al., 2013).

Construction of the wafY, Waft, and wagB Complemented Mutants.

Given the lack of an obvious promoter driving expression of each of the glycosyl-transferase genes and the overlapping nature of the open reading frames, the upstream wxy promoter was selected to drive expression of each of the three genes. Each glycosyl-transferase mutant was complemented by returning the deleted gene driven off the predicted wxy promoter to the chromosome using the mini-Tn7 system. Briefly, the glycosyl-transferase locus was PCR amplified using primer set 23, End-It repaired (Epicentre) and ligated into pCC1 (Epicentre). Transformants were selected on chloramphenicol and the pCC1-GT plasmid was verified by restriction digest. The pCC1-GT plasmid contained the predicted promoter of the wxy gene (329 bp upstream), wxy, waft, wag wagA, gnaB, and wagB.

To generate the wxy promoter-wafY construct, an inverse PCR strategy was employed to remove the wxy gene and join the wxy promoter to the ATG start codon of the wafY gene using primer set 24 and pCC1-GT as template. The subsequent PCR product was End-It repaired (Epicentre) and ligated to itself generating the pCC1-wxyP-waft construct. The wxyP-wafY DNA fragment was PCR amplified using primer set 27, which contained XmaI and KpnI restriction overhangs. The PCR product was digested and ligated to predigested pRSM3510 then transformed into EC100D cells. Transformants were selected for on L-agar supplemented with kanamycin. The mini-Tn7 element containing wxyPwafY was introduced into the M2ΔwafY::kan mutant using a four-parental mating strategy previously described.

The same process was used to generate pRSM3510-wxyP-wafY except primer set 25 and primer set 28 were used. The mini-Tn7 element containing wxyP-wafY was introduced to the M2 wafZ::kan mutant via a four-parental mating strategy. The wxyP-wagB fragment was generated using primer set 26 and primer set 29, but was cloned into pRSM4063. The pRSM4063-wxyP-wagB vector was linearized with XhoI and introduced into M2ΔwagB::kan via natural transformation as previously described.

Construction and Transfer of p4063-A1S_1193-5X into *Acinetobacter* Strains.

The A1S_1193 open reading frame along with its predicted promoter was PCR amplified to include a C-terminal 5×His tag using primer set 30, which also contained XmaI and KpnI restriction overhangs. The PCR product was digested and ligated to pre-digested pRSM4063. The pRSM4063-A1S_1193-5X vector was linearized with XhoI and introduced to *Acinetobacter* strains via natural transformation as previously described.

Construction of pET-15b-rsPil$_{AM2}$.

A truncated His-tagged recombinant, soluble derivative of pilA (rsPilAM2) was amplified using gDNA from *A. nosocomialis* strain M2 as template with primer set 31 deleting the first 28 amino acids of the PilA protein. This PCR product was then used as template for a second PCR where the forward primer of primer set 15 contained an NdeI site and the reverse contained a BamHI site to aid in directional cloning into pET-15b. The amplicon was digested with NdeI and BamHI then ligated into the expression vector pET-15b, which was digested with NdeI and BamHI generating a first codon fusion driven off of the T7 promoter with an N-terminal His tag followed by a thrombin cleavage site. Ligation products were electroporated into DH5α-E (Invitrogen), transformants were subcloned and verified to contain the vector with insert by restriction digestion and sequencing. A correct clone was transformed into *E. coli* strain Origami B (DE3) (Novagen) for expression of the recombinant protein.

rsPilAM2 Purification.

Origami B(DE3) (Millipore) containing pET15b-rsPilAM2 was inoculated into 100 mL of LB broth to an A600 nm optical density of 0.05 and grown at 37° C. with 180 rpm to mid-log phase at which point rsPilAM2 expression was induced with IPTG at a final concentration of 500 µM. Cells were transitioned to 19° C. with 180 rpm and grown for 18 h. Cells were harvested by centrifugation into two equal pellets and resolved in 4 mL each of 1× Ni-NTA Bind Buffer (Novagen) with protease inhibitors (Roche). Resuspended pellets were added to 15 mL TeenPrep Lysing matrix B tubes (MP Biomedicals) and lysed in a Fast Prep 24 homogenizer (MP Biomedicals) with two rounds at 6.0 m/s for 40 seconds with a 5 minute incubation on ice between each round. Supernatants were separated from the unlysed bacteria and the lysing matrix by centrifugation at 4000 rpm for 10 mins at 4° C. Supernatants were further clarified with 1 hour of ultracentrifugation at 100,000×g for 1 hour at 4° C. Clarified supernatants were incubated with 1 mL of Ni-NTA His bind resin (Novagen) for 2 hours at 4° C. with gentle rocking followed by two 4 mL washes with 1× Ni-NTA wash buffer. His-tag rsPilAM2 was eluted from the resin with three washes of Ni-NTA elution buffer and dialyzed overnight in phosphate buffered saline. The N-terminal His tag on rsPilAM2 was thrombin cleaved with 0.04 units/µL of biotinylated-thrombin (Novagen) for 2 hours at room temperature. The biotinylated-thrombin was captured with streptavidin-agarose beads for 30 minutes and the rsPilA$_{M2}$ was collected with a centrifugation in a spin filter at 500×g for 5 minutes. To remove any small peptides containing the cleaved His-tag or uncleaved His-tag rsPilAM2, the filtrate was run over Ni-NTA bind resin and the flow through was collected as pure, cleaved rsPilA$_{M2}$. The pure protein was dialyzed in phosphate buffer saline with 50% glycerol then normalized to 1 mg/mL using a BCA total protein assay kit (Pierce).

Generation of Polyclonal Antiserum Against rsPilAM2.

Polyclonal antiserum against rsPil$_{AM2}$ was raised following our previously described methods (Actis et al., 1985). Briefly, 100 µg of purified rsPil$_{AM2}$ emulsified in one milliliter of Freund's complete adjuvant was injected using a 23 gauge needle at ten intracutaneous sites into the haunch of a 6-month old female New Zealand white rabbit (Charles River Laboratories International, Inc., Wilmington, Mass.). Injections consisting of 100 µg rsPilAM2 emulsified in Freund's incomplete adjuvant were subsequently delivered at 15-day intervals, and serum was collected at 10-day intervals following the initial injection. The specificity and reactivity of the anti-rsPil$_{AM2}$ antibodies were confirmed by immunoblotting rsPil$_{AM2}$ and A. nosocomialis strain M2 whole-cell lysates after proteins were size-fractionated by SDS-PAGE.

Transformation Efficiency Assays.

Natural transformation was assayed as described previously (Harding et al., 2013). Transformation efficiency was calculated by dividing the CFU of transformants by the total CFU. Experiments were conducted on at least three separate occasions.

Quantitative Dimethylation of A. baylyi ADP1 Membrane Extracts.

Quantitative dimethylation of lysates from A. baylyi ADP1, the ADP1ΔpglL$_{ComP}$ mutant, and the ADP1 pgl-L$_{ADP1}$ mutant was performed as outlined previously (Boersema et al., 2009). Briefly, 1 mg of peptide lysate from each strain was resuspended in 30 µl of 100 mM tetraethylammonium bromide and mixed with the following combinations of 200 mM formaldehyde (30 µl) and 1M sodium cyanoborohyride (3 µl) isotopologues: ADP1 samples were labeled with light formaldehyde (CH$_2$O) and light sodium cyanoborohyride (NaBH$_3$CN), ADP1ΔpglL$_{ADP1}$ samples with medium formaldehyde (CD2O) and light sodium cyanoborohyride, and ADP1Δ pglL$_{ComP}$ with heavy formaldehyde ($^{13}$CD$_2$O) and heavy sodium cyanoborodeuteride (NaBD$_3$CN). Reagents were mixed and samples incubated at room temperature for 1 h. Dimethylation reactions were repeated twice to ensure complete labeling of all amine groups. Dimethylation reactions were terminated by the addition of 30 µl of 1M NH$_4$Cl for 20 minutes at room temperature. Samples were acidified by addition of 5% (v/v) acetic acid and allowed to equilibrate in the dark for 1 h before pooling the three samples at 1:1:1 ratio. Pooled samples were then STAGE tip purified, lyophilized, and stored at −20° C.

Western Blot Analyses.

Western blot analyses were preformed according to previously described methodologies (Harding et al., 2013). Primary antibodies used were Anti-rsPilAM2 or Penta-His Antibody (Qiagen). Secondary antibodies used were Goat anti-rabbit IgG (H+L), alkaline phosphatase antibody (Molecular Probes) and Goat-anti mouse IgG (H+L), alkaline phosphatase antibody (Molecular Probes). Membranes were developed with the BCIP/NBT Liquid Substrate System (Sigma).

Pili Shear Preparations.

Pili shear preparations were prepared as previously described with the following modifications. Briefly, bacterial lawns were removed from the agar surface and resuspended in 5 mL of ice cold DPBS supplemented with 1× protease inhibitors (Roche). The bacterial suspensions were normalized to an optical density at A600 nm equal to 70. To shear surface exposed proteins, bacterial suspensions were vortexed on high for 1 minute. Bacteria were pelleted at 10,000×g for 10 minutes at 4° C. The supernatants were collected and again centrifuged at 10,000×g for 10 minutes at 4° C. The supernatants were collected and further clarified by centrifugation at 20,000×g for 5 mins at 4° C. The sheared surface proteins were precipitated with ammonium sulfate at a final concentration of 30%. Precipitated proteins were pelleted by centrifugation at 20,000×g for 10 minutes at 4° C. The supernatants were discarded and the pellets were resuspended in 100 µL of 1× Laemmli buffer. Preparations were boiled for 10 minutes, run on SDS-PAGE, coomassie-stained, and bands were excised and prepared for mass spectrometric analysis according to Shevchenko et al. (2006). Briefly, bands were washed with water and dehydrated with acetonitrile (ACN) repeatedly. Disulfide bonds were reduced with 10 mM DTT in 50 mM NH4HCO3 for 60 minutes at 37° C. followed by alkylation of cysteine thiol groups with 50 mM iodoacetamide in 50 mM NH4HCO3 for 60 minutes in the dark at room temperature. Gel pieces were then washed with 50 mM NH4HCO3, dehydrated with 100% ACN and dried. Pilin was digested with 0.02 mg/mL trypsin in 50 mM NH4HCO3 (Promega) at 37° C. for 16 hours. Peptides were eluted with 100% ACN and water and lyophilized Tryptic peptides were resuspended in 0.1% Trifluoroacetic acid and desalted with a C18 ZipTip (Millipore, USA). 60% ACN was used to elute the peptides, which were dried in a speedvac and resuspended with 0.1% Formic Acid. The analysis was done using a Q-TOF Premier (Waters, Manchester, UK) coupled to a nanoACQUITY (Waters) ultra-performance liquid chromatography system as previously described (Wang et al., 2007). MassLynx, v. 4.1 (Waters) was used to analyze the data. OmpA-His was purified from strain M2 and prepared for ESI-QTOF MS/MS analysis as described above.

LPS Extraction and Silver Staining

LPS from A. baylyi and R. solanacearum was extracted from overnight cultures by the TRI-reagent method as described previously (Yi & Hackett, 2000). Equal amounts of LPS were loaded on 12.5% SDS-PAGE gels for LPS separation followed by silver staining as previously described (Tsai & Frasch, 1982).

DsbA1 Glycosylation in E. coli

E. coli CLM24 cells were co-transformed with three plasmids: one plasmid encoding the C. jejuni glycosylation locus, another plasmid encoding a single O-OTase gene, and the last plasmid, pAMF22, encoding dsbAl-His Ampicillin (100 µg/ml), trimethoprim (50 µg/ml) and chloramphenicol (10 µg/ml) were added as required for plasmid selection. Cells were grown at 37° C. to an OD600 of 0.4-0.6 and then were induced with 0.1 mM IPTG and/or 0.2% arabinose. Cultures requiring arabinose induction were given a second dose of induction after 4 hours. Whole cell lysates were obtained at stationary phases and western blot analyses were employed to determine DsbA1 modification.

Digestion of Membrane Enriched Samples of *A. baylyi* ADP1

Peptide lysates for glycopeptide enrichment and quantitative analysis were prepared according to Lithgow et al. (2014) with minor modifications. Briefly, 2 mg of dried membrane enriched protein samples were solubilized in 6 M urea, 2 M thiourea, 40 mM NH4HCO3 and reduced with 10 mM Dithiothreitol (DTT). Reduced, solubilized peptides were alkylated with 25 mM iodoacetamide (IAA) for one hour in the absence of light. The resulting alkylated protein mixture was digested with Lys-C($\frac{1}{100}$ w/w) for 4 hours at 25° C., diluted 1:5 in 40 mM NH4HCO3, then digested with trypsin ($\frac{1}{50}$ w/w) overnight at 25° C. Digestion was terminated with the addition of 1% trifluoroacetic acid (TFA). Peptide digests were purified using the C18 empore (Sigma-Aldrich, St. Louis Mo.) STop And Go Extraction (STAGE) tips (Rappsilber et al., 2007) to remove primary amide and salts.

Enrichment of *A. baylyi* ADP1 Glycopeptides Using ZIC-HILIC Purification

ZIC-HILIC enrichment was performed according to (Scott et al., 2011) with minor modifications. Micro-columns composed of 10 µm ZIC-HILIC resin (Sequant, Umea, Sweden) packed into p10 tips containing a 1 mm$^2$ excised C8 Empore™ disc (Sigma) were packed to a bed length of 0.5 cm. Prior to use, the columns were washed with ultra pure water, followed by 95% acetonitrile (ACN), and then equilibrated with 80% ACN and 5% formic acid (FA). Samples were resuspended in 80% ACN and 5% FA and insoluble material was removed by centrifugation at 16,100×g for 5 min at 4° C. Samples were adjusted to a concentration of 3 µg/µL and 150 µg of peptide material was loaded onto a column and washed with 10 load volumes of 80% ACN, 5% FA. Unbound fractions were collected, pooled, and dried by vacuum centrifugation. ZIC-HILIC bound peptides were eluted with 3 load volumes of ultra-pure water and concentrated using vacuum centrifugation. Biological replicates were subjected to ZIC-HILIC enrichment independently using freshly prepared reagents.

Identification of Glycopeptides Using Reversed-Phase LC-MS, CID MS-MS and HCD MS-MS Purified glycopeptides/peptides were resuspended in Buffer A (0.5% acetic acid) and separated using reversed-phase chromatography on either an Agilent 1290 Series HPLC (Agilent Technologies, Mississauga, ON) coupled to LTQ-Orbitrap Velos (Thermo Scientific, San Jose Calif.) for qualitative analysis of glycopeptides or an EASY-nLC1000 system coupled to a Q-exactive for quantitative studies. For qualitative analysis of *A. baylyi* ADP1 glycopeptides, a packed in-house 20 cm, 75 µm inner diameter, 360 µm outer diameter, ReproSil—Pur C18 AQ 1.9 µm (Dr. Maisch, Ammerbuch-Entringen, Germany) column was used. For quantitative studies a house packaged 45 cm, 50 µm inner diameter, 360 µm outer diameter, ReproSil—Pur C18 AQ 1.9 µm column was used. In both systems, samples were loaded onto a trap column, an in-house packed 2 cm, 100 µm inner diameter, 360 µm outer diameter column containing Aqua 5 µm C18 (Phenomenex, Torrance, Calif.), at 5 µL/min prior to gradient separation and infused for mass spectrometry. A 180 min gradient was run from 0% buffer B (80% ACN, 0.5% acetic acid) to 32% B over 140 min, next from 32% B to 40% B in the next 5 min, then increased to 100% B over 2.5 min period, held at 100% B for 2.5 min, and then dropped to 0% B for another 20 min Unbound fractions from ZIC-HILIC glycopeptide enrichment were subjected to analysis using the same instrumental set up as qualitative analysis of glycopeptides. Both instruments were operated using Xcalibur v2.2 (Thermo Scientific) with a capillary temperature of 275° C. in a data-dependent mode automatically switching between MS, CID MS-MS and HCD MS-MS for qualitative analysis as previously described (Scott et al., 2011) and using a top 10 data-dependent approach switching between MS (resolution 70 k, AGC target of 1×10$^6$), and HCD MS-MS events (resolution 17.5 k AGC target of 1×10$^6$ with a maximum injection time of 60 ms, NCE 28 with 20% stepping) for quantitative studies.

Identification of *A. baylyi* ADP1 Glycopeptides

Raw files for qualitative glycosylation analysis were processed as previously described (Scott et al., 2011, 2012). Briefly, Proteome Discoverer v. 1.2 (Thermo Scientific) was used to search the resulting glycopeptide data using MASCOT v2.4 against the *A. baylyi* ADP1 database (obtained from UNIPROT, http://www.uniprot.org/, 681 2014 Jun. 10, Taxon identifier: 62977 containing 3263 protein sequences). Mascot searches were performed using the following parameters: peptide mass accuracy 20 ppm; fragment mass accuracy 0.02 Da; no enzyme specificity, fixed modifications—carbamidomethyl, variable modifications—methionine oxidation and deamidated N, Q. The instrument setting of MALDI-QUAD-TOF was chosen as previous studies show quadrupole-like fragmentation within HCD spectra (Olsen et al., 2007). Scan events that did not result in peptide identifications from MASCOT searches were exported to Microsoft Excel (Microsoft, Redmond Wash.). To identify possible glycopeptides within exported non match scans, the MS-MS module of GPMAW 8.2 called 'mgf graph' was used to identify HCD scan events that contained the 204.08 m/z oxonium of HexNAc. All scan events containing the oxonium 204.08 m/z ion were manually inspected to identify possible glycopeptides. To facilitate glycopeptide assignments HCD scan events containing the 204.08 oxonium were manual inspected to identify potential deglycosylated peptides ions. Within these HCD scans the MS features (m/z, charge and intensity), which corresponded to masses below that of the deglycosylated peptide were extracted using the Spectrum list function of Xcalibur v2.2. The resulting numerical values of the detected MS features were scripted into mgf files and the peptide mass set to that of the deglycosylated peptide mass. The resulting mgf files were then searched using the MASCOT setting described above. All spectra were searched with the decoy option enabled and no matches to this database were detected; the false discovery rate (FDR) was 0%.

Quantitative analysis of dimethylated *A. baylyi* ADP1 and mutant glycopeptides was performed as previously reported (Lithgow et al., 2014). Briefly, dimethylated *A. baylyi* ADP1 glycopeptides were identified as above and quantified by manually extracting the area under the curve of the monoisotopic peak using Xcalibur v2.2. Triplex (wild type ADP1 vs ADP1ΔpglL$_{ComP}$ vs ADP1ΔpglL$_{ADP1}$).

Results

The Two OTase Homologs Encoded by *Acinetobacter* Contain Different Pfam Domains It was previously reported that *A. baylyi* ADP1 encodes two proteins containing domains from the Wzy_C superfamily (Schulz et al., 2013). Through bioinformatic analyses we identified several *Acinetobacter* spp. with two open reading frames (ORFs) immediately downstream of the major type IVa pilin subunit pilA (FIG. 1, panel A) that are predicted to encode proteins that contain evolutionarily related domains from the Wzy_C superfamily.

Figure 1:
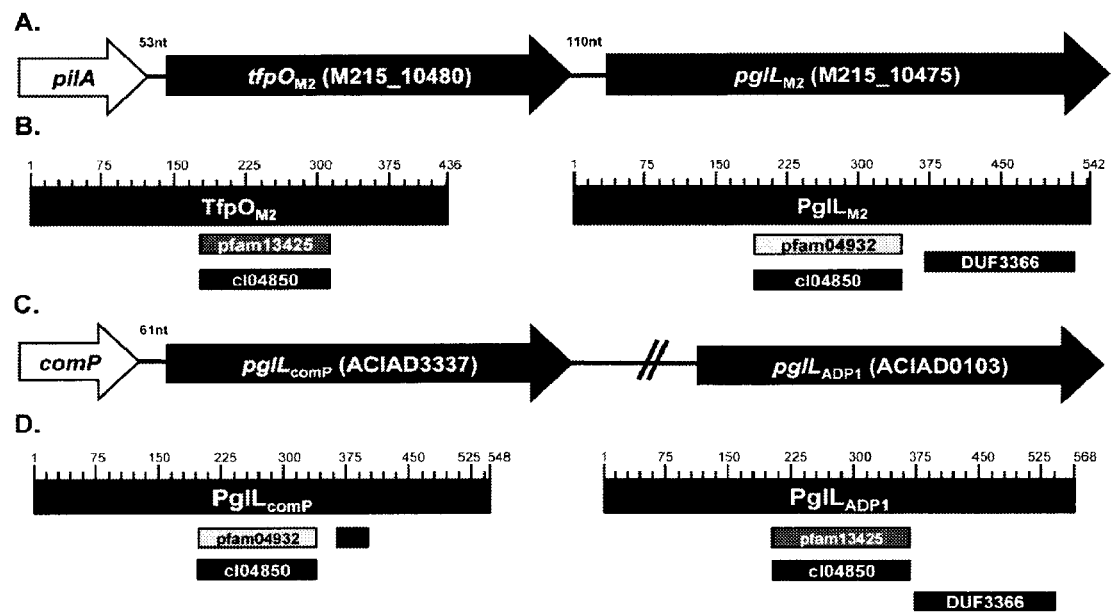
FIG. 1 illustrates genomic and domain organization of putative O-OTases of *Acinetobacter* spp. encoding two OTase genes. (A) Genomic context of OTases encoded by the *A. nosocomialis* strain M2 chromosome. (B) Wzy_C super family (c104850) and DUF3366 domains present in TfpOM2 and PglLM2. (C) Genomic context of OTases encoded by the *A. baylyi* ADP1 chromosome. (D) Wzy_C super family (c104850) and DUF3366 domains present in $PglL_{ComP}$ and $PglL_{ADP1}$. The rectangle below $PglL_{ComP}$ indicates a portion of the DUF3366 domain.

In *A. nosocomialis* strain M2, the pilA gene is immediately upstream of two genes, M215_10480 and M215_10475, both of which encode members of the Wzy_C superfamily M215_10480 and M215_10475 contain the pfam13425 and the pfam04932 domains, respectively (FIG. 1, panels A and B). At the time of this study, the same genetic arrangement was found in 12 of the 17 completed genomes for *A. baumannii* strains, 7 of 8 *A. nosocomialis* genomes, and 3 of 5 *A. pittii* genomes demonstrating the conservation of this locus amongst medically relevant members of the Acb complex (Data not shown). Previously we designated the gene encoding the pfam13425 domain containing protein (ORF M215_10480) as the putative glycosylase A (pgyA) (Harding et al., 2013). Given that the gene encoding M215_10480 is immediately downstream of pilA, together with the functional data provided herein which demonstrates that this protein is a pilin glycosylase, we have renamed the gene encoding ORF M215_10480 as a type four pilin specific O-Oligosaccharyltransferase gene (tfpO).

The second ORF, M215_10475, encodes a predicted protein that contains a domain from the pfam04932 family, a domain that has been found in all previously characterized PglL orthologs as well as in O-antigen ligases. The PglL_A and the PglL_B domains were also identified in M215_10475. It appears that this protein is an ortholog of the PglL general OTases; thus, we have designated ORF M215_10475 as pglLM2 (FIG. 1, panels A and B).

Transcriptome analysis was performed on mid log phase M2 cells using RNA-seq (data not shown). PilAM2 transcription was readily observed; tfpOM2 transcription was also observed but the levels dropped precipitously beginning at the intergenic region between pilAM2 and tfpOM2. A predicted Rho-independent terminator is located immediately upstream of the ATG start codon of tfpOM2. It is likely that pilAM2 and tfpOM2 are in an operon separated by a leaky transcriptional terminator. These findings are consistent with transcriptional studies of pilA and pilO (tfpO) of *P. aeruginosa* 1244 (Castric, 1995). Downstream of the tfpOM2 gene is the pglLM2 gene. Since the genes encoding both OTases are in close proximity and use the same lipid-linked oligosaccharide as a substrate, it was speculated that these genes would be cotranscribed. There does appear to be some transcriptional read through but transcript levels for the pglLM2 gene are markedly higher than the tfpOM2 levels, suggesting that the intergenic region between tfpOM2 and pglLM2 contains a promoter, which also drives transcription of pglLM2.

In the *A. baylyi* ADP1 genome, the comP gene, encoding a pilin-like protein, is followed by ACIAD3337 encoding a pfam04932-containing OTase-like protein, which was designated pglL by Schulz et al., (2013). This has been designated ACIAD3337 as pglL$_{ComP}$ due to its proximity to comP (FIG. 1, panels C and D) and the previously reported evidence demonstrating its requirement for post-translational modification of ComP (Schulz et al., 2013).

A second pfam13425 domain containing ORF (ACIAD0103) predicted to encode a WaaL ligase ortholog was also identified. ACIAD0103 was not located near the pilin gene homolog, but instead was found within a glycan biosynthetic locus. This is herein designated ACIAD0103 as the pglL$_{ADP1}$ (FIG. 1, panels C and D). *A. baylyi* was the only strain containing two genes encoding proteins with domains from the Wzy_C superfamily that were not encoded by adjacent genes.

In *A. baumannii* ATCC 17978, a well-studied strain with respect to its glycosylation, only one general O-OTase was identified, which was previously designated PglL (Iwashkiw et al., 2012; Lees-Miller et al., 2013).

TfpO is Required for Post-Translational Modification of Pilin in *A. nosocomialis* Strain M2.

FIG. 2A shows Western blot analysis of whole cell lysates from strain M2, the isogenic pilA mutant, and the complemented pilA mutant strain confirmed our previous findings that PilA existed in two molecular forms differing by apparent molecular weight. The more abundant, higher molecular weight form of PilA was likely a post-translationally modified species of PilA while the lower molecular weight form of PilA was an unmodified species. To determine the effects of TfpO on PilA post-translational modification, we constructed an isogenic tfpO mutant and probed for PilA expression. PilA from the strain lacking tfpO existed only in the lower molecular weight form (FIG. 2A). The increase in PilA's electrophoretic mobility is consistent with the loss of a post-translational modification. Furthermore, PilA from the complemented tfpO mutant strain existed primarily in the higher molecular weight form confirming that TfpO was required for post-translational modification of PilA.

Immediately downstream of tfpO in strain M2 is pglLM2, which encodes a homolog of the general O-OTases responsible for glycosylation of many membrane associated proteins in *Neisseria gonorrhoeae* and *N. meningitidis* (Vik et al., 2009; Børud et al., 2011). To determine if PglLM2 also played a role in post-translational modification of PilA, an isogenic mutant strain lacking pglLM2 was generated. Western blot analysis of whole cell lysates from the pglLM2 mutant demonstrated that PilA existed primarily in the modified form, indicating that PglLM2 is not required for the post-translational modification of PilA as observed (FIG. 2A).

PilA$_{M2}$ was Glycosylated in a TfpO$_{M2}$-Dependent Manner with a Tetrasaccharide Containing (HexNAc)2, Hexose and N-Acetyl-deoxyHexose.

To confirm that PilA was glycosylated by TfpO, PilA was purified from surface shear preparations from strain M2, a hyper-piliated M2ΔpilT mutant, and a hyper-piliated M2ΔtfpO::kanΔpilT::strep mutant. The pilT gene encodes for the predicted retraction ATPase; therefore, mutants lacking pilT have a hyper-piliated phenotype, which results in an abundance of surface exposed PilA. Proteins in the shear preparations were separated by SDS-PAGE, coomassie-stained, excised and subjected to mass spectrometric analysis. FIG. 2B shows MS/MS analysis of PilA from both strains M2 and M2ΔpilT identified the presence of a tetrasaccharide, comprised of two HexNAc residues, a Hexose and N-acetyldeoxyHexose, on PilA. MS/MS analysis revealed that the tetrasaccharide was present on the carboxy-terminal tryptic 119NSGTDTPVELLPQSFVAS136 peptide. PilA from the M2ΔtfpO::kanΔpilT::strep mutant was unmodified confirming that TfpO was required for PilA glycosylation (data not shown).

The Carboxy-Terminal Serine136 of PilAM2 was Required for Pilin Modification.

In *P. aeruginosa* 1244 the pilin protein PilA is glycosylated in a TfpO-dependent manner (Castric, 1995). The glycosylation site was later determined to be at the carboxy terminal serine 148 (Comer et al., 2002) Amino acid sequences of PilA proteins from *Acinetobacter* spp., including *A. nosocomialis* M2, were compared to the *P. aeruginosa* 1244 PilA. Although the sequences share limited homology, strain M2's PilA sequence also contains a C-terminal serine, which was included in the glycopeptide identified by MS (FIG. 2B).

FIG. 3A shows that, in fact, all *Acinetobacter* spp. containing two consecutive genes encoding O-OTase homologs contain a carboxy-terminal serine in their respective PilA amino acid sequences.

In order to determine if the carboxy-terminal serine136 was required for PilA post-translational modification, the M2(pilA[S136A])+ strain was generated. First, a strain with an in-frame deletion of the pilA gene was generated so as to not affect the transcription of the downstream tfpO gene. We then complemented the M2ΔpilA strain with an allele of pilA where the carboxy-terminal serine was mutated to an alanine residue generating an M2(pilA[S136A])+ strain.

FIG. 3B shows Western blot analysis of whole cell lysates from the M2(pilA[S136A])+ strain demonstrated that PilA only existed in the unmodified, lower molecular weight form indicating that the carboxy-terminal serine was required for PilA post-translational modification). Another highly conserved serine was found at position 132. We constructed the M2(pilA[S132A])+ strain in order to determine if this site was also required for glycosylation. Western blot analysis of whole cell lysates from the M2(pilA[S132A])+ strain demonstrated that PilA existed in the modified form indicating that serine 132 was not required for glycosylation (FIG. 3B). The carboxy terminal serine to alanine point mutation did not affect Tfp functionality as the M2(pilA[S136A])+ strain was naturally transformable (FIG. 3C) and exhibited twitching motility similar to the parental strain (Data not shown).

The Major Polysaccharide Antigen (MPA) Locus is Required for Post-Translational Modification of PilAM2.

Hu et al. recently developed a molecular serotyping scheme for *Acinetobacter* spp. containing a major polysaccharide antigen (MPA) locus. The MPA locus, found between the conserved fkpA and lldP genes, was identified in all sequenced *Acinetobacter* strains included in their study and was also present in *A. nosocomialis* strain M2 (Hu et al., 2013, Carruthers et al., 2013). The MPA locus from *A. nosocomialis* strain M2 contains three predicted glycosyltransferases (designated wafY, wag, and wagB) and one predicted initiating glycosyl-transferase (designated weeH or pglC) (FIG. 4A). To determine if the MPA locus was required for post-translational modification of PilAM2, individual isogenic mutants lacking each of the predicted glycosyltransferases were constructed. FIG. 4B shows Western blot analysis of whole cell lysates from the strain lacking weeH demonstrated that PilA existed in the lower molecular weight form indicating that WeeH is required for glycosylation of PilA. Deletion of the other three glycosyltransferases yielded PilA proteins with intermediate electrophoretic mobilities. PilA from the wafY::kan mutant migrated closest to the WT PilA mobility, then PilA from the wafZ::kan mutant, followed by PilA from the wagB::kan mutant (FIG. 4B). Interestingly, both partially modified and unmodified forms of PilA were identified from the wafZ::kan and wagB::kan mutant backgrounds. All mutant strains were successfully complemented, indicating that the products of wafY, wag wagB, and weeH genes were all required to produce fully modified PilA.

pglLM2 Encodes a PglL-Like O-OTase in *A. nosocomialis* Strain M2 and Uses the Same Tetrasaccharide Precursor as a Donor for General Protein Glycosylation.

In FIG. 2A, pglLM2, the second ORF containing the Wzy_C domain, was shown to not be required for pilin glycosylation. It is thought that pglLM2 may be a general O-OTase that, like the previously characterized PglL in *A. baumannii* ATCC 17978, could glycosylate non-pilin target proteins. We recently demonstrated that A1S_1193-His, encoding for the protein OmpA, could serve as a bait acceptor protein in order to isolate and identify *Acinetobacter* strain specific glycans, as it is recognized by PglLs from different strains (Scott et al., 2014). We expressed OmpA-His, containing a carboxy terminal His-tag, in strains M2, M2ΔtfpO::kan, M2ΔpglL::kan, and M2ΔweeH::kan.

Figure 5A:
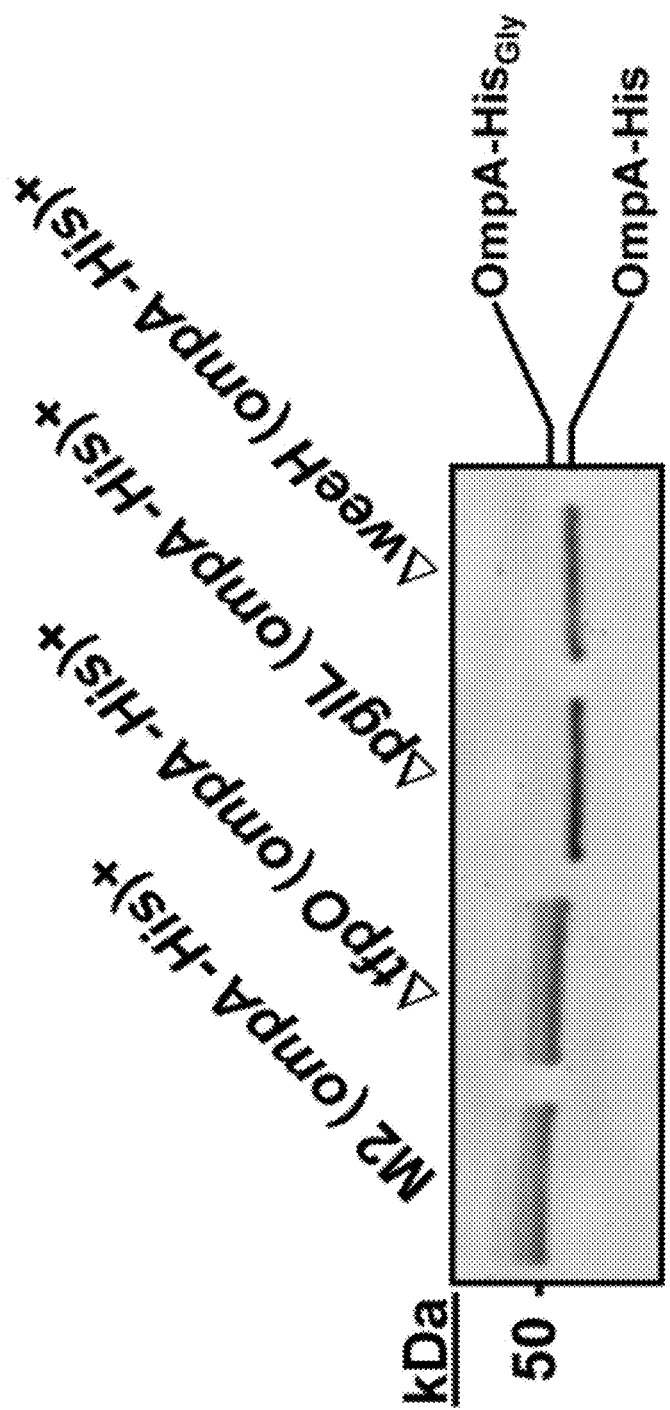
Figure 5B:
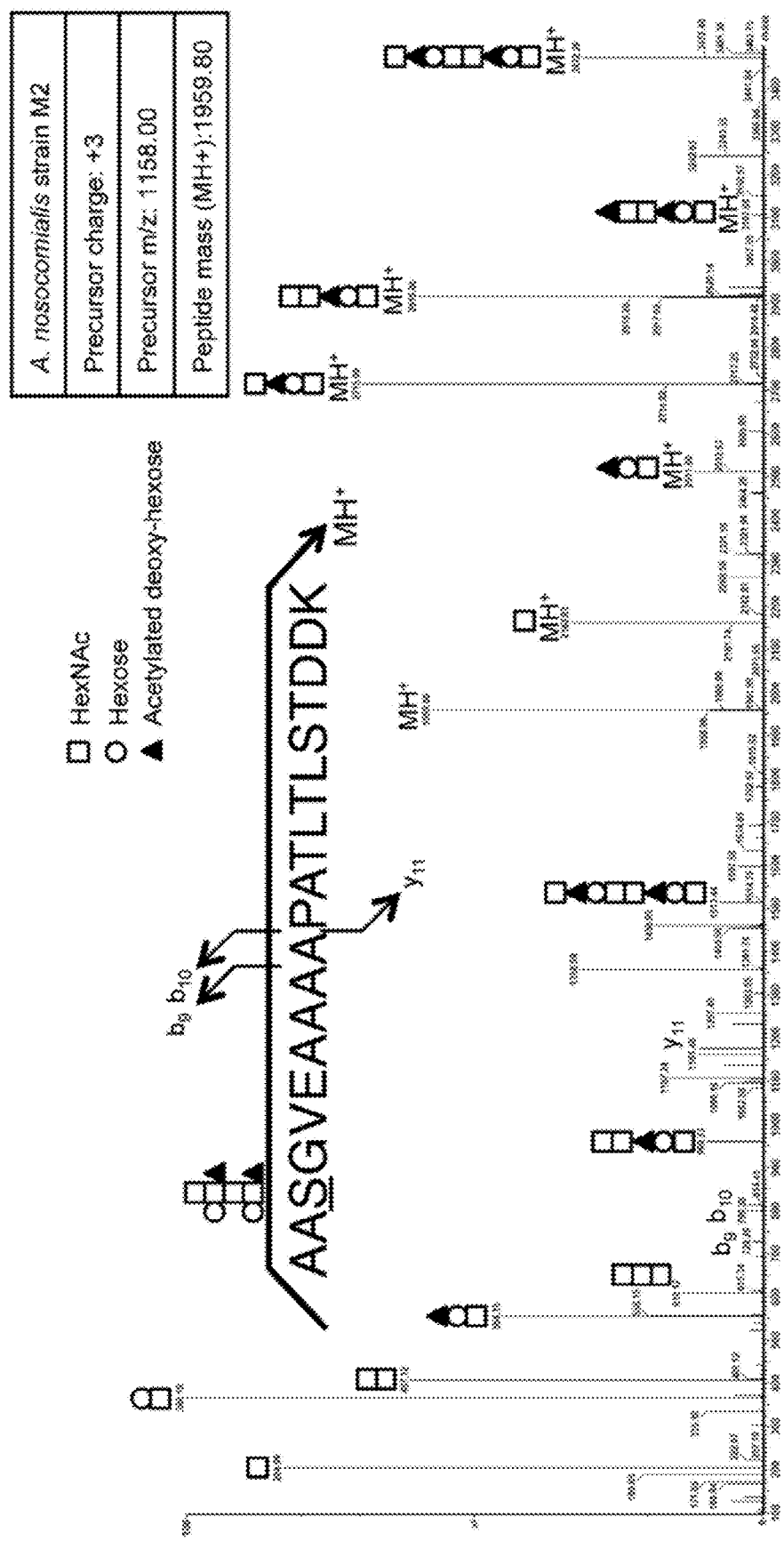

FIG. 5A provides Western blot analysis which demonstrates that all four strains expressed OmpA-His; however, OmpA-His from the M2ΔpglL::kan and the M2ΔweeH::kan backgrounds migrated at an increased electrophoretic mobility, consistent with the lack of a post-translational modification. ESI-TOF-MS/MS analysis of OmpA-His purified from strain M2 revealed glycosylation with two subunits of a branched tetrasaccharide. These results suggest that M215_10475 is a general O-OTase providing functional evidence for the PglLM2 designation. Furthermore, this branched tetrasaccharide was the same tetrasaccharide found on PilA, indicating that TfpOM2 and PglLM2 both utilize the same lipid-linked glycan precursor as the substrate for protein glycosylation (FIG. 5B). This observation was expected given that WeeH was required for both PilA and OmpA-Hispost-translational modification, indicating a common glycan precursor pathway.

ACIAD0103 is not a WaaL O-Antigen Ligase and is not Required for ComP Modification.

As noted above, two OTase-like proteins containing domains from the Wzy_C superfamily are encoded in the *A. baylyi* ADP1 genome. One of these, $pglL_{ComP}$ (ACIAD3337), is located adjacent to comP. Schulz et al. (2013) determined, and we independently confirmed, that $pglL_{ComP}$ (ACIAD3337) is required for ComP modification (FIG. 6A). Furthermore, western blot analysis probing for ComP-His expression from an isogenic $pglL_{ADP1}$ (ACIAD0103) mutant strain demonstrated that $PglL_{ADP1}$ is not required for ComP post-translational modification (FIG. 6A).

Schulz et al. (2013) speculated that the other Wzy_C superfamily domain-containing protein, $PglL_{ADP1}$ (ACIAD0103), encoded a WaaL O-antigen ligase. For LPS biosynthesis, the O-antigen repeat unit is sequentially assembled on the same lipid carrier as the O-glycan on the cytoplasmic side of the inner membrane, flipped to the periplasm, polymerized to form the O-antigen chain and transferred to the lipid A-core polysaccharide by the O-antigen ligase (Hug & Feldman, 2011). Differences in the number of O-antigen subunit repeats in LPS molecules appear as a ladder-like banding pattern in LPS silver stains (Whitfield, 1995). In order to determine if $pglL_{ADP1}$ was acting as an O-antigen ligase, we purified LPS from *A. baylyi* ADP1, the ADP1Δ$pglL_{ComP}$::kan, and ADP1Δ$pglL_{ADP1}$::kan mutants and silver stained the SDS PAGE-separated preparation.

As illustrated in FIG. 6B, LPS silver stained SDS polyacrylamide gels showed identical banding patterns, with no O-antigen subunits observed in the LOS compared to O-antigen-containing LPS obtained from the plant pathogen *Ralstonia solanacearum*. Given that $PglL_{ADP1}$ was not acting as an O-antigen ligase, it is possible that $PglL_{ADP1}$ could encode a second O-OTase.

ACIAD0103 Encodes the General O-OTase, PglLADP1, in *A. baylyi* ADP1

PglL$_{ADP1}$ was tested to determine if it is able to glycosylate DsbA1 from *N. meningitidis* and OmpA from *A. baumannii* ATCC 17978, which are also modified by general O-OTases in their respective strains, and were previously employed as models to study glycosylation (Vik et al., 2009; Iwashkiw et al., 2012; Gebhart et al., 2012; Lithgow et al., 2014). These two proteins were independently expressed in wild-type, ΔpglL$_{ComP}$ and ΔpglL$_{ADP1}$ *A. baylyi* strains. DsbA1-His (FIG. 6C) and OmpA-His (FIG. 6D) displayed an increased electrophoretic mobility in the ΔpglL$_{ADP1}$ background relative to wild-type and ΔpglL$_{ComP}$ backgrounds. These experiments support the role of PglLADP1 as a general O-OTase.

In vivo glycosylation assays in *E. coli* were performed to further confirm the OTase activity of PglL$_{ADP1}$ (Gebhart et al., 2012). We employed *E. coli* CLM24, a strain lacking the WaaL O-antigen ligase, which leads to the accumulation of lipid-linked glycan precursors that then are able to serve as substrates for heterologous O-OTase activity (Feldman et al., 2005). *E. coli* CLM24 was transformed with plasmids encoding an acceptor protein (DsbA1), a glycan donor (the *Campylobacter jejuni* lipid-linked oligosaccharide (CjLLO)), and one OTase, as previously described (Faridmoayer et al., 2007; Ielmini & Feldman, 2011). We also included PglL$_{ComP}$ and employed TfpO19606 and PglL19606, encoding the pilin-specific and the general O-OTase from *A. baumannii* ATCC 19606, as controls. DsbA1-His was detected with an anti-histidine antibody and glycosylation was detected employing the hR6 antibody, which is reactive against the *C. jejuni* heptasaccharide.

As illustrated in FIG. 7, a band reacting with both antibodies, corresponding to DsbA1-His modified by the *C. jejuni* heptasaccharide, was only present in *E. coli* coexpressing DsbA1-His, the CjLLO and either PglL$_{ADP1}$ or the general O-OTase PglL19606. Together this data suggests a role of PglL$_{ADP1}$ as a general O-OTase.

Comparative Proteomic Analysis of *A. baylyi* ADP1 Wild-Type, ΔpglL$_{ComP}$ and ΔpglL$_{ADP1}$ Strains.

To determine a role of both putative O-OTases in *A. baylyi* ADP1 glycosylation, we compared the glycoproteome of *A. baylyi* ADP1 to either the ADP1ΔpglL$_{ComP}$ mutant or the APD1ΔpglL$_{ADP1}$ mutant. Using ZIC-HILIC for glycopeptide enrichment (Iwashkiw et al., 2012; Nothaft et al., 2012; Scott et al., 2014; Lithgow et al., 2014) and multiple MS/MS fragmentation approaches (Scott et al., 2011), 21 unique glycopeptides from eight protein substrates were identified 360 within *A. baylyi* ADP1. Similar to the diversity observed within other *Acinetobacter* spp. (Scott et al., 2014), *A. baylyi* ADP1 generated unique glycans with glycopeptides decorated with one of four pentasaccharide glycoforms composed of 286-217-HexNAc3 (1112.41 Da, FIGS. 8A and 8D), 286-217-245-HexNAc2 (1154.41 Da, FIGS. 8F), 286-217-HexNAc-245-HexNAc (1154.41 Da, FIGS. 8B and 8G) and 286-217-2452-HexNAc (1196.41 Da, FIGS. 8C and 8E). Glycopeptide analysis of membrane proteins from *A. baylyi* ADP1ΔpglL$_{ComP}$ enabled the identification of identical glycopeptides suggesting the glycoproteome was unaffected by the loss of this gene. In contrast none of 21 glycopeptides observed within wild type *A. baylyi* ADP1 could be detected within extracts of *A. baylyi* ADP1ΔpglL$_{ADP1}$ (data not shown), suggesting that pglL$_{ADP1}$ was responsible for general protein glycosylation within *A. baylyi* ADP1.

Glycopeptide Quantitative Labeling

FIG. 19 shows quantitative analysis of glycosylation in *A. baylyi* ADP1 WT, *A. baylyi* ADP1ΔpglL$_{ADP1}$, and *A. baylyi* ADP1ΔpglL$_{ComP}$ using dimethyl labeling.

Figure 19A:
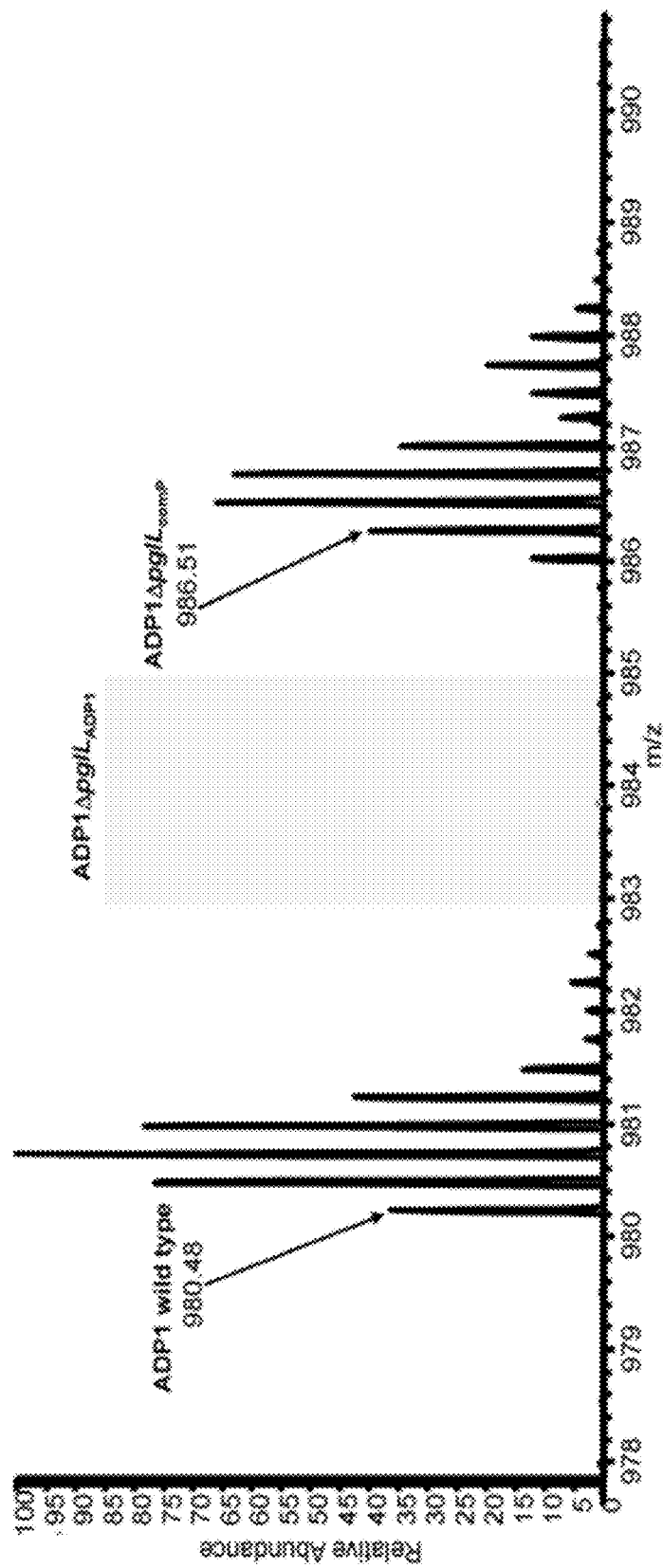
Figure 19B:
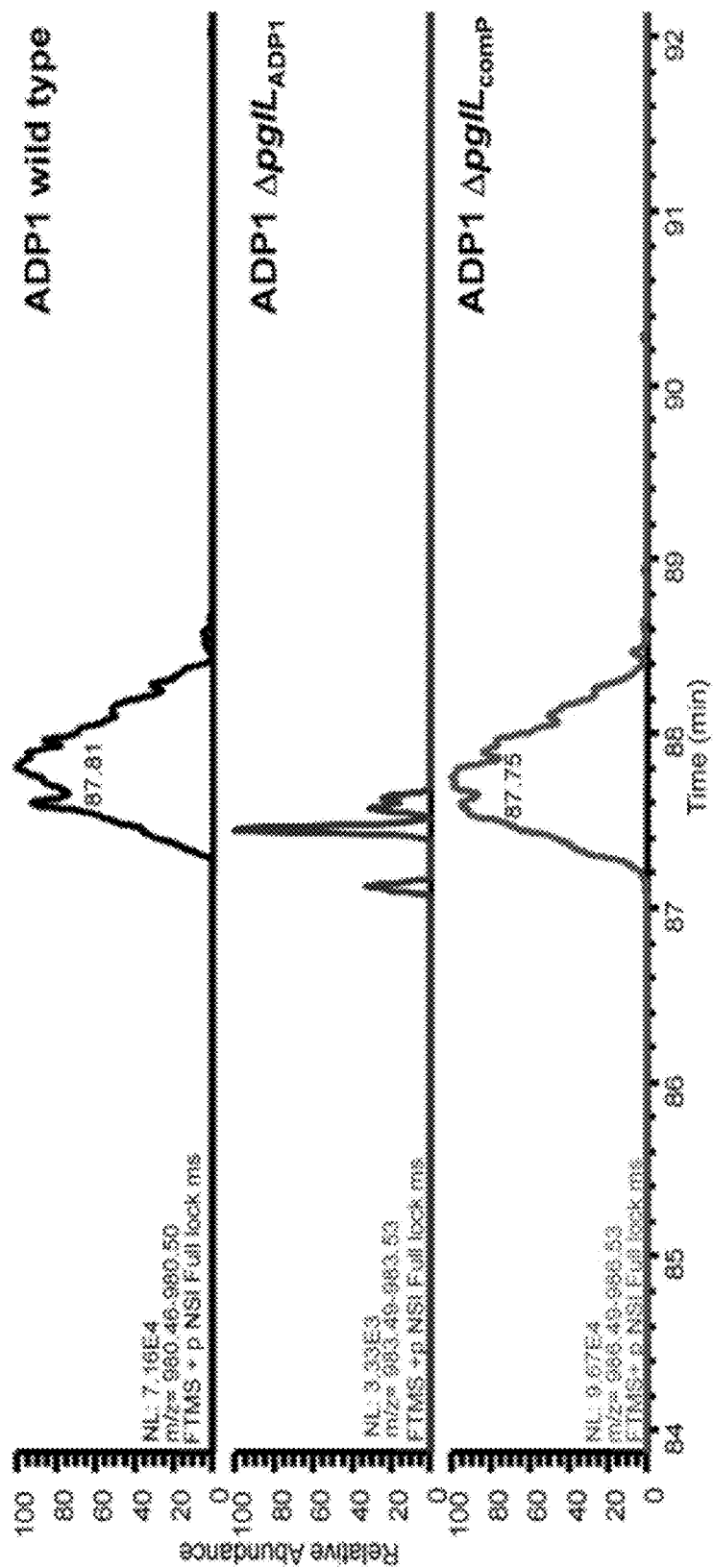
Figure 19C:
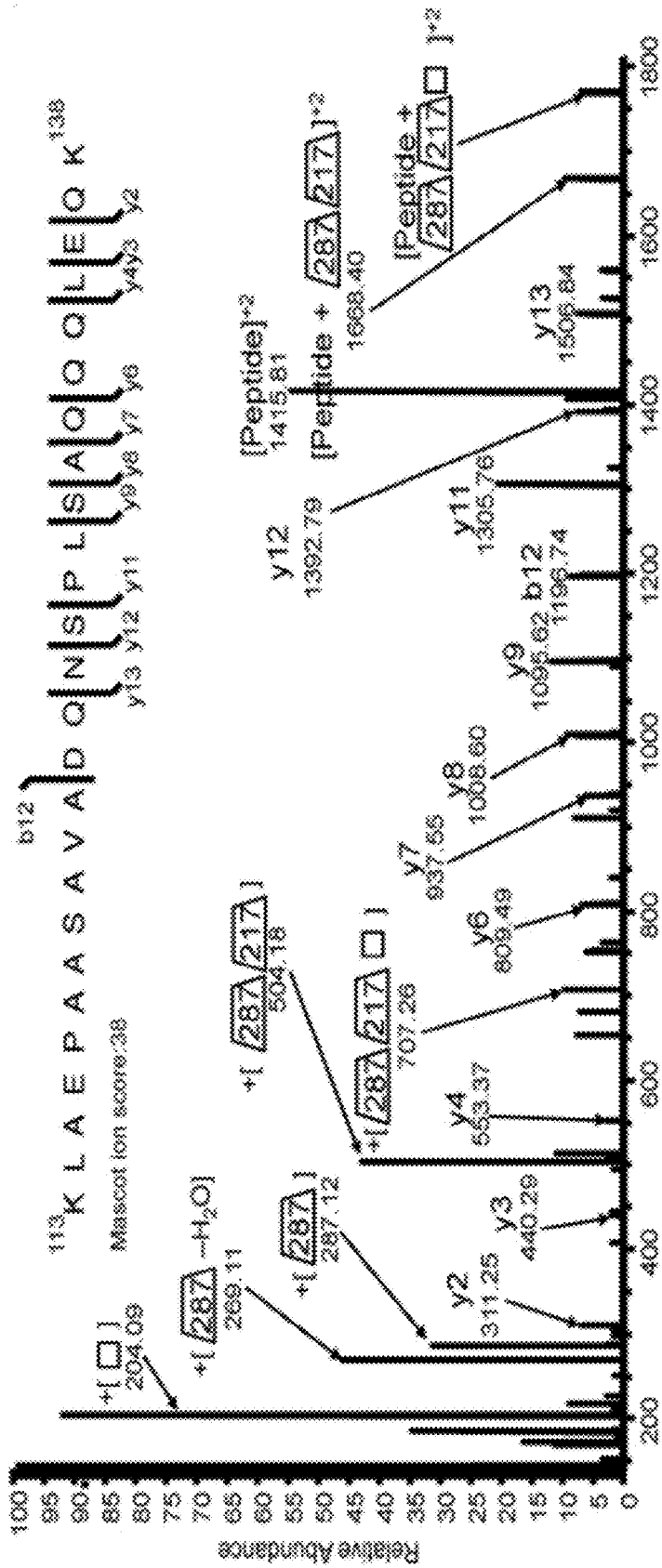
Figure 19D:
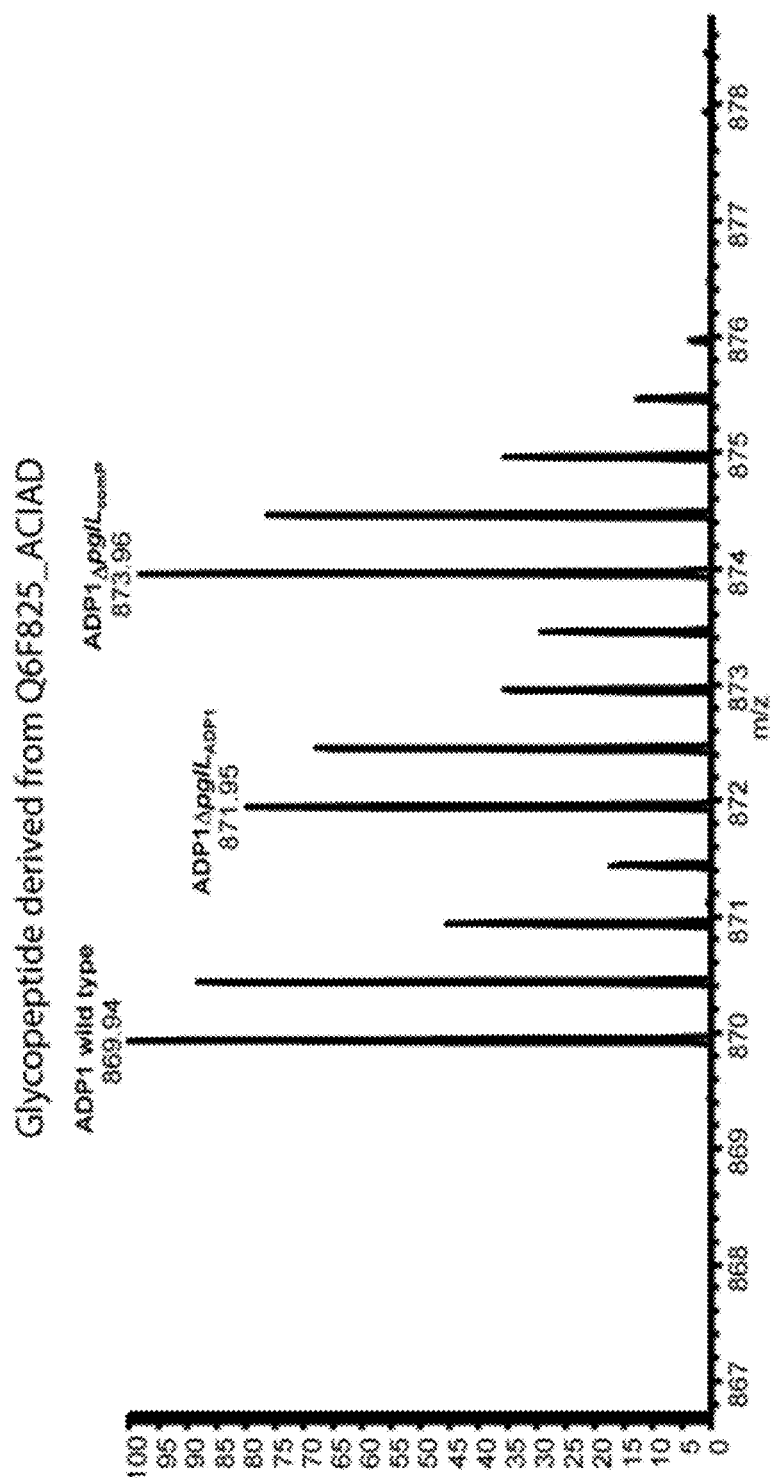
Figure 19E:
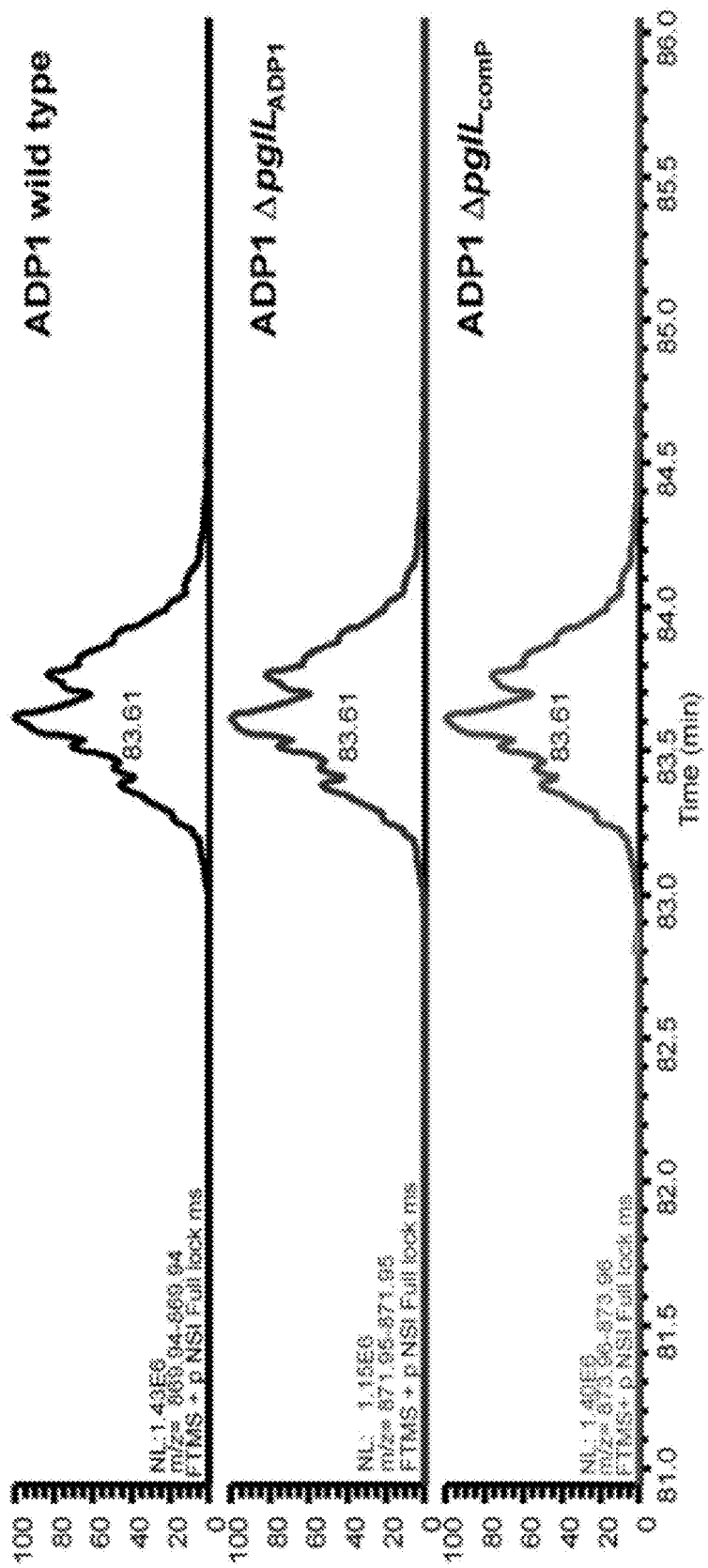
Figure 19F:
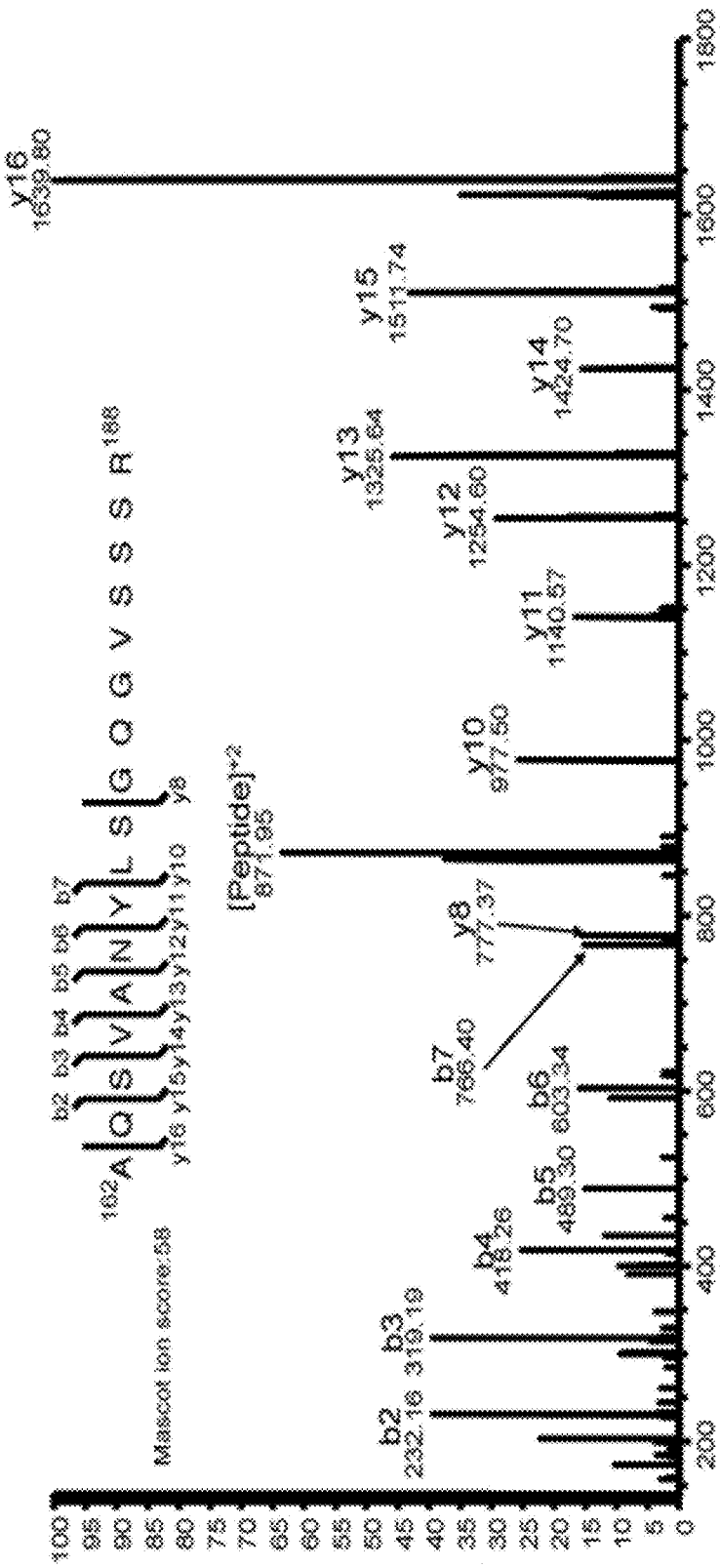

Quantitative dimethylation labeling enabled comparison of all three strains simultaneously providing an internal positive control for glycopeptide enrichment and led to the detection of seven glycopeptides (Table 2). Consistent with the requirement of PglL$_{ADP1}$ for glycosylation, no glycopeptides derived from the ΔpglL$_{ADP1}$ mutant (FIG. 19 A-C) could be detected, while non-glycosylated peptides within the samples were observed at a ~1:1:1 ratio (FIG. 19 D-E, Table 2). Glycosylation was observed at near 1:1 ratio in ΔpglL$_{ComP}$ compared to wild type (ranging from 46% to 170%, FIG. 21) with MS/MS identifications enabling the confirmation of glycopeptides originated from strain ΔpglL$_{ComP}$ (FIG. 19C). Taken together these data suggests PglL$_{ADP1}$ is a general O-linked OTase while PglL$_{ComP}$ is responsible for glycosylation of a specific subset of the glycoproteome, which was not detectable given the sensitivity of the method employed.

Using dimethyl labeling and ZIC-HILIC, the O-OTase responsible for glycosylation of individual glycopeptides was confirmed. Glycopeptides derived from *A. baylyi* ADP1 WT, labeled with light label and *A. baylyi* ADP1ΔpglL$_{ComP}$ labeled with heavy label, were observed at near 1:1 levels; whereas, *A. baylyi* ADP1ΔpglL$_{ADP1}$, labeled with medium label, was undetectable within samples. Conversely non-glycosylated peptides were observed at a near 1:1:1 level between all three strains. A and D) The MS spectra of the light, medium and heavy isotopologues of the glycopeptide 113KLAEPAASAVADQNSPLSAQQQLEQK138 (SEQ ID NO: 108) (Q6F825_ACIAD) and non-glycosylated peptide 166AQSVANYLSGQGVSSSR182 (SEQ ID NO: 109) (Q6FDR2_ACIAD) enabled the comparison of glycosylation across all three strains. No glycopeptides were observed within ADP1ΔpglL$_{ADP1}$ while non-glycosylated peptides were observed a near 1:1:1 ratio. B and E) Comparison of the extracted ion chromatograms of the light, medium and heavy isotopologues confirm the absent of ADP1ΔpglL$_{ADP1}$ derived glycopeptides and the 1:1:1 ratio of non-glycosylated peptides. C) HCD fragmentation confirming the identification of the heavy isotopologues of the glycopeptide 113KLAEPAASAVADQNSPL-SAQQQLEQK138 (SEQ ID NO: 108), confirming its origins from ADP1ΔpglL$_{ComP}$. F) HCD fragmentation confirming the identification of the medium isotopologues of the non-glycosylated peptide 166AQSVA-NYLSGQGVSSSR182 (SEQ ID NO: 109), confirming its origins from ADP1ΔpglL$_{ADP1}$.

Table 2 shows dimethylated glycopeptides identified in *A. baylyi* ADP1. Dimethylated Glycopeptides identified in *A. baylyi* ADP1 wild type (light) and OTase mutant (heavy). Identifications are grouped according to the corresponding Uniprot number. The protein name, parent m/z, charge state, glycan mass, peptide mass, glycan composition, peptide sequence and mascot ion score are provided for each identified glycopeptide. For each identified peptide the dimethylation observed is denoted to aid read distinguish glycopeptide observed from wild type (containing dimethyl N-term and K) and the complement (containing dimethyl N-term 2H(6)13C(2) and K2H(6)13C(2)).

TABLE 2

Dimethylated glycopeptides identified in Acinetobacter baylyi ADP1 (SEQ ID NOs: 79-82)

| Protein | Fasta headers | peptide | Charge | Glycan mass | Precursor m/z | Precursor MH+ | Mascot ion score | Number of labels |
|---|---|---|---|---|---|---|---|---|
| Q6F7U4 | >tr\|Q6F7U4\|Q6F7U4_ACIAD Uncharacterized protein OS = Acinetobacter baylyi (strain ATCC 33305 / BD413 / ADP1) GN = ACIAD3186 PE = 4 SV = 1 | SSELEDLFNSDGGAASE PAASDKTAAK | 4 | 1112.41 | 966.9369 | 3864.7238 | 96 | Dimethyl (K); Dimethyl (K); Dimethyl (N-term) |
| Q6F825 | >tr\|Q6F825\|Q6F825_ACIAD Uncharacterized protein OS = Acinetobacter baylyi (strain ATCC 33305 / BD413 / ADP1) GN = ACIAD3092 PE = 4 SV = 1 | KLAEPAASAVADQNSP LSAQQQLEQK | 4 | 1112.41 | 980.4813 | 3918.9013 | 47 | Dimethyl (K); Dimethyl (K); Dimethyl (N-term) |
| Q6FCV1 | >tr\|Q6FCV1\|Q6FCV1_ACIAD Uncharacterized protein OS = Acinetobacter baylyi (strain ATCC 33305 / BD413 / ADP1) GN = ACIAD1233 PE = 4 SV = 1 | IDAAADHAAASTEHAA DKAEVATR | 4 | 1112.41 | 890.9106 | 3560.6187 | 112 | Dimethyl (K); Dimethyl (N-term) |
| Q6F8B6 | >tr\|Q6F8B6\|Q6F8B6_ACIAD Uncharacterized protein OS = Acinetobacter baylyi (strain ATCC 33305 / BD413 / ADP1) GN = ACIAD2990 PE = 4 SV = 1 | SASKPNVEASVSSQNAT LSASQPQHQ | 4 | 1154.43 | 966.6921 | 3863.7684 | 52 | Dimethyl (K); Dimethyl (N-term) |
| Q6FCV1 | >tr\|Q6FCV1\|Q6FCV1_ACIAD Uncharacterized protein OS = Acinetobacter baylyi (strain ATCC 33305 / BD413 / ADP1) GN = ACIAD1233 PE = 4 SV = 1 | IDAAADHAAASTEHAAD KAEVATR | 4 | 1154.43 | 901.4081 | 3602.6325 | 122 | Dimethyl (K); Dimethyl (N-term) |
| Q6F8B6 | >tr\|Q6F8B6\|Q6F8B6_ACIAD Uncharacterized protein OS = Acinetobacter baylyi (strain ATCC 33305 / BD413 / ADP1) GN = ACIAD2990 PE = 4 SV = 1 | SASKPNVEASVSSQNAT LSASQPQHQ | 4 | 1196.43 | 977.1939 | 3905.7756 | 39 | Dimethyl (K); Dimethyl (N-term) |
| Q6FCV1 | >tr\|Q6FCV1\|Q6FCV1_ACIAD Uncharacterized protein OS = Acinetobacter baylyi (strain ATCC 33305 / BD413 / ADP1) GN = ACIAD1233 PE = 4 SV = 1 | IDAAADHAAASTEHAAD KAEVATR | 4 | 1196.43 | 911.9099 | 3644.6396 | 118 | Dimethyl (K); Dimethyl (N-term) |

(SEQ ID NOs: 79-82)

FIG. 21 (SEQ ID NOs: 79-82) illustrates quantitative glycopeptides identified in *A. baylyi* ADP1. Dimethylated glycopeptides identified in *A. baylyi* ADP1 wild type (light) and OTase mutant (heavy). Identifications are grouped according to the corresponding Uniprot number. The protein name, parent m/z, charge state, glycan mass, peptide mass, glycan composition, peptide sequence and mascot score are provided for each identified glycopeptide. For each identified peptide the dimethylation observed is denoted to aid read distinguish glycopeptide observed from wild type (containing dimethyl N-term and K) and the mutant (containing dimethyl N-term 2H(6)13C(2) and K2H(6)13C(2)).

PgIL$_{ComP}$ Acceptor Protein Specificity Distinguishes it from TfpO and General O-OTases Given the strong genetic linkage between the major type IVa pilin genes and downstream O-OTase genes on *Acinetobacter* chromosomes, we sought to determine whether these O-OTases were specific for their cognate pilin protein. A plasmid expressing PilAM2 from *A. nosocomialis* strain M2 was expressed into different *Acinetobacter* spp., and then conducted western blot analysis probing for the expression and electrophoretic mobility of the pilin protein. PilAM2 was modified by *A. baumannii* ATCC 19606 and the clinical isolate *A. baumannii* 27413, both of which encode tfpO homologs and pilins containing terminal serine residues, as evidenced by the presence of both the higher molecular weight and lower molecular forms of PilAM2 (FIG. 9A). The glycan associated with *A. baumannii* ATCC 19606 was demonstrated to be identical to the pentasaccharide identified in *A. baumannii* ATCC 17978. PilAM2 expressed in *A. baumannii* ATCC 19606 ran with the slowest electrophoretic mobility indicative of a larger glycan associated with PilAM2 (Scott et al., 2014). Both *A. baumannii* ATCC 17978 and *A. baylyi* ADP1, which lack a tfpO homolog, were unable to glycosylate PilAM2.

On the contrary, when ComP-His was heterologously expressed in different *Acinetobacter* spp., it was found that it was glycosylated only in *A. baylyi* ADP1. Strains encoding tfpO homologs were unable to modify ComP-His, with the exception of *A. baumannii* ATCC 19606, which appeared to have a marginal capacity to modify ComP-His (FIG. 9B). PglL$_{ComP}$ was analyzed to determined if it is able to modify *A. baumannii* ATCC 17978 pilin, which does not carry a terminal serine residue. PilA17978 was not glycosylated by PglL$_{ComP}$, but was glycosylated by both its cognate PglL17978 and the PglL$_{ADP1}$ general O-OTases. These results distinguish PglL$_{ComP}$ from the other pilin-specific TfpO OTases that recognize terminal serine residues, and from the general PglL O-OTases. The sequence of PglL$_{ComP}$ is more similar to PglL-like OTases but, unexpectedly, its activity is specific for ComP, which is a pilin-like protein that does not have a terminal serine residue. PglL$_{ComP}$ appears to belong to a new class of O-OTases.

Multiple species within the *Acinetobacter* genus are nosocomial opportunistic pathogens of increasing relevance worldwide. Among the virulence factors utilized by these bacteria are the type IV pili and a protein O-glycosylation system. Glycosylation is mediated by O-oligosaccharyl-transferases (O-OTases), enzymes that transfer the glycan from a lipid carrier to target proteins. O-OTases are difficult to identify due to similarities with the WaaL ligases that catalyze the last step in LPS synthesis. A bioinformatics analysis revealed the presence of two genes encoding putative O-OTases or WaaL ligases in most of the strains within the genus *Acinetobacter*. Employing *A. nosocomialis* M2 and *A. baylyi* ADP1 as model systems, the present application provides that these genes encode two O-OTases, one devoted uniquely to type IV pilin, and the other one responsible for glycosylation of multiple proteins. With the exception of ADP1, the pilin-specific OTases in *Acinetobacter* resemble the TfpO/PilO O-Otase from *Pseudomonas aeruginosa*. In ADP1 instead, the two O-OTases are closely related to PglL, the general O-OTase first discovered in *Neisseria*. However, one of them is exclusively dedicated to the glycosylation of the pilin-like protein ComP.

Glycopeptides identified in *Acinetobacter baylyi* ADP1 wild type are shown in Table 3. Identifications are grouped according to the corresponding Uniprot number. The protein name, parent m/z, charge state, glycan mass, peptide mass, glycan composition, peptide sequence and mascot ion score are provided for each identified glycopeptide.

TABLE 3

Glycopeptides identified in A. baylyi ADP1 (SEQ ID NOs: 79-88)
Glycopeptides identified in Acinetobacter baylyi ADP1

| Protein accession number | Protein name | Precursor m/z [Da] | Precursor MH+ [Da] | Precursor Charge | RT [min] | Peptide | Mascot score | Peptide mass | Glycan mass | page |
|---|---|---|---|---|---|---|---|---|---|---|
| Q6F875_ACIAD | Uncharacterized protein | 703.98 | 2109.92 | 3 | 19.49 | AAHAASAAASK | 62 | 955.50 | 1154.43 | 3 |
| Q6F875_ACIAD | Uncharacterized protein | 717.98 | 2151.93 | 3 | 20.80 | AAHAASAAASK | 35 | 955.50 | 1196.43 | 4 |
| Q6FCV1_ACIAD | Uncharacterized protein | 766.33 | 2296.97 | 3 | 29.47 | DAAHDAAASVEK | 54 | 1184.56 | 1112.41 | 5 |
| Q6FCV1_ACIAD | Uncharacterized protein; | 720.06 | 2877.23 | 4 | 27.44 | IDAAADHAAASTEHAADK | 40 | 1764.82 | 1112.41 | 6 |
| Q6FCV1_ACIAD | Uncharacterized protein; | 730.57 | 2919.24 | 4 | 27.93 | IDAAADHAAASTEHAADK | 32 | 1764.82 | 1154.42 | 7 |
| Q6FCV1_ACIAD | Uncharacterized protein; | 741.07 | 2961.25 | 4 | 28.51 | IDAAADHAAASTEHAADK | 46 | 1764.82 | 1196.44 | 8 |
| Q6FCV1_ACIAD | Uncharacterized protein; | 701.72 | 3504.57 | 5 | 37.64 | IDAAADHAAASTEHAADKAEVATR | 46 | 2392.15 | 1112.42 | 9 |
| Q6FCV1_ACIAD | Uncharacterized protein; | 710.12 | 3546.58 | 5 | 38.00 | IDAAADHAAASTEHAADKAEVATR | 38 | 2392.15 | 1154.43 | 10 |
| Q6FCV1_ACIAD | Uncharacterized protein; | 897.90 | 3588.59 | 4 | 39.70 | IDAAADHAAASTEHAADKAEVATR | 21 | 2392.15 | 1196.44 | 11 |

TABLE 3-continued

Glycopeptides identified in A. baylyi ADP1 (SEQ ID NOs: 79-88)
Glycopeptides identified in Acinetobacter baylyi ADP1

| Protein accession number | Protein name | Precursor m/z [Da] | Precursor MH+ [Da] | Precursor Charge | RT [min] | Peptide | Mascot score | Peptide mass | Glycan mass | page |
| --- | --- | --- | --- | --- | --- | --- | --- | --- | --- | --- |
| Q6F7K5_ACIAD | Uncharacterized protein | 1579.39 | 4736.14 | 3 | 83.54 | IYQNTDTSSAASQTSASPTTQGLGDFLHAQEQLR | 23 | 3623.72 | 1112.42 | 12 |
| Q6F7K5_ACIAD | Uncharacterized protein | 1593.39 | 4778.15 | 3 | 84.29 | IYQNTDTSSAASQTSASPTTQGLGDFLHAQEQLR | 47 | 3623.72 | 1154.43 | 13 |
| Q6F7K5_ACIAD | Uncharacterized protein | 1607.39 | 4820.16 | 3 | 84.77 | IYQNTDTSSAASQTSASPTTQGLGDFLHAQEQLR | 50 | 3623.72 | 1196.44 | 14 |
| Q6F825_ACIAD | Uncharacterized protein | 1278.95 | 3834.82 | 3 | 55.92 | KLAEPAASAVADQNSPLSAQQQLEQK | 50 | 2722.40 | 1112.42 | 15 |
| Q6F825_ACIAD | Uncharacterized protein | 1292.95 | 3876.83 | 3 | 55.87 | KLAEPAASAVADQNSPLSAQQQLEQK | 58 | 2722.40 | 1154.43 | 16 |
| Q6F825_ACIAD | Uncharacterized protein | 980.46 | 3918.84 | 4 | 55.74 | KLAEPAASAVADQNSPLSAQQQLEQK | 48 | 2722.40 | 1196.44 | 17 |
| Q6F814_ACIAD | Putative secretion protein (HlyD family) | 814.04 | 2440.11 | 3 | 20.96 | NTAASSVAATHKK | 65 | 1285.69 | 1154.42 | 18 |
| Q6F814_ACIAD | Putative secretion protein (HlyD family) | 828.05 | 2482.12 | 3 | 20.59 | NTAASSVAATHKK | 56 | 1285.69 | 1196.44 | 19 |
| Q6F8B6_ACIAD | Uncharacterized protein | 1283.91 | 3849.72 | 3 | 37.41 | SASKPNVEASVSSQNATLSASQPQHQ | 57 | 2653.28 | 1196.44 | 20 |
| Q6F7U4_ACIAD | Uncharacterized protein | 1260.88 | 3780.64 | 3 | 66.46 | SSELEDLFNSDGGAASEPAASDKTAAK | 60 | 2668.22 | 1112.41 | 21 |
| Q6FAJ2_ACIAD | Uncharacterized protein | 989.48 | 3954.88 | 4 | 66.33 | VEQIVAQPAPASSVQFKPSNPEIDYK | 26 | 2842.46 | 1112.42 | 22 |
| Q6FAJ2_ACIAD | Uncharacterized protein | 999.98 | 3996.89 | 4 | 66.92 | VEQIVAQPAPASSVQFKPSNPEIDYK | 21 | 2842.47 | 1154.43 | 23 |

Example 2

Materials and Methods:

Strains and Plasmids

A list of the bacterial strains and plasmids used in this study is found in Table 4. *A. baylyi* genomic DNA was isolated using the DNeasy blood and tissue kit (Qiagen). For amplifying the gene aciad3337 (pglL$_{ComP}$) with its upstream non-coding region, primers igrF (ACTGGTCGACTAGTAGTACTATATGGCTTTAAA; SEQ ID NO: 89) and igrR (ACTGCTGCAGTTAATATTC-TATTGAACAAAATTTTAAC; SEQ ID NO: 90) were used. The resulting PCR product was digested with SalI and PstI and inserted in the same sites of pEXT20, creating pMN8. Plasmid pMN1 was constructed by subcloning ComP from pBAV-ComP-his into BamHI and SalI sites of pEXT20. Plasmid pMN2 was constructed by subcloning pglL$_{ComP}$ with its upstream region from the SalI and PstI sites of pMN8 to pMN1.

TABLE 4

Bacterial Strains and plasmids used in this study

| Strain/Plasmid | Description | Reference/Source |
|---|---|---|
| Strains | | |
| *E. coli* CLM24 | W3110, ΔwaaL ligase | Feldman et al. (2005) |
| *E. coli* CLM37 | W3110, ΔwecA glycosyltransferase | Linton et al. (2005) |
| *E. coli* SDB1 | W3110, Δ waaL ligase, ΔwecA glycosyltransferase | Garcia-Quintanilla et al. (2014) |
| *E. coli* DH5α | General cloning strain | Invitrogen |
| Plasmids | | |
| pEXT20 | Cloning vector, Amp$^R$, IPTG inducible | Dykxhoorn et al., (1996) |
| pBAV-ComP-his | C-6X His-tagged ComP cloned in BamHI and SalI sites of pBAVmcs, Kan$^R$, constitutive expression | Harding et al., (2015) |
| pMN1 | C-6X His-tagged ComP cloned in BamHI and SalI sites of pEXT20, Amp$^R$, IPTG inducible | This work |
| pMN2 | Non-coding region and PglL$_{ComP}$ cloned in SalI and PstI sites of pMN1, Amp$^R$, IPTG inducible | This work |
| pMN3 | ComP S69A in pMN2 background | This work |
| pMN4 | PglL$_{ComP}$ H325A in pMN2 background | This work |
| pMN8 | Non-coding region and PglL$_{ComP}$ cloned in SalI and PstI sites of pEXT20, Amp$^R$, IPTG inducible | This work |
| pMAF10 | HA-tagged PglB cloned in pMLBAD, TpR, Arabinose inducible | Feldman et al. (2005) |
| pAMF10 | C-10× His-tagged NmPglL cloned inyo pEXT20, AmpR, IPTG inducible | Faridmoayer et al., (2008) |
| pIH18 | C-6X His-tagged AcrA from C. cloned into pEXT21, SpR, IPTG inducible | Hug et al., 2010 |
| pAMF22 | C-6X His-tagged dsbA1 from *N. meningitidis* MC58 cloned into pMLBAD, Tp$^R$ Arabinose inducible | Faridmoayer et al., (unpublished) |
| pACYCpglBmut | pACYC184-based plasmid encoding the *C. jejuni* pgl locus with mutations W458A and D459A in PglB. Cm$^R$, IPTG inducible. | Wacker et al., (2002) |
| pEXT20-pglL$_{ADP1}$ | pEXT20 expressing C-6X His-tagged pglLADP1 from *A. baylyi* inserted at BamHI and SalI, Amp$^R$, IPTG inducible | Harding et al., (2015) |
| pLPS2 | *P. aeruginosa* O11 antigen synthesis cluster, Tet$^R$ | Goldberg et al., (1992) |
| pJHCV32 | *E. coli* O7 antigen synthesis cluster, Tet$^R$ | Feldman et al., (1999) |
| pNLP80 | *S. pneumoniae* CPS14 cluster on pWSK129, Kan$^R$ | Price et al., unpublished |
| pOSH59 | *S. pneumoniae* CPS15b cluster on pACT3, Cm$^R$ | Posch et al., unpublished |
| pPR1347 | *S. enterica* serovar *Typhimurium* O antigen synthesis cluster, Kan$^R$ | Neal et al., (1993) |

Glycosylation in *E. coli*

Electrocompetent *E. coli* CLM24, CLM37 or SDB1 were prepared as per the protocol described by Dower and colleagues (Dower et al., 1988). Cells were transformed with plasmids encoding the glycan synthesis loci, acceptor protein and OTase. For plasmid selection, ampicillin (100 µg/ml), tetracycline (20 µg/ml), trimethoprim (50 µg/ml), chloramphenicol (12.5 µg/ml), kanamycin (20 µg/ml) and spectinomycin (80 µg/ml) were added as needed. Cells were grown at 37° C. in LB broth to an $OD_{600}$ of 0.4-0.6, induced with 0.05 mM or 0.1 mM IPTG or 0.2% arabinose as required and left overnight at 37° C. Cultures requiring arabinose induction received a second dose of arabinose after 4 hours. Whole cell lysates were obtained at stationary phases, of which 0.1 OD were loaded on 12.5% SDS-PAGE gels, which were then transferred to nitrocellulose membranes. Western blot analysis was employed to determine protein modification and antibodies used are outlined in Table 5. Nitrocellulose membranes were visualized using the Odyssey Infrared Imaging System (LiCor Biosciences, USA).

TABLE 5

Antibodies used in the present application

| Antibody | Description | Reference/Source |
|---|---|---|
| Anti His Poly | Rabbit polyclonal, 1:4000 | Rockland |
| Anti His Mono | Mouse monoclonal, 1.5000 | Abcam |
| Anti CPS14 | Rabbit polyclonal, 1:1000 | Statens |
| Anti CPS15b | Rabbit polyclonal, 1:1000 | Statens |
| Anti Pseudomonas O11 antigen | Rabbit polyclonal, 1:500 | Lam lab, University of Guelph |
| Anti Salmonella LT2 O antigen | Rabbit polyclonal, 1:1000 | Statens |
| hR6 | Rabbit polyclonal, 1:200000 | Aebi lab |
| Goat Anti rabbit IR680 | 1:15000 | Li-Cor |
| Goat Anti mouse IR800 | 1:15000 | Li-Cor |
| HRP-conjugated IgM | Mouse monoclonal 1:10000 | Rockland |
| HRP-conjugated IgG | Mouse monoclonal 1:10000 | Rockland |
| HRP-conjugated | Rabbit polyclonal 1:5000 | Rockland |

Total Membrane Preparations

Cells grown overnight at 37° C. in Terrific broth were washed with phosphate buffered saline (PBS) buffer and resuspended in the same buffer. Cells were lysed by two rounds of cell disruption using a French press at 20 kpsi followed by the addition of a protease inhibitor cocktail (Roche). Lysates were centrifuged for 30 minutes at 10000×g to get rid of cell debris and supernatants were then ultracentrifuged at 100000×g for 60 minutes to pellet total membranes. The pellet was resuspended in a buffer containing 0.1% Triton ×100 or 1% n-dodecyl-β-D-maltoside (DDM) in 10 ml PBS and membrane proteins were solubilized by tumbling overnight. An equal volume of PBS was added to the suspension to reduce detergent concentration and the suspension was ultracentrifuged at 100000 G for 60 minutes. Supernatants, which correspond to solubilized membrane proteins, were loaded on columns for nickel affinity protein purifications.

Nickel Affinity Protein Purifications

Hexa-histidine-tagged proteins were purified from solubilized total membranes by nickel affinity chromatography. Briefly, total membranes were loaded on nickel-nitrilotriacetic acid (Ni-NTA) agarose columns (Qiagen) previously equilibrated with a buffer containing 20 mM imidazole. To remove unbound proteins, the column was washed four times each with buffers containing 20 mM and 30 mM imidazole. His-tagged proteins bound to the column were eluted over six fractions with an elution buffer containing 250 mM imidazole.

Alternatively, AKTA purifier (Amersham Biosciences, Sweden) was employed for protein purifications. Solubilized membrane proteins were first filtered through 0.45 µm and 0.22 µm filters, and then loaded on a His-Trap HP column (GE Healthcare) previously equilibrated with a buffer containing 20 mM imidazole. Unbound proteins were removed by washing the column ten times each with buffers containing 20 mM and 30 mM imidazole. To elute proteins bound to the column, gradient elutions with an incremental increase in imidazole concentration of the elution buffer were used.

Mouse Immunizations:

Imidazole was removed by an overnight round of dialysis followed by 2 2-hour rounds in a dialysis buffer composed of 250 ml PBS containing 0.25% DDM. Proteins were quantified using a DC kit (biorad) after which the samples were diluted to approximately 6 µg/ml and 0.6 µg injected per mouse. Two groups of 10 mice were injected either unglycosylated ComP or CPS-conjugated ComP. Sera from the mice were obtained before immunization, 7 and 21 days post immunization. A booster dose was given on the $14^{th}$ day.

Whole Cell ELISAs.

S. pneumoniae serotype 14 (Statens Serum Institut, Denmark) was grown overnight in BHI broth at 37° C. with 5% CO2 aerobic conditions. Cells were washed in 1×PBS and OD was adjusted to 0.6. Cells were then heat inactivated by incubation at 60° C. for 2 h followed by immobilizing on Corning high binding 96 well plates (50 µL/well). Plates were incubated overnight at 4° C. The following day, wells were washed three times with 1×PBS (100 µL/well) before blocking with 5% skimmed milk for 2 h. The wells were washed three times with PBS. Plates were then incubated for an hour at room temperature with mouse sera (100 µL/well) at a 1:500 dilution in 2.5% skimmed milk in PBST. For the positive control, a commercial rabbit polyclonal antibody against CPS of serotype 14 was used (Statens serum institute). Negative control wells were treated with skimmed milk instead of the primary antibody. After incubation with the primary antibody, wells were washed three times with PBS. This was followed by a 1-hour incubation with secondary HRP-conjugated antibodies (100 µL/well). Antibodies employed were the anti mouse IgM (1:10000), anti mouse IgG (1:10000) and anti rabbit (1:5000) HRP-conjugated antibodies diluted in 2.5% skimmed milk in PBST. After incubation, the wells were washed three times with PBS and 100 µL of the chromogenic substrate TMB (Cell Signaling Technology) was added to each well and the plate was incubated at room temperature for 5 minutes after which the absorbance at 650 nm was measured using a BioTek™ plate reader.

Bacterial surface glycans such as capsular polysaccharides (CPS) and O antigens are good vaccine candidates as they were demonstrated to provide glycan-specific protection. Said glycans when used alone elicit T cell-independent immune responses, with no memory cells being formed, and subsequent booster doses are required to sustain protection. As a result, the efficacy of glycan-only vaccines has been well documented in adults under 55 years. However, children <5 respond poorly, if at all, to these vaccines, which has been attributed to the low expression of CD21 on the surface of B cells in the spleen and blood at this age. In the elderly, polysaccharide vaccines are less effective due to the physiological age-associated atrophy of haematopoietic tissue and primary lymphoid organs, causing a decreased production of B and T cells (Griffioen et al., 1991; Simell et al., 2008) (Reviewed by Pace, 2013).

Conjugate vaccines, where surface glycans are linked to immunogenic proteins, have greatly reduced incidence of diseases, compared to glycan-only vaccines. In conjugate vaccines, surface glycans are conjugated to immunogenic proteins, and this elicits T cell-dependent immune responses, which are stronger immune responses that are also associated with the development of memory cells for subsequent infections. The efficacy of conjugate vaccines was demonstrated in children <5 years, which could be attributed to the fact that infant T cells show adult immunophenotypes and mount equally robust immune responses to conjugate vaccine antigens (Timens et al., 1989). For these reasons, conjugate vaccines are gaining momentum in the vaccine market (reviewed by Pace, 2013).

Most conjugate vaccines in the market today are synthesized by chemically conjugating glycans to proteins, which is an expensive process with numerous drawbacks (Dick and Beurret, 1989; Peeters et al., 2003; Lees et al., 2006). Exploiting OTases to perform this conjugation in bacteria has been suggested as a method for cutting vaccine manufacturing costs and improving the efficiency of the process (Terra et al., 2012). OTases heterologously expressed in a bacterial expression system (usually engineered *Escherichia coli* strains) transfer lipid-linked glycans to acceptor proteins, after which the glycoprotein is subsequently purified. Examples of OTase-conjugated vaccines include, but are not limited to, those against *Pseudomonas aeruginosa, Francisella tularensis, Burkholderia pseudomallei, Shigella flexneri* and *Shigella dysenteriae* (Horzempa et al., 2008; Cuccui et al., 2013; Garcia-Quintanilla et al., 2014; Kampf et al., 2015; Ravenscroft et al., 2015).

To date, the best-characterized OTases for producing conjugate vaccines are the *Campylobacter* N-OTase PglB (CjPglB) and the O-OTases TfpO/Pilo from *Pseudomonas aeruginosa* and NmPglL from *Neisseria meningitidis*. The mentioned OTases were found be specific towards the glycans transferred and the range of acceptor proteins they glycosylate.

Regarding acceptor proteins, CjPglB transfers glycans to Asn residues of acceptor proteins that lie in the sequon D/EX$_1$NX$_2$S/T (SEQ ID NO: 110), with X being any amino acid except proline, and the residue in the −2 position being acidic, namely glutamic acid (D) or aspartic acid (E) (Kowarik et al., 2006). A DQNAT sequon (SEQ ID NO: 111) was identified to be the optimal sequon for glycosylation by CjPglB (Chen et al., 2007). Insertion of this sequon, termed "glycotag", at N or C termini of unglycosylated proteins such as *E. coli* maltose-binding protein MalE induced glycosylation by CjPglB (Fisher et al., 2010).

No consensus sequence has been identified for the glycosylation site of O-OTases to date. Instead, the glycosylated residues identified were in low complexity regions, with an abundance of serine, proline and alanine residues (Vik et al., 2009). This means that acceptor proteins are limited to the natural substrates of O-OTases, which in case of TfpO is the *P. aeruginosa* strain 1244 Type IV pilin PilA and in case of NmPglL is a wide range of proteins. However, a similar idea to the N-glycosylation glycotags has been employed in *P. aeruginosa*, where TfpO was able to glycosylate other proteins with the C terminal 15 residues of PilA (where the glycosylation site lies) fused to their C terminal (Qutyan et al., 2010).

With regards to glycan specificity, CjPglB requires an acetamido group at C-2 of the reducing end for glycan transfer to acceptor proteins. Furthermore, CjPglB was shown to only transfer glycans with N-acetylated sugar residues at the reducing end of the glycan such as FucNAc, GalNAc, GlcNAc and Bac (Feldman et al., 2005; Wacker et al., 2006). Additionally, CjPglB was demonstrated to transfer *Burkholderia. pseudomallei* O polysaccharide II, the equivalent of O antigen. This glycan is a polymer of disaccharide repeating subunits composed of glucose and O-acetyl deoxytalose (Garcia-Quintanilla et al., 2014).

TfpO/Pilo was demonstrated to transfer multiple *Pseudomonas* O antigens, all of which are either tri or tetrasaccharides with FucNAc at the reducing end, to PilA. TfpO also transferred the *E. coli* O157 antigen, a tetrasaccharide with GalNAc at the reducing end (DiGiandomenico et al., 2002; Horzempa et al., 2006). Furthermore, TfpO was demonstrated to only transfer short chain oligosaccharides of the *E. coli* O7 antigen, a pentasaccharide with GlcNAc at the reducing end, greatly limiting its potential for the conjugate vaccine industry apart from *Pseudomonas* conjugate vaccines (Faridmoayer et al., 2007).

NmPglL on the other hand displayed a more relaxed glycan specificity than TfpO, and was demonstrated to transfer sugars with N-acetylated glycans at the reducing end as well as glycans with Gal residues at the reducing end, characteristic of the *Salmonella enterica S. typhimurium* O antigen (which could not be transferred by CjPglB). In addition to having different glycan and protein specificities, the O-OTases NmPglL and TfpO are sequentially and phylogenetically distinct, which suggests that they comprise two distinct classes of O-OTases. PglL-like OTases appear to be far more superior and with more potential in glycoengineering than TfpO-like OTases, given their ability to transfer longer oligosaccharides and their more relaxed glycan specificity.

A limitation of all characterized OTases to date is that none of them are able to transfer glycans with glucose residues at the reducing end. Such glycans are characteristic of the capsular polysaccharides of members of the genus *Streptococcus*, an example of which being *S. pneumoniae*.

*Streptococcus pneumoniae*, or the Pneumococcus, is one of the leading causes of bacterial meningitis in infants and children. Children under 5, the elderly and immunocompromised are at a particular high risk of community-acquired pneumococcal infections (Reviewed by Watson et al., 1993). In 2000, conservative estimates of Pneumococcus infections predicted 14.5 million cases. Pneumococcus-associated mortalities in children under 5 years are estimated to be 826000 annually, accounting for approximately 11% of mortalities in children under 5 (O'Brien et al., 2009). More than 90 serotypes have been identified for the Pneumococcus, each possessing a structurally and immunogenically distinct polysaccharide capsule that is the basis of pneumococcus vaccines (Lund, 1970; Kadioglu et al., 2008). Pneumococcus conjugate vaccines available in the market are produced by chemical conjugations of CPS to the modified diphtheria toxin CRM$_{197}$, which, despite its exceptional efficacy, is significantly more expensive than polysaccharide-only vaccines according to the CDC vaccine price list. This has led the slow implementation of Pneumococcus vaccine programs by low-income countries without external aid (Wenger, 2001; Weinberger et al., 2011).

As a result of this, an OTase capable of biologically conjugating the *Streptococcus* CPS to acceptor proteins, such as that of the Pneumococcus, would revolutionize immunization against this organism, leading to significantly cheaper vaccines and ultimately leading to a reduction in disease burden and child deaths especially in low-income countries.

In the present example there is provided an O-OTase that appears to constitute a novel class of O-OTases. The OTase is called PglL$_{ComP}$ and was identified in the non-pathogenic strain *Acinetobacter baylyi* (Harding et al., 2015). This OTase is phylogenetically and sequentially similar to PglL-like OTases and transfers similar glycans (FIG. 12). However, it only has one acceptor protein, the type IV pilin ComP, a feature similar to the TfpO-like OTases. The present example demonstrates that PglL$_{ComP}$ has the ability to transfer CPS from *S. pneumoniae* serotype 14—which has a glucose residue at the reducing end- to ComP, whereas all previously identified OTases are unable to transfer sugars containing glucose at the reducing end (FIG. 13). This finding opens the door to a wide range of applications of PglL$_{ComP}$ in manufacturing *Streptococcus* conjugate vaccines, including but not limited to *S. pneumoniae* but to other Streptococci, such as the swine pathogen *S. suis* and the Bovine pathogen *S. uberis*.

Example 3

In the present example there is provided evidence that injection of CPS14-conjugated to ComP via PglL$_{ComP}$ in *E. coli* mounts an IgG immune response against *S. pneumoniae* serotype 14 capsule.

In this example, it was sought to determine whether ComP conjugated with the *S. pneumoniae* serotype 14 capsular polysaccharide would generate an immunogenic response in a murine model. Overexpressed his-tagged ComP either conjugated to CPS or in its unglycosylated form were purified by Nickel affinity chromatography from *E. coli* SDB1 detergent-solubilized total membranes. For immunization, 60 ng of CPS-conjugated ComP were used per mouse (n=10) and as a control group, mice were immunized with 60 ng of unglycosylated ComP each (n=10). A booster dose of the glycoprotein was administered on day 14 and pre immune sera and post immune sera (day 7 and day 21) were collected. To determine if there was an immunogenic response, we performed whole cell ELISAs by immobilizing heat-killed *S. pneumoniae* serotype 14 on 96 well plates. Pre immune and post-immune sera from day 7 did not produce and immune response to the whole cells. Post immune sera from day 21 of the mice injected with CPS-conjugated ComP demonstrated marginal IgM and significant IgG based immune responses against this serotype. An IgG immune response was not seen with the negative control mice injected with the glycosylated ComP (FIGS. 14, 15, 16A). No reactivity was seen in the negative control wells (not treated with a primary antibody) whereas strong reactivity was seen in wells treated with a commercially available anti CPS14 antibody (SSI Denmark) (FIG. 16B). Similar results were seen in Western blots, where *S. pneumoniae* CPS expression from *E. coli* CLM37 was probed for with mice sera (FIG. 17).

TABLE 6

Primers used in the present application

| Primer Set | | Sequence |
|---|---|---|
| 1 | F | AGAATACTTGCATAGTGACAGGTTACAG (SEQ ID NO: 1) |
|   | R | GTTATGGCGGCGGTGGAGGTC (SEQ ID NO: 2) |
| 2 | F | CAAAAAGCTTATATAAAAACATACATACAATCTTTGGGGAA AAGGCTATGATTCCGGGGATCCGTCGACC (SEQ ID NO: 3) |
|   | R | GGATTGACCTCTCTTTTTTATTTCTAAAATTACGATGCTAC AAATGATTGTGTAGGCTGGAGCTGCTTCG (SEQ ID NO: 4) |
| 3 | F | GCGGGATCCGCAAATTGGTGATGTGATGTCTCG (SEQ ID NO: 5) |
|   | R | GCGGGTACCGCTGCGAGGAATAAAAAGAATACT (SEQ ID NO: 6) |

TABLE 6-continued

Primers used in the present application

| Primer Set | | Sequence |
|---|---|---|
| 4 | F | GCGGGATCCGCAAATTGGTGATGTGATGTCTCG (SEQ ID NO: 7) |
|   | R | GCGGGTACCTCGTATTGTGAACTAGACCATCCT (SEQ ID NO: 8) |
| 5 | F | GCGGGATCCGCAAATTGGTGATGTGATGTCTCG (SEQ ID NO: 9) |
|   | R | GCGGGTACCGCTGCGAGGAATAAAAAGAATACT (SEQ ID NO: 10) |
| 6 | F | AGAATACTTGCATAGTGACAGGTTACAG (SEQ ID NO: 11) |
|   | R | CGCATTTATATTTGGGGATTACTC (SEQ ID NO: 12) |
| 7 | F | CTTCCATGTATAATTCTTCTCAAGTTTTTGGTCTGTAACCT GTCACTATGATTCCGGGGATCCGTCGACC (SEQ ID NO: 13) |
|   | R | AAAATCCCCTTGAAAACAAGGGGATTTTTTATTTATCTTT TAATAATTGTGTAGGCTGGAGCTGCTTCG (SEQ ID NO: 14) |
| 8 | F | CTTCCTCAATCATTTGTAGCAGCGTAATTTTAGAAATAAAAA AG (SEQ ID NO: 15) |
|   | R | CTTTTTTATTTCTAAAATTACGCTGCTACAAATGATTGAGGA AG (SEQ ID NO: 16) |
| 9 | F | ATGAAAAAACTTGAGCACCTTGC (SEQ ID NO: 17) |
|   | R | TGTTTGCTCTTATTTCTACTG (SEQ ID NO: 18) |
| 10 | F | TTGTCATTTATAAAGTTAGTCAC (SEQ ID NO: 19) |
|    | R | TGTACACCTGATTTAATATTCTA (SEQ ID NO: 20) |
| 11 | F | GAAATAAGAGCAAACAATTCCGGGGATCCGTCGACC (SEQ ID NO: 21) |
|    | R | CTTTATAAATGACAATGTAGGCTGGAGCTGCTTCG (SEQ ID NO: 22) |
| 12 | F | CTCAAGTTTTTTCATCGCCATGGCGGCCGGGAGCATG (SEQ ID NO: 23) |
|    | R | AAAATCAGGTGTACAACTAGTGAATTCGCGGCCGCCTGCA (SEQ ID NO: 24) |
| 13 | F | CGTCCCCAAAAGCGTGAA (SEQ ID NO: 25) |
|    | R | TTAGGCAAATTTCGAAGCGTGAT (SEQ ID NO: 26) |
| 14 | F | GCGCCCGGGATAAGTGCTCAATTGATGG (SEQ ID NO: 27) |
|    | R | GGTACCGAGATCCCAAACCAGCAAC (SEQ ID NO: 28) |
| 15 | F | ACTAGTGAATTCGCGGCCGCCTGCA (SEQ ID NO: 29) |
|    | R | CGCCATGGCGGCCGGGAGCATG (SEQ ID NO: 30) |
| 16 | F | ATTCCGGGGATCCGTCGACC (SEQ ID NO: 31) |
|    | R | TGTAGGCTGGAGCTGCTTCG (SEQ ID NO: 32) |
| 17 | F | CCGGCCGCCATGGCGATGACGATTGGTTTAATTTTTTC (SEQ ID NO: 33) |
|    | R | ACGGATCCCCGGAATCATACTTGTAAAAAAAAAAGTATTT (SEQ ID NO: 34) |
| 18 | F | CAGCTCCAGCCTACAATGGAAGAAAATTCTTTATTAATTT (SEQ ID NO: 35) |
|    | R | CGCGAATTCACTAGTTTAAACATATTTTTCCCATTTC (SEQ ID NO: 36) |
| 19 | F | CCGGCCGCCATGGCGATGACTCCTGCCGGAGG (SEQ ID NO: 37) |
|    | R | ACGGATCCCCGGAATTTAATAAAGAATTTTCTTCCATTTAC (SEQ ID NO: 38) |
| 20 | F | CAGCTCCAGCCTACAATAGTAGGACTAAAAAAATGATTTCG (SEQ ID NO: 39) |
| 20 | R | CGCGAATTCACTAGTTTATTTATATAACCCTTTTTCTTTC (SEQ ID NO: 40) |

TABLE 6-continued

Primers used in the present application

| Primer Set | | Sequence |
|---|---|---|
| 21 | F | CGGCCGCCATGGCGATGTTTAAAAATGTATTAATTACTGG (SEQ ID NO: 41) |
|    | R | ACGGATCCCCGGAATCATTTATTTATATAACCCTTTTCT (SEQ ID NO: 42) |
| 22 | F | CAGCTCCAGCCTACAATAAATTTAAAATATTCATAAATCT (SEQ ID NO: 43) |
|    | R | CGCGAATTCACTAGTTTATAATTTAAGTTCTTGAATCAAC (SEQ ID NO: 44) |
| 23 | F | CTACATTGTTTATTTTTACCAGAA (SEQ ID NO: 45) |
|    | R | GAAGCTTGAAGTTATCCACGAA (SEQ ID NO: 46) |
| 24 | F | CATCAAAAATACCAGCCTAAATTATC (SEQ ID NO: 47) |
|    | R | CCATTGTTTGAAATTATTTAGGG (SEQ ID NO: 48) |
| 25 | F | CATCAAAAATACCAGCCTAAATTATC (SEQ ID NO: 49) |
|    | R | GAAGAAAATTCTTTATTAATTTCTG (SEQ ID NO: 50) |
| 26 | F | CATCAAAAATACCAGCCTAAATTATC (SEQ ID NO: 51) |
|    | R | GAAAAAGGGTTATATAAATAAATG (SEQ ID NO: 52) |
| 27 | F | GCGCCCGGGCTACATTGTTTATTTTTACCAGAA (SEQ ID NO: 53) |
|    | R | GCGGGTACCACCATCATTGACTACTAAGACCTC (SEQ ID NO: 54) |
| 28 | F | GCGCCCGGGCTACATTGTTTATTTTTACCAGAA (SEQ ID NO: 55) |
|    | R | GCGGGTACCTTCTACATCCAATACCAGTCGT (SEQ ID NO: 56) |
| 29 | F | GCGCCCGGGCTACATTGTTTATTTTTACCAGAA (SEQ ID NO: 57) |
|    | R | GCGGGTACCGAAGCTTGAAGTTATCCACGAA (SEQ ID NO: 58) |
| 30 | F | GCGCCCGGGCCGAAGCAGGGTGGGTGTTAGT (SEQ ID NO: 59) |
|    | R | GCGGGTACCTTAGTGGTGGTGGTGGTGTTGAGCTACTGAAAACTCAATAC (SEQ ID NO: 60) |
| 31 | F | GCCATATGGCTTATCAAAACTATATTGCTAAATCTC (SEQ ID NO: 61) |
|    | R | GCGGATCCCTCTTTTTTATTTCTAAAATTACGATGCT (SEQ ID NO: 62) |
| 32 | F | ATAGGATCCATGAATGCACAAAAGGGTTTTACC (SEQ ID NO: 63) |
|    | R | TATGTCGACTCAGTGGTGGTGGTGGTGACCACGACATTCTGATGG (SEQ ID NO: 64) |
| 33 | F | ATATGGATCCGTGGTTGATAGTAGTACTATATGG (SEQ ID NO: 65) |
|    | R | ATATGTCGACTCAGTGGTGGTGGTGGTGATATTCTATTGACAAAATTTTAACTTAGG (SEQ ID NO: 66) |
| 34 | F | ATATGGATCCGTGGCTGGTTCCCCGCGTGTGTATAATAGC (SEQ ID NO: 67) |
|    | R | ATATGTCGACTTAGTGGTGGTGGTGGTGCTTGGATGACTCTACAGCAGAAGC (SEQ ID NO: 68) |
| 35 | F | ACTGGGATCCATGTTAAAAAAAATTATTCTATTTC (SEQ ID NO: 69) |
|    | R | ACTGGTCGACTAAGTGGTGGTGGTGGTGGTGGTGGTGGTGAGGAATTTTTGAGGTTGGTAC (SEQ ID NO: 70) |
| 36 | F | ACTGGGATCCATGCAAGTATTCTTTCTGTTC (SEQ ID NO: 71) |
|    | R | ACTGGTCGACTAAGTGGTGGTGGTGGTGGTGGTGGTGGTTTATTTTTTAACAACTCTGCC (SEQ ID NO: 72) |
| 37 | F | GGTGGACGTGGAGGAG (SEQ ID NO: 73) |
|    | R | CTTGCTTGGGTTACATCAGTGCT (SEQ ID NO: 74) |
| 38 | F | AATTATTGTACAGCCTTTTG (SEQ ID NO: 75) |
|    | R | CATCATCATCATCATCACTAATATTAAAAATGTATAAAAAACACC (SEQ ID NO: 76) |
| 39 | F | CCAGTTGAATTACTTCCTCAAGCATTTGTAGCATCGTAAT (SEQ ID NO: 77) |
|    | R | ATTACGATGCTACAAATGCTTGAGGAAGTAATTCAACTGG (SEQ ID NO: 78) |

REFERENCES

Aas, F. E., Egge-Jacobsen, W., Winther-Larsen, H. C., Løvold, C., Hitchen, P. G., Dell, A., & Koomey, M. (2006). Neisseria gonorrhoeae type IV pili undergo multisite, hierarchical modifications with phosphoethanolamine and phosphocholine requiring an enzyme structurally related to lipopolysaccharide phosphoethanolamine transferases. The Journal of Biological Chemistry 281(38): 27712-23.

Abd-El-Haleem, D., Moawad, H., Zaki, E. A., & Zaki, S. (2002). Molecular characterization of phenol-degrading bacteria isolated from different Egyptian ecosystems. Microbial Ecology 43(2): 217-24.

Arroyo, L. A., Mateos, I., Gonzalez, V., & Aznar, J. (2009). In vitro activities of tigecycline, minocycline, and colistin-tigecycline combination against multi- and pandrug-resistant clinical isolates of Acinetobacter baumannii group. Antimicrobial Agents and Chemotherapy 53(3): 1295-6.

Balonova, L., Mann, B. F., Cerveny, L., Alley, W. R., Chovancova, E., Forslund, A.-L., . . . Stulik, J. (2012). Characterization of protein glycosylation in Francisella tularensis subsp. holarctica: identification of a novel glycosylated lipoprotein required for virulence. Molecular & Cellular Proteomics: MCP 11(7): M111.015016.

Bentley, S. D., Aanensen, D. M., Mavroidi, A., Saunders, D., Rabbinowitsch, E., Collins, M., et al. (2006) Genetic analysis of the capsular biosynthetic locus from all 90 pneumococcal serotypes. PLoS Genet 2: e31.

Børud, B., Viburiene, R., Hartley, M. D., Paulsen, B. S., Egge-Jacobsen, W., Imperiali, B., & Koomey, M. (2011). Genetic and molecular analyses reveal an evolutionary trajectory for glycan synthesis in a bacterial protein glycosylation system. Proceedings of the National Academy of Sciences of the United States of America 108(23): 9643-8.

Boucher, C. A., Barberis, P. A., & Demery, D. A. (1985). Transposon Mutagenesis of Pseudomonas solanacearum: Isolation of Tn5-Induced Avirulent Mutants. Microbiology 131(9): 2449-2457.

Brzoska, A. J., Hassan, K. A., de Leon, E. J., Paulsen, I. T., & Lewis, P. J. (2013). Single step selection of drug resistant Acinetobacter baylyi ADP1 mutants reveals a functional redundancy in the recruitment of multidrug efflux systems. PLoS One 8(2): e56090.

Cagatay, T. I., & Hickford, J. G. H. (2008). Glycosylation of type-IV fimbriae of Dichelobacter nodosus. Veterinary Microbiology 126(1-3): 160-7.

Carruthers, M. D., Nicholson, P. A., Tracy, E. N., & Munson, R. S. (2013). Acinetobacter baumannii Utilizes a Type VI Secretion System for Bacterial Competition. PLoS One 8(12): e59388.

Castric, P. (1995). pilO, a gene required for glycosylation of *Pseudomonas aeruginosa* 1244 pilin. *Microbiology* 141: 1247-54.

Charbonneau, M.-E., Girard, V., Nikolakakis, A., Campos, M., Berthiaume, F., Dumas, F., . . . Mourez, M. (2007). O-linked glycosylation ensures the normal conformation of the autotransporter adhesin involved in diffuse adherence. *Journal of Bacteriology* 189(24): 8880-9.

Chen, M. M., Glover, K. J., and Imperiali, B. (2007) From peptide to protein: comparative analysis of the substrate specificity of N-linked glycosylation in *C. jejuni*. *Biochemistry* 46: 5579-85.

Choi, A. H. K., Slamti, L., Avci, F. Y., Pier, G. B., & Maira-Litran, T. (2009). The pgaABCD locus of *Acinetobacter baumannii* encodes the production of poly-beta-1-6-N-acetylglucosamine, which is critical for biofilm formation. *Journal of Bacteriology* 191(19): 5953-63.

Choi, C. H., Hyun, S. H., Lee, J. Y., Lee, J. S., Lee, Y. S., Kim, S. A., . . . Lee, J. C. (2008). *Acinetobacter baumannii* outer membrane protein A targets the nucleus and induces cytotoxicity. *Cellular Microbiology* 10(2): 309-19.

Comer, J. E., Marshall, M. A., Blanch, V. J., Deal, C. D., & Castric, P. (2002). Identification of the *Pseudomonas aeruginosa* 1244 pilin glycosylation site. *Infection and Immunity* 70(6): 2837-45.

Cote, J.-P., Charbonneau, M.-E., & Mourez, M. (2013). Glycosylation of the *Escherichia coli* TibA self-associating autotransporter influences the conformation and the functionality of the protein. *PloS One* 8(11): e80739.

Coyne, M. J., Fletcher, C. M., Chatzidaki-Livanis, M., Posch, G., Schaffer, C., & Comstock, L. E. (2013). Phylum-wide general protein O-glycosylation system of the *Bacteroidetes*. *Molecular Microbiology* 88(4): 772-83.

Cuccui, J., Thomas, R. M., Moule, M. G., D'Elia, R. V, Laws, T. R., Mills, D. C., et al. (2013) Exploitation of bacterial N-linked glycosylation to develop a novel recombinant glycoconjugate vaccine against *Francisella tularensis*. *Open Biol* 3: 130002.

De Berardinis, V., Vallenet, D., Castelli, V., Besnard, M., Pinet, A., Cruaud, C., . . . Weissenbach, J. (2008). A complete collection of single-gene deletion mutants of *Acinetobacter baylyi* ADP1. *Molecular Systems Biology* 4: 174.

Dick, W. E., and Beurret, M. (1989) Glycoconjugates of bacterial carbohydrate antigens. A survey and consideration of design and preparation factors. *Contrib Microbiol Immunol* 10: 48-114.

DiGiandomenico, A., Matewish, M. J., Bisaillon, A., Stehle, J. R., Lam, J. S., and Castric, P. (2002) Glycosylation of *Pseudomonas aeruginosa* 1244 pilin: glycan substrate specificity. *Mol Microbiol* 46: 519-30.

Egge-Jacobsen, W., Salomonsson, E. N., Aas, F. E., Forslund, A.-L., Winther-Larsen, H. C., Maier, J., . . . Koomey, M. (2011). O-linked glycosylation of the PilA pilin protein of *Francisella tularensis*: identification of the endogenous protein-targeting oligosaccharyltransferase and characterization of the native oligosaccharide. *Journal of Bacteriology* 193(19): 5487-97.

Faridmoayer, A., Fentabil, M. A., Mills, D. C., Klassen, J. S., & Feldman, M. F. (2007). Functional characterization of bacterial oligosaccharyltransferases involved in O linked protein glycosylation. *Journal of Bacteriology* 189(22): 8088-98.

Feldman, M. F., Wacker, M., Hernandez, M., Hitchen, P. G., Marolda, C. L., Kowarik, M., . . . Aebi, M. (2005). Engineering N-linked protein glycosylation with diverse O antigen lipopolysaccharide structures in *Escherichia coli*. *Proceedings of the National Academy of Sciences of the United States of America* 102(8): 3016-21.

Fisher, A. C., Haitjema, C. H., Guarino, C., Celik, E., Endicott, C. E., Reading, C. A., et al. (2010) Production of Secretory and Extracellular N-Linked Glycoproteins in *Escherichia coli*. *Appl Environ Microbiol* 77: 871-881.

Garcia-Quintanilla, F., Iwashkiw, J. A., Price, N. L., Stratilo, C., and Feldman, M. F. (2014) Production of a recombinant vaccine candidate against *Burkholderia pseudomallei* exploiting the bacterial N-glycosylation machinery. *Front Microbiol* 5: 381.

Gebhart, C., Ielmini, M. V., Reiz, B., Price, N. L., Aas, F. E., Koomey, M., & Feldman, M. F. (2012). Characterization of exogenous bacterial oligosaccharyltransferases in *Escherichia coli* reveals the potential for O-linked protein glycosylation in *Vibrio cholerae* and *Burkholderia thailandensis*. *Glycobiology* 22(7): 962-74.

Gordon, N. C., & Wareham, D. W. (2010). Multidrug-resistant *Acinetobacter baumannii*: mechanisms of virulence and resistance. *International Journal of Antimicrobial Agents* 35(3): 219-26.

Gottig, S., Gruber, T. M., Higgins, P. G., Wachsmuth, M., Seifert, H., & Kempf, V. A. J. (2014). Detection of pan drug-resistant *Acinetobacter baumannii* in Germany. *The Journal of Antimicrobial Chemotherapy* 69(9): 2578-9.

Griffioen, A. W., Rijkers, G. T., Janssens-Korpela, P., and Zegers, B. J. (1991) Pneumococcal polysaccharides complexed with C3d bind to human B lymphocytes via complement receptor type 2. *Infect Immun* 59: 1839-45.

Gross, J., Grass, S., Davis, A. E., Gilmore-Erdmann, P., Townsend, R. R., & St Geme, J. W. (2008). The *Haemophilus influenzae* HMW1 adhesin is a glycoprotein with an unusual N-linked carbohydrate modification. *The Journal of Biological Chemistry* 283(38): 26010-5.

Harding, C. M., Tracy, E. N., Carruthers, M. D., Rather, P. N., Actis, L. A., & Munson, R. S. (2013). *Acinetobacter baumannii* strain M2 produces type IV pili which play a role in natural transformation and twitching motility but not surface-associated motility. *mBio* 4(4): e00360-13.

Harding, C. M., Nasr, M. A., Kinsella, R. L., Scott, N. E., Foster, L. J., Weber, B. S., et al. (2015) *Acinetobacter* strains carry two functional oligosaccharyltransferases, one devoted exclusively to type IV pilin, and the other one dedicated to O-glycosylation of multiple proteins. *Mol Microbiol*.

Horzempa, J., Dean, C. R., Goldberg, J. B., and Castric, P. (2006) *Pseudomonas aeruginosa* 1244 pilin glycosylation: glycan substrate recognition. *J Bacteriol* 188: 4244-52.

Horzempa, J., Held, T. K., Cross, A. S., Furst, D., Qutyan, M., Neely, A. N., and Castric, P. (2008) Immunization with a *Pseudomonas aeruginosa* 1244 pilin provides O-antigen-specific protection. *Clin Vaccine Immunol* 15: 590-7.

Hu, D., Liu, B., Dijkshoorn, L., Wang, L., & Reeves, P. R. (2013). Diversity in the major polysaccharide antigen of *Acinetobacter baumannii* assessed by DNA sequencing, and development of a molecular serotyping scheme. *PloS One* 8(7): e70329.

Hug, I., & Feldman, M. F. (2011). Analogies and homologies in lipopolysaccharide and glycoprotein biosynthesis in bacteria. *Glycobiology* 21(2): 138-51.

Ielmini, M. V, & Feldman, M. F. (2011). *Desulfovibrio desulfuricans* PglB homolog possesses oligosaccharyltransferase activity with relaxed glycan specificity and distinct protein acceptor sequence requirements. *Glycobiology* 21(6): 734-42.

Iwashkiw, J. A., Seper, A., Weber, B. S., Scott, N. E., Vinogradov, E., Stratilo, C., . . . Feldman, M. F. (2012). Identification of a General O-linked Protein Glycosylation System in *Acinetobacter baumannii* and Its Role in Virulence and Biofilm Formation. *PLoS Pathogens* 8(6): e1002758.

Iwashkiw, J. A., Vozza, N. F., Kinsella, R. L., & Feldman, M. F. (2013). Pour some sugar on it: the expanding world of bacterial protein O-linked glycosylation. *Molecular Microbiology* 89(1): 14-28.

Kadioglu, A., Weiser, J. N., Paton, J. C., and Andrew, P. W. (2008) The role of *Streptococcus pneumoniae* virulence factors in host respiratory colonization and disease. *Nat Rev Microbiol* 6: 288-301.

Kampf, M. M., Braun, M., Sirena, D., Ihssen, J., Thony-Meyer, L., and Ren, Q. (2015) In vivo production of a novel glycoconjugate vaccine against *Shigella flexneri* 2a in recombinant *Escherichia coli*: identification of stimulating factors for in vivo glycosylation. *Microb Cell Fact* 14: 12.

Kowarik, M., Young, N. M., Numao, S., Schulz, B. L., Hug, I., Callewaert, N., et al. (2006) Definition of the bacterial N-glycosylation site consensus sequence. *EMBO J* 25: 1957-66.

Kus, J. V, Tullis, E., Cvitkovitch, D. G., & Burrows, L. L. (2004). Significant differences in type IV pilin allele distribution among *Pseudomonas aeruginosa* isolates from cystic fibrosis (CF) versus non-CF patients. *Microbiology* 150: 1315-26.

Lees, A., Sen, G., and LopezAcosta, A. (2006) Versatile and efficient synthesis of protein-polysaccharide conjugate vaccines using aminooxy reagents and oxime chemistry. *Vaccine* 24: 716-729.

Lees-Miller, R. G., Iwashkiw, J. A., Scott, N. E., Seper, A., Vinogradov, E., Schild, S., & Feldman, M. F. (2013). A common pathway for O-linked protein-glycosylation and synthesis of capsule in *Acinetobacter baumannii*. *Molecular Microbiology* 89(5): 816-30.

Lithgow, K. V., Scott, N. E., Iwashkiw, J. A., Thomson, E. L. S., Foster, L. J., Feldman, M. F., & Dennis, J. J. (2014). A general protein O-glycosylation system within the *Burkholderia cepacia* complex is involved in motility and virulence. *Molecular Microbiology* 92(1): 116-137.

Logan, S. M. (2006). Flagellar glycosylation—a new component of the motility repertoire? *Microbiology* 152: 1249-62.

Lund, E. (1970) On the nomenclature of the pneumococcal types. *Int J Syst Bacteriol* 20: 321-323.

Mara, K., Decorosi, F., Viti, C., Giovannetti, L., Papaleo, M. C., Maida, I., . . . Fani, R. (2012). Molecular and phenotypic characterization of *Acinetobacter* strains able to degrade diesel fuel. *Research in Microbiology* 163(3): 161-72.

Marchler-Bauer A., Bryant S H. (2004). CD-Search: protein domain annotations on the fly. *Nucleic Acids Research* 32(W): 327-331.

Marchler-Bauer A. et al. (2009). CDD: specific functional annotation with the Conserved Domain Database. *Nucleic Acids Research* 37(D): 205-10.

Marchler-Bauer A. et al. (2011). CDD: a Conserved Domain Database for the functional annotation of proteins. *Nucleic Acids Research* 39(D): 225-9.

Mescher, M. F., & Strominger, J. L. (1976). Structural (shape-maintaining) role of the cell surface glycoprotein of *Halobacterium salinarium*. *Proceedings of the National Academy of Sciences of the United States of America* 73(8): 2687-91.

Musumeci, M. A., Faridmoayer, A., Watanabe, Y., & Feldman, M. F. (2014). Evaluating the role of conserved amino acids in bacterial O-oligosaccharyltransferases by in vivo, in vitro and limited proteolysis assays. *Glycobiology* 24(1): 39-50.

Neuberger, A. (1938). Carbohydrates in protein: The carbohydrate component of crystalline egg albumin. *The Biochemical Journal* 32(9): 1435-51.

Nguyen, L. C., Taguchi, F., Tran, Q. M., Naito, K., Yamamoto, M., Ohnishi-Kameyama, M., . . . Ichinose, Y. (2012). Type IV pilin is glycosylated in *Pseudomonas syringae* pv. *tabaci* 6605 and is required for surface motility and virulence. *Molecular Plant Pathology* 13(7): 764-74.

Nothaft, H., Scott, N. E., Vinogradov, E., Liu, X., Hu, R., Beadle, B., . . . Szymanski, C. M. (2012). Diversity in the protein N-glycosylation pathways within the *Campylobacter* genus. *Molecular & Cellular Proteomics: MCP* 11(11): 1203-19.

Nothaft, H., & Szymanski, C. M. (2010). Protein glycosylation in bacteria: sweeter than ever. *Nature Reviews. Microbiology* 8(11): 765-78.

O'Brien, K. L., Wolfson, L. J., Watt, J. P., Henkle, E., Deloria-Knoll, M., McCall, N., et al. (2009) Burden of disease caused by *Streptococcus pneumoniae* in children younger than 5 years: global estimates. *Lancet* 374: 893-902.

Olsen, J. V, Macek, B., Lange, O., Makarov, A., Horning, S., & Mann, M. (2007). Higher-energy C-trap dissociation for peptide modification analysis. *Nature Methods* 4(9): 709-12.

Pace, D. (2013) Glycoconjugate vaccines. *Expert Opin Biol Ther* 13: 11-33.

Peeters, C. C. A. M., Lagerman, P. R., Weers, O. de, Oomen, L. A., Hoogerhout, P., Beurret, M., et al. (2003) Preparation of polysaccharide-conjugate vaccines. *Methods Mol Med* 87: 153-74.

Perez, J. M., McGarry, M. A., Marolda, C. L., & Valvano, M. A. (2008). Functional analysis of the large periplasmic loop of the *Escherichia coli* K-12 WaaL O-antigen ligase. *Molecular Microbiology* 70(6): 1424-40.

Porstendorfer, D., Gohl, O., Mayer, F., & Averhoff, B. (2000). ComP, a Pilin-Like Protein Essential for Natural Competence in *Acinetobacter* sp. Strain BD413: Regulation, Modification, and Cellular Localization. *Journal of Bacteriology* 182(13): 3673-3680.

Power, P., & Jennings, M. (2003). The genetics of glycosylation in Gram-negative bacteria. *FEMS Microbiology Letters* 218(2): 211-222.

Power, P. M., Seib, K. L., & Jennings, M. P. (2006). Pilin glycosylation in *Neisseria meningitidis* occurs by a similar pathway to wzy-dependent O-antigen biosynthesis in *Escherichia coli*. *Biochemical and Biophysical Research Communications* 347(4):904-8.

Qutyan, M., Henkel, M., Horzempa, J., Quinn, M., and Castric, P. (2010) Glycosylation of Pilin and Nonpilin Protein Constructs by *Pseudomonas aeruginosa* 1244. *J Bacteriol* 192: 5972-5981.

Rappsilber, J., Mann, M., & Ishihama, Y. (2007). Protocol for micro-purification, enrichment, pre-fractionation and storage of peptides for proteomics using StageTips. *Nature Protocols* 2(8): 1896-906.

Ravenscroft, N., Haeuptle, M. A., Kowarik, M., Fernandez, F. S., Carranza, P., Brunner, A., et al. (2015) Purification and characterization of a *Shigella* conjugate vaccine, produced by glycoengineering *Escherichia coli*. *Glycobiology* cwv077–.

Ruan, X., Loyola, D. E., Marolda, C. L., Perez-Donoso, J. M., & Valvano, M. A. (2012). The WaaL O-antigen lipopolysaccharide ligase has features in common with metal ion-independent inverting glycosyltransferases. *Glycobiology* 22(2): 288-99.

Schulz, B. L., Jen, F. E. C., Power, P. M., Jones, C. E., Fox, K. L., Ku, S. C., . . . Jennings, M. P. (2013). Identification of bacterial protein O oligosaccharyltransferases and their glycoprotein substrates. *PloS One* 8(5):e62768.

Scott, N. E., Kinsella, R. L., Edwards, A. V. G., Larsen, M. R., Dutta, S., Saba, J., . . . Feldman, M. F. (2014). Diversity Within the O-linked Protein Glycosylation Systems of *Acinetobacter* Species. *Molecular & Cellular Proteomics: MCP* 13(9):2354-70.

Scott, N. E., Nothaft, H., Edwards, A. V. G., Labbate, M., Djordjevic, S. P., Larsen, M. R., Cordwell, S. J. (2012). Modification of the *Campylobacter jejuni* N-linked glycan by EptC protein-mediated addition of phosphoethanolamine *The Journal of Biological Chemistry* 287(35): 29384-96.

Scott, N. E., Parker, B. L., Connolly, A. M., Paulech, J., Edwards, A. V. G., Crossett, B., . . . Cordwell, S. J. (2011). Simultaneous glycan-peptide characterization using hydrophilic interaction chromatography and parallel fragmentation by CID, higher energy collisional dissociation, and electron transfer dissociation MS applied to theN-linked glycoproteome of *Campylobacter jejuni*. *Molecular & Cellular Proteomics: MCP* 10(2): M000031-MCP201.

Simell, B., Landenkari, M., Reunanen, A., Kayhty, H., and Vakevainen, M. (2008) Effects of Ageing and Gender on Naturally Acquired Antibodies to Pneumococcal Capsular Polysaccharides and Virulence-Associated Proteins. *Clin Vaccine Immunol* 15: 1391-1397.

Sleytr, U. B. (1975). Heterologous reattachment of regular arrays of glycoproteins on bacterial surfaces. *Nature* 257(5525): 400-402.

Smedley, J. G., Jewell, E., Roguskie, J., Horzempa, J., Syboldt, A., Stolz, D. B., & Castric, P. (2005). Influence of pilin glycosylation on *Pseudomonas aeruginosa* 1244 pilus function. *Infection and Immunity* 73(12): 7922-31.

Szymanski, C. M., Yao, R., Ewing, C. P., Trust, T. J., & Guerry, P. (1999). Evidence for a system of general protein glycosylation in *Campylobacter jejuni*. *Molecular Microbiology* 32(5): 1022-1030.

Tang, G., & Mintz, K. P. (2010). Glycosylation of the collagen adhesin EmaA of *Aggregatibacter actinomycetemcomitans* is dependent upon the lipopolysaccharide biosynthetic pathway. *Journal of Bacteriology* 192(5): 1395-404.

Terra, V. S., Mills, D. C., Yates, L. E., Abouelhadid, S., Cuccui, J., and Wren, B. W. (2012) Recent developments in bacterial protein glycan coupling technology and glycoconjugate vaccine design. *J Med Microbiol* 61: 919-926.

Timens, W., Boes, A., Rozeboom-Uiterwijk, T., and Poppema, S. (1989) Immaturity of the human splenic marginal zone in infancy. Possible contribution to the deficient infant immune response. *J Immunol* 143: 3200-6.

Tsai, C. M., & Frasch, C. E. (1982). A sensitive silver stain for detecting lipopolysaccharides in polyacrylamide gels. *Analytical Biochemistry* 119(1): 115-9.

van Selm, S., van Cann, L. M., Kolkman, M. A. B., van der Zeijst, B. A. M., and Putten, J. P. M. van (2003) Genetic basis for the structural difference between *Streptococcus pneumoniae* serotype 15B and 15C capsular polysaccharides. *Infect Immun* 71: 6192-8.

Vaneechoutte, M., Young, D. M., Ornston, L. N., De Baere, T., Nemec, A., Van Der Reijden, T., . . . Dijkshoorn, L. (2006). Naturally Transformable *Acinetobacter* sp. Strain ADP1 Belongs to the Newly Described Species *Acinetobacter baylyi*. Applied and Environmental Microbiology 72(1): 932-936.

Varki, A. (1993). Biological roles of oligosaccharides: all of the theories are correct. *Glycobiology* 3(2): 97-130.

Vik, A., Aas, F. E., Anonsen, J. H., Bilsborough, S., Schneider, A., Egge-Jacobsen, W., & Koomey, M. (2009). Broad spectrum O-linked protein glycosylation in the human pathogen *Neisseria gonorrhoeae*. Proceedings of the National Academy of Sciences of the United States of America 106(11): 4447-52.

Voisin, S., Kus, J. V, Houliston, S., St-Michael, F., Watson, D., Cvitkovitch, D. G., . . . Burrows, L. L. (2007). Glycosylation of *Pseudomonas aeruginosa* strain Pa5196 type IV pilins with *Mycobacterium*-like alpha-1,5-linked d-Araf oligosaccharides. *Journal of Bacteriology* 189(1): 151-9.

Wacker, M., Feldman, M. F., Callewaert, N., Kowarik, M., Clarke, B. R., Pohl, N. L., et al. (2006) Substrate specificity of bacterial oligosaccharyltransferase suggests a common transfer mechanism for the bacterial and eukaryotic systems. *Proc Natl Acad Sci USA* 103: 7088-93.

Wang, N., Mackenzie, L., De Souza, A. G., Zhong, H., Goss, G., & Li, L. (2007). Proteome profile of cytosolic component of zebrafish liver generated by LC-ESI MS/MS combined with trypsin digestion and microwave-assisted acid hydrolysis. *Journal of Proteome Research* 6(1): 263-72.

Watson, D. A., Musher, D. M., Jacobson, J. W., and Verhoef, J. (1993) A Brief History of the Pneumococcus in Biomedical Research: A Panoply of Scientific Discovery. *Clin Infect Dis* 17: 913-924.

Weber, B. S., Miyata, S. T., Iwashkiw, J. A., Mortensen, B. L., Skaar, E. P., Pukatzki, S., & Feldman, M. F. (2013). Genomic and functional analysis of the type VI secretion system in *Acinetobacter*. *PloS One* 8(1): e55142.

Weinberger, D. M., Malley, R., and Lipsitch, M. (2011) Serotype replacement in disease after pneumococcal vaccination. *Lancet (London, England)* 378: 1962-73.

Wenger, J. (2001) Vaccines for the developing world: current status and future directions. *Vaccine* 19: 1588-1591.

Whitfield, C. (1995). Biosynthesis of lipopolysaccharide O antigens. *Trends in Microbiology* 3(5): 178-185.

Wisplinghoff, H., Paulus, T., Lugenheim, M., Stefanik, D., Higgins, P. G., Edmond, M. B., . . . Seifert, H. (2012). Nosocomial bloodstream infections due to *Acinetobacter baumannii*, *Acinetobacter pittii* and *Acinetobacter nosocomialis* in the United States. *Journal of Infection* 64(3): 282-290.

Yi, E. C., & Hackett, M. (2000). Rapid isolation method for lipopolysaccharide and lipid A from Gram-negative bacteria. *The Analyst* 125(4): 651-656.

Zhou, M., & Wu, H. (2009). Glycosylation and biogenesis of a family of serine-rich bacterial adhesins. *Microbiology* 155: 317-27.

Actis, L. A., Potter, S. A., & Crosa, J. H. (1985). Iron-regulated outer membrane protein OM2 of *Vibrio anguillarum* is encoded by virulence plasmid pJM1. Journal of Bacteriology, 161(2), 736-42.

Aranda, J., Poza, M., Pardo, B. G., Rumbo, S., Rumbo, C., Parreira, J. R., . . . Bou, G. (2010). A rapid and simple method for constructing stable mutants of *Acinetobacter baumannii* BMC Microbiology, 10(1), 279.

Boersema, P. J., Raijmakers, R., Lemeer, S., Mohammed, S., & Heck, A. J. R. (2009). Multiplex peptide stable isotope dimethyl labeling for quantitative proteomics. Nature Protocols, 4(4), 484-94.

Carruthers, M. D., Nicholson, P. A., Tracy, E. N., & Munson, R. S. (2013). Acinetobacter baumannii utilizes a type VI secretion system for bacterial ComPetition. PloS One, 8(3), e59388.

Choi, K.-H., Gaynor, J. B., White, K. G., Lopez, C., Bosio, C. M., Karkhoff-Schweizer, R. R., & Schweizer, H. P. (2005). A Tn7-based broad-range bacterial cloning and expression system. Nature Methods, 2(6), 443-8.

Datsenko, K. A., & Wanner, B. L. (2000). One-step inactivation of chromosomal genes in Escherichia coli K-12 using PCR products. Proceedings of the National Academy of Sciences of the United States of America, 97(12), 6640-5.

De Berardinis, V., Vallenet, D., Castelli, V., Besnard, M., Pinet, A., Cruaud, C., . . . Weissenbach, J. (2008). A complete collection of single-gene deletion mutants of Acinetobacter baylyi ADP1. Molecular Systems Biology, 4, 174.

Dykxhoorn, D. M., St. Pierre, R., & Linn, T. (1996). A set of compatible tac promoter expression vectors. Gene, 177(1-2), 133-136.

Feldman, M. F., Wacker, M., Hernandez, M., Hitchen, P. G., Marolda, C. L., Kowarik, M., . . . Aebi, M. (2005). Engineering N-linked protein glycosylation with diverse O antigen lipopolysaccharide structures in Escherichia coli. Proceedings of the National Academy of Sciences of the United States of America, 102(8), 3016-21.

Figurski, D. H., & Helinski, D. R. (1979). Replication of an origin-containing derivative of plasmid RK2 dependent on a plasmid function provided in trans. Proceedings of the National Academy of Sciences, 76(4), 1648-1652.

Harding, C. M., Tracy, E. N., Carruthers, M. D., Rather, P. N., Actis, L. A., & Munson, R. S. (2013). Acinetobacter baumannii strain M2 produces type IV pili which play a role in natural transformation and twitching motility but not surface-associated motility. mBio, 4(4), e00360-13.

Hunger, M., Schmucker, R., Kishan, V., & Hillen, W. (1990). Analysis and nucleotide sequence of an origin of an origin of DNA replication in Acinetobacter calcoaceticus and its use for Escherichia coli shuttle plasmids. Gene, 87(1), 45-51.

Kumar, A., Dalton, C., Cortez-Cordova, J., & Schweizer, H. P. (2010). Mini-Tn7 vectors as genetic tools for single copy gene cloning in Acinetobacter baumannii. Journal of Microbiological Methods, 82(3), 296-300.

Lee, E. C., Yu, D., Martinez de Velasco, J., Tessarollo, L., Swing, D. A., Court, D. L., . . . Copeland, N. G. (2001). A highly efficient Escherichia coli-based chromosome engineering system adapted for recombinogenic targeting and subcloning of BAC DNA. Genomics, 73(1), 56-65.

Nakar, D., & Gutnick, D. L. (2001). Analysis of the wee gene cluster responsible for the biosynthesis of the polymeric bioemulsifier from the oil-degrading strain Acinetobacter lwoffii RAG-1. Microbiology, 147(7), 1937-1946.

Niu, C., Clemmer, K. M., Bonomo, R. A., & Rather, P. N. (2008). Isolation and characterization of an autoinducer synthase from Acinetobacter baumannii. Journal of Bacteriology, 190(9), 3386-92.

Scott, N. E., Kinsella, R. L., Edwards, A. V. G., Larsen, M. R., Dutta, S., Saba, J., . . . Feldman, M. F. (2014). Diversity Within the O-linked Protein Glycosylation Systems of Acinetobacter Species. Molecular & Cellular Proteomics: MCP, 13(9), 2354-70.

Wacker, M., Linton, D., Hitchen, P. G., Nita-Lazar, M., Haslam, S. M., North, S. J. Aebi, M. (2002). N-linked glycosylation in Campylobacter jejuni and its functional transfer into E. coli. Science (New York, N.Y.), 298 (5599), 1790-3.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A method of glycosylating a protein in a bacterial cell, the method comprising glycosylating a fusion protein comprising ComP, with an N-glycan in a bacterial cell, using a PglL$_{ComP}$ O-oligosaccharyltransferase.

2. The method of claim 1 comprising expressing PglL$_{ComP}$ O-oligosaccharyltransferase, the ComP fusion protein, and the N-glycan together in the bacterial cell.

3. The method of claim 1, wherein the ComP fusion protein comprises an adjuvant or carrier.

4. The method of claim 1, wherein the bacterial cell is *Acinetobacter* or *E. coli*.

5. The method of claim 1, wherein the N-glycan is derived from *Campylobacter*.

6. The method of claim 5, wherein the N-glycan is a *Campylobacter jejuni* N-heptasaccharide.

7. The method of claim 4, wherein the *Acinetobacter* is *A. baylyi, A. baumannii, A. nosocomialis*, or *A. calcoaceticus*.

8. A conjugate vaccine comprising the glycosylated ComP fusion protein produced in accordance with the method of claim 1.

9. The method of claim 4, wherein the bacterial cell is *E. coli*.

10. The conjugate vaccine of claim 8, wherein the vaccine comprises an adjuvant or carrier.

11. A conjugate vaccine comprising the glycosylated ComP fusion protein produced in accordance with the method of claim 2.

12. The conjugate vaccine of claim 11, wherein the vaccine comprises an adjuvant or carrier.

13. A conjugate vaccine comprising the glycosylated ComP fusion protein produced in accordance with the method of claim 5.

14. The conjugate vaccine of claim 13, wherein the vaccine comprises an adjuvant or carrier.

15. A conjugate vaccine comprising the glycosylated ComP fusion protein produced in accordance with the method of claim 6.

16. The conjugate vaccine of claim 15, wherein the vaccine comprises an adjuvant or carrier.

* * * * *